US008173376B2

(12) United States Patent
De Koninck et al.

(10) Patent No.: US 8,173,376 B2
(45) Date of Patent: May 8, 2012

(54) METHOD FOR IDENTIFYING COMPOUNDS FOR TREATMENT OF PAIN

(75) Inventors: Yves De Koninck, Ste-Foy (CA); Paul De Koninck, Cap Rouge (CA); Jeffrey A. M. Coull, Toronto (CA)

(73) Assignee: Universite Laval, Quebec, Quebec (CA)

( * ) Notice: Subject to any disclaimer, the term of this patent is extended or adjusted under 35 U.S.C. 154(b) by 0 days.

(21) Appl. No.: 12/722,938

(22) Filed: Mar. 12, 2010

(65) Prior Publication Data
US 2010/0330586 A1   Dec. 30, 2010

Related U.S. Application Data

(62) Division of application No. 10/556,221, filed as application No. PCT/CA2004/000726 on May 14, 2004, now Pat. No. 7,709,207.

(60) Provisional application No. 60/470,885, filed on May 16, 2003.

(51) Int. Cl.
*G01N 33/53* (2006.01)
*C12Q 1/68* (2006.01)

(52) U.S. Cl. .......................... 435/7.1; 435/6.1; 436/501

(58) Field of Classification Search ........................ None
See application file for complete search history.

(56) References Cited

U.S. PATENT DOCUMENTS

| 4,806,463 A | 2/1989 | Goodchild |
| 5,004,810 A | 4/1991 | Draper |
| 5,034,506 A | 7/1991 | Summerton et al. |
| 5,087,617 A | 2/1992 | Smith |
| 5,098,890 A | 3/1992 | Gewirtz et al. |
| 5,135,917 A | 8/1992 | Burch |
| 5,166,195 A | 11/1992 | Ecker |
| 5,194,428 A | 3/1993 | Agrawal et al. |
| 5,264,423 A | 11/1993 | Cohen et al. |
| 5,276,019 A | 1/1994 | Cohen et al. |
| 5,286,717 A | 2/1994 | Cohen et al. |
| 5,539,082 A | 7/1996 | Nielsen et al. |
| 5,932,435 A | 8/1999 | Atkins et al. |
| 2002/0028779 A1 | 3/2002 | High et al. |
| 2002/0132788 A1 | 9/2002 | Lewis et al. |
| 2002/0173478 A1 | 11/2002 | Gewirtz |

FOREIGN PATENT DOCUMENTS

| DE | 33 25 506 A1 | 1/1985 |
| WO | 93/00939 A1 | 1/1993 |
| WO | 95/21611 A2 | 8/1995 |
| WO | 96/19233 A2 | 6/1996 |
| WO | 01/85151 A2 | 11/2001 |
| WO | 02/102232 A2 | 12/2002 |
| WO | 2004/032870 A2 | 4/2004 |

OTHER PUBLICATIONS

Pitcher et al. (2007). Molecular Pain. 3:17, pp. 1-8.*
Cramer et al. (2008). Molecular Pain. 4:36, pp. 1-8.*
Payne et al. (1995). The Journal of Biological Chemistry. 270:17977-17985.*
European Search Report: Appln. No. EP05745081 (2009).
International Search Report: Appln. No. PCT/CA2005/000738 (2005).
Kochuvelikakam O. Aley, et al; "Role of Protein Kinase A in the Maintenance of Inflammatory Pain", The Journal of Neuroscience, Mar. 15, 1999, 19(6), pp. 2181-2186.
Colin T. Buckley, et al; "Identification of Phospholipase C-gamma 1 as a Mitogen-activated Protein Kinase Substrate" The Journal of Biological Chemistry, vol. 279, Issue of Oct. 1, 2004, pp. 41807-41814.
Graham Carpenter, et al: "Phospholipase C-gamma as a Signal-Transducing Element", Experimental Cell Research 253(1), pp. 15-245, Nov. 25, 1999.
S.R.Chaplan. et al; "Quantitative assessment of tactile allodynia in the rat paw", Journal of Neuroscience Methods, 53, pp. 55-63; Received Oct. 4, 1993, revised Jan. 28, 1994; accepted Jan. 28, 1994.
Terence J. Coderre, et al; "The utility of excitatory amino acid (EAA) antagonists as analgesic agents. II. Assessment of the antinociceptive activity of combinations of competitive and non-competitive NMDA antagonists with agents acting at allosteric-glycine and polyamine receptor sites", Pain, 59, pp. 353-359, Received Aug. 20, 1993, revision received Feb. 22, 1994, accepted Mar. 21, 1994.
Terence J. Coderre, et al; "The Contribution of Excitatory Amino Acids to Central Sensitization and Persistent Nociception after Formalin-induced Tissue Injury", The Journal of Neuroscience, Sep. 1992, 12(9): pp. 365-3670.
Jeffrey A.M. Coull; et al; "Trans-synaptic shift in anion gradient in spinal lamina I neurons as a mechanism of neuropathic pain", Nature, vol. 424; Aug. 21, 2003, pp. 938-942.
Eric Delpire, et al; "Human and Murine Phenotypes Associated with Defects in Cation-Chloride Cotransport", Annu. Rev. Physiol. vol. 64, pp. 803-843 (vol. publication date Mar. 2002).
G.M.Deplater, et al; "Venom From the Platypus, *Omithorhynchus anatinus*, Induces a Calcium-Dependent Current in Cultured Dorsal Root Ganglion Cells", American Physiological Society Journal of Neurophysiology, pp. 1340-1345; Submitted Mar. 7, 2000. Accepted in final form Nov. 20, 2000.
A Met Dogrul, et al; "Effects of Intrathecally Administered Aminoglycoside Antibiotics, Calcium-Channel lockers, Nickel and Calcium on Acetic Acid-Induced Writhing Test in Mice", Gen. Pharmac. vol. 30, No. 4, pp. 613-616; Apr. 1998.
Satoru Ebihara, et al; "Gramicidin-perforated patch recording: GABA response in mammalian neurons with intact intracellular chloride", The Journal of Physiology, vol. 484 (Pt1), Issue: Pt1, Publisher: Physiological Soc, pp. 77-86, Apr. 1, 1995.
L. Fang, et al; "Camnk II Signaling in Central Senzitization in a Rat Model of Visceral Pain", 2001; Database Biosis 'Online 27, No. 2, 2163.

(Continued)

*Primary Examiner* — Christine J Saoud
*Assistant Examiner* — Jon M Lockard
(74) *Attorney, Agent, or Firm* — Ladas & Parry LLP

(57) ABSTRACT

Methods and products for the attenuation or treatment of pain and the reduction of nociception are described. The methods and products are based on the modulation of CNS intracellular chloride levels. The methods and products may also relate to modulation of the activity and/or expression of a chloride transporter, such as the KCC2 potassium-chloride cotransporter. Also described herein are commercial packages and uses based on such modulation. Related methods for identifying or characterizing a compound for the treatment of pain, the reduction of nociception and the diagnosis and prognostication of pain are also described.

6 Claims, 25 Drawing Sheets

OTHER PUBLICATIONS

NB Farber, et al; "Antiepileptic drugs and agents that inhibit voltage-gated sodium channels prevent NMDA antagonist neurotoxicity", Molecular Phyciatry (2002) 7, pp. 726-733; Received Dec. 6, 2001: revised Jan. 5, 2002; accepted Jan. 8, 2002.

Peter W. Flatman, et al; "Role of protein kinases in regulating sheep erythrocyte K-Cl cotransport", American Physiological Society Cell Physiology, Jul. 1996, vol. 271, No. 1, pp. C255-C263.

H. Furue, et al; "Rapid Report: Responsiveness of rat substantia gelatinosa neurons to mechanical but not thermal stimuli revealed by in vivo patch-clamp recording", Journal of Physiology (1999), 521.2, pp. 529-535, Received Jul. 2, 1999; accepted after revision Oct. 5, 1999.

Nicoletta Galeotti, et al; "The Phospholipase C-1P3 Pathway is Involved in Muscarinic Antinociception", Neurophychopharmacolgy; vol. 28, Issue 5, May 2003; advanced online publication, Nov. 11, 2002.

A. I. Gulyás, et al; "The KCl cotransporter, KCC2, is highly expressed in the vicinity of excitatory synapses in the rat hippocampus", european Journal of Neuroscience, vol. 13, pp. 2205-2217, 2001; Received Nov. 30, 2000, revised Apr. 16, 2001, accepted Apr. 19, 2001.

Heidi C. Howard, et al; "The K-Cl cotransporter KCC3 is mutant in a severe peripheral neuropathy associated with agenesis of the corpus callosum", Nature Genetics, vol. 32, Nov. 2002, pp.384-392.

Xiao-Ying Hua, et al; "Inhibition of spinal protein kinase C reduces nerve injury-induced tactile allodynia in neuropathic rats", Neuroscience Letter 276; pp. 99-102 (1999); Received Sep. 10, 1999;accepted Sep. 27, 1999.

Wolfgang Jarolimek, et al; "A Furosemide-Sensitive $K^+$-$Cl^-$ Cotransporter Counteracts Intracellular $Cl^-$ Accumulation and Depletion in Cultured Rat Midbrain Neurons", The Journal of Neuroscience, Jun. 15, 1999, 19(12); pp. 4695-4704.

Farzana Karim; et al; "Metabotropic Glutamate Receptor Subtypes 1 and 5 Are Activators of Extracellular Signal-Regulated Kinase Signaling Required for Inflammatory Pain in Mice", The Journal of Neuroscience, Jun. 1, 2001, 21(11): pp. 3771-3779.

A. Florence Keller, et al; "Region-Specific Developmental Specialization of GABA-Glycine Cosynapses in Laminas I-II of the Rat Spinal Dorsal Horn", The Journal of Neuroscience, Oct. 15, 2001, 21(20): pp. 7871-7880.

Wolfgang Kelsch, et al; "Insulin-Like Growth Factor 1 and a Cytosolic Tyrosine Kinase Activate Chloride Outward Transport during Maturation of Hippocampal Neurons", The Journal of Neuroscience, Nov. 1, 2001, 21(21): pp. 8339-8347.

Vesa K. Kontinen, M.D., et al; "Electrophysiologic Evidence for Increased Endogenous GABAergic but Not Glycinergic Inhibitory Tone in the Rat Spinal Nerve Ligation Model of Neuropathy", Anesthesiology, vol. 94, No. 2, Feb. 2001, pp. 333-339.

Hyung Taek Lee et al; "Cdk4 and $p27^{Kip1}$ play a role in PLC-gamma 1-mediated mitogenic signaling pathway of 18 kDa FGF-2 in corneal endothelial cells", Molecular Vision 2002; 8:17-25; Received Nov. 27, 2001; Accepted Feb. 6, 2002; Published Feb. 8, 2002.

Zachary F. Mainen, et al; "A Model of Spike Initiation in Neocortical Pyramidal Neurons", Neuron, vol. 15, pp. 1427-1439, Dec. 1995.

Michael E. Maragoudakis, et al; "Basement membrane biosynthesis as a target for developing inhibitors of angiogenesis with anti-tumor properties", Kidney International, vol. 43, pp. 147-150; Jan. 1993.

Ian C.B. Marshall, et al; "Activation of vanilloid receptor 1 by resiniferatoxin mobilizes calcium from inositol 1,4,5-trisphosphate-sensitive stores", British Journal of Pharmacology; vol. 138, pp. 172-176; Jan. 2003;Published online Jan. 7, 2003;.

Thomas J. Martin, et al; "Pharmacology of Opioid and nonopioid Analgesics in Chronic Pain States", The Journal of Pharmacology and Experimental Therapeutics, vol. 299, No. 3, Received Mar. 26, 2001; accepted Jul. 6, 2001.

Ronald Melzack, et al; "Pain Mechanisms: A New Theory", Science, Nov. 19, 1965, vol. 150, No. 3699, pp. 971-979.

K. Miller-Decker; "Interruption of TPA-Induced Signals By An Antiviral and Antitumoral Xanthate Compound: Inhibition of a Phospholipase C-Type Reaction", Biochemical and Biophysical Research Communications, vol. 162, No. 1, Jul. 14, 1989, pp. 198-205.

Martha M. Monick, et al; "A Phosphatidylcholine-Specific Phospholipase C Regulates Activation of p42/44 Mitogen-Activated Protein Kinases in Lipopolysaccharide-Stimulated Human Alveolar Macrophases[1]", Journal of Immunology, vol. 162, No. 5, pp. 3005-3012; Mar. 1, 1999.

Kimberly A Moore, et al; "Partial Peripheral Nerve Injury Promotes a Selective Loss of GAGAergic Inhibition in the Superficial Dorsal Horn of the Spinal Cord", The Journal of Neuroscience, Aug. 1, 2002, 22(15): pp. 6724-2731.

Tony Mosconi, et al; "Fixed-diameter polyethylene cuffs applied to the rat sciatic nerve induce a painful neuropathy: ultrastructural morphometric analysis of axonal alterations", Pain, vol. 64, Issue 1, Jan. 1996, pp. 37-57.

David B. Mount, et al; "Cloning and Characterization of KCC3 and KCC4, New Members of the Cation-Chloride Cotransporter Gene Family", The Journal of Biological Chemistry, vol. 274, No. 23, Issue of Jun. 4, 1999, pp. 16355-16362.

Keita Narikawa, et al; "In Vivo Patch-Clamp Analysis of IPSCs Evoked in Rat Substantia Gelatinosa Neurons by Cutaneous Mechanical Stimulation", Journal of Neurophysiology, Oct. 2000, vol. 84, No. 4, pp. 2171-2174; Submitted Mar. 2, 2000, Accepted in final form Jun. 12, 2000.

M. Narita, et al; "Role of the Phosphatidylinositol-Specific Phospholipase C Pathway in δ-Opioid Receptor-Mediated Antinociception in The Mouse Spinal Cord", Neuroscience, vol. 99, No. 2, pp. 327-331, Sep. 11, 2000.

Dong-Young Noh, et al; "Expression of Phospholipase C-gamma 1 and its Transcriptional Regulators in Breast Cancer Tissues", AntiCancer Research 18(4A): 2643-2648; Jul.-Aug. 1998;.

Maria Ocana, et al; "Analgesic effects of centrally administered aminoglycoside antibiotics in mice", Neuroscience Letters, 126, pp. 67-70; Received Nov. 8, 1990; Revised version received Feb. 7, 1991: Accepted Feb. 11, 1991.

John A Payne; "Functional characterization of the neuronal-specific K-Cl cotransporter: implications for $[K^+]_o$ regulation", American Journal of Physiology Cell Physiology, Nov. 1997, vol. 273, No. 5, pp. C1516-C1525; Submitted May 8, 1997; Accepted in final form Jul. 2, 1997.

John A Payne, et al; "Molecular Characterization of a Putative K-Cl Cotransporter in Rat Brain", The Journal of Biological Chemistry, vol. 271, No. 27, Issue of Jul. 5, 1996, pp. 16245-16252.

E. Polgar et al; "Abstract View: GABA-And Glycine-Immunoreactivity in The Spinal Dorsal Horn of Rats with Peripheral Nerve Injury", Soc. Neurosci Abstr 28, 655.3. Jun. 11, 2002.

W.A. Prado, et al; "Antinociceptive potency of aminoglycoside antibiotics and magnesium chloride: a comparative study on models of phasic and incisional pain in rats", Brazilian Journal of Medical and Biological Research, 2002, 35, pp. 395-403; Received Aug. 3, 2001, Accepted Feb. 4, 2002.

Steven A. Prescott, et al; "Four cell types with distinctive membrane properties and morphologies in lamina I of the spinal dorsal horn of the adult rat", Journal of Physiology, 539,3 pp. 817-836, Mar. 15, 2002.

Toril Rabben, et al; "Prolonged Analgesic Effect of Ketamine, an $N$-Methyl-D-Aspartate Receptor Inhibitor, in Patients with Chronic Pain", The Journal of Pharmacology and Experimental Therapeutics, vol. 289, No. 2, pp. 1060-1066, Received for Publication Jul. 29, 1998; Accepted for Publication Dec. 15, 1998.

Sue Goo Rhee; "Regulation of Phosphoinositide-Specific Phospholipase C", Annual Review of Biochemistry, vol. 70, p. 281-312 (vol. publication date Jul. 2001).

Alfredo Ribeiro-Da-Silva; "3 Substantia Gelatinosa of Spinal Cord", The Rat Nervous System, Second Edition, G. Paxinos (ed.), pp. 47-59, Academic Press, Sydney, Australia 1995.

A Ribeiro-Da-Silva, et al; "Two Types of Synaptic Glomeruli and Their Distribution in Laminae I-Ill of the Rat Spinal Cord", The Journal of Comparative Neurology 209: pp. 176-186, Accepted Apr. 23, 1982.

Claudio Rivera, et al; "The $K^+/Cl^-$ co-transporter KCC2 renders GABA hyperpolarizing during neuronal maturation", Nature vol. 397, Jan. 21, 1999, pp. 251-255.

Pablo Rudomin, et al; "Presynaptic inhibition in the vertebrate spinal cord revisited", Exp. Brain Res; 129, pp. 1-37, Received Dec. 16, 1998; Accepted Jun. 1, 1999.

Gerhard Sauer, et al; "DNA and RNA virus species are inhibited by xanthates, a class of antiviral compounds with unique properties", Proc. Natl. Acad. Sci, vol. 81, pp. 3263-3267, Jun. 1984, Applied Biology.

Stefan Schutze, et al; "TNF Activates NF-$_k$ B by Phosphatidylcholine-Specific Phospholipase C-Induced "Acidic" Sphingomyelin Breakdown", Cell, vol. 71, pp. 765-776, Nov. 27, 1992.

M.G. Serpell; "Gabapentin in neuropathic pain syndromes: a randomised, double-blind, placebo-controlled trial", Pain, vol. 99, pp. 557-566, Received Apr. 10, 2001; received in revised from Jun. 28, 2002; accepted Jul. 8, 2002.

Meng-Ru Shen, et al; "The KCl cotransporter isoform KCC3 can play an important role in cell growth regulation", PNAS, Dec. 4, 2001, vol. 98, No. 25, pp. 14714-14719.

Liming Shu, et al; "Regulation of Phospholipase C-gamma Activity by Glycosphingolipids", The Journal of Biological Chemistry, vol. 277, No. 21, Issue of May 24, 2002, pp. 18447-18453.

A. Sik, et al; "Distribution of Chloride Channel-2-Immunoreactive Neuronal and Astrocytic Processes in the Hippocampus", Neuroscience, vol. 101, No. 1, pp. 51-65, Oct. 27, 2000.

Mark R. Smith, et al; "Inhibition of Serum-and Ras-Stimulated DNA Synthesis by Antibodies to Phospholipase C", Science, vol. 247, No. 4946, pp. 1074-1077, Mar. 2, 1990.

Forrest L. Smith; et al; "Involvement of phospholipid signal transduction pathways in morphine tolerance in mice", British Journal of Pharmacology; 128, pp. 220-226; Sep. 1999.

David L. Somers; et al; "Dorsal horn synaptosomal content of aspartate, glutamate, glycine and GABA are differentially altered following chronic constriction injury to the rat sciatic nerve", Neuroscience Letters vol. 323, Issue 3, May 3, 2002 pp. 171-174.

Kevin J. Staley, et al; "Ionic Mechanisms of Neuronal Excitation by Inhibitory GABA$_A$ Receptors", Science, vol. 269; Issue: 5226; Aug. 18, 1995, pp. 977-981.

Kevin Strange, et al; "Dependence of KCC2 K-Ci cotransporter activity on a conserved carboxy terminus tyrosine residue", American Journal of Physiology Cell Physiology, Sep. 2000, vol. 279; No. 3, pp. C860-C867.

Ki-Wug Sung, et al; "Abnormal GABA$_A$ Receptor-Mediated Currents in Dorsal Root Ganglion Neurons Isolated from Na-K-2Cl Cotransporter Null Mice", The Journal of Neuroscience, Oct. 15, 2000, 20(20): pp. 7531-7538.

K. Tan-No; et al; "Intrathecal spermine and spermidine at high-doses induce antinociceptive effects in the mouse capsaicin test", Biogenic Amines, vol. 17, No. 4-6, 2002 pp, 313-320(8).

Nam-Sik Woo, et al; "Hyperexcitability and Epilepsy Associated With Disruption of the Mouse Neuronal-Specific K-Cl Cotransporter Gene", Hippocampus, 12:258-268 (2002); Article first published online Feb. 25, 2002.

Clifford J. Woolf, et al; "Neuronal Plasticity: Increasing the Gain in Pain", Science, vol. 288, Jun. 9, 2000, pp. 1765-1768.

Zhongjian XIE, et al; "Phospholipase C-gamma1 Is Required for Calcium-induced Keratinocyte Differentiation", The Journal of Biological Chemistry, vol. 274, No. 29, Issue of Jul. 16, 1999; pp. 20421-20424.

USPTO OA mailed Feb. 10, 2009 in connection with U.S. Appl. 10/556,221.

USPTO OA mailed Apr. 1, 2009 in connection with U.S. Appl. No. 10/556,221.

USPTO NOA mailed Nov. 30, 2009 in connection with U.S. Appl. No. 10/556,221.

\* cited by examiner

Human KCC2 polypeptide and DNA sequences (Mount, D.B. and Song, L. (2002) Brain Res. Mol. Brain Res. 103 (1-2), 91-105; ACCESSION : AF208159)

Human KCC2 polypeptide (SEQ ID NO:2) :

MPNNLTDCEDGDGGANPGDGNPKESSPFINSTDTEKGKEYDGKN

MALFEEEMDTSPMVSSLLSGLANYTNLPQGSREHEEAENNEGGKKKPVQAPRMGTFMG

VYLPCLQNIFGVILFLRLTWVVGIAGIMESFCMVFICCSCTMLTAISMSAIATNGVVP

AGGSYYMISRSLGPEFGGAVGLCFYLGTTFAGAMYILGTIEILLAYLFPAMAIFKAED

ASGEAAAMLNNMRVYGTCVLTCMATVVFVGVKYVNKFALVFLGCVILSILAIYAGVIK

SAFDPPNFPICLLGNRTLSRHGFDVCAKLAWEGNETVTTRLWGLFCSSRFLNATCDEY

FTRNNVTEIQGIPGAASGLIKENLWSSYLTKGVIVERSGMTSVGLADGTPIDMDHPYV

FSDMTSYFTLLVGIYFPSVTGIMAGSNRSGDLRDAQKSIPTGTILAIATTSAVYISSV

VLFGACIEGVVLRDKFGEAVNGNLVVGTLAWPSPWVIVIGSFFSTCGAGLQSLTGAPR

LLQAISRDGIVPFLQVFGHGKANGEPTWALLLTACICEIGILIASLDEVAPILSMFFL

MCYMFVNLACAVQTLLRTPNWRPRFRYYHWTLSFLGMSLCLALMFICSWYYALVAMLI

AGLIYKYIEYRGAEKEWGDGIRGLSLSAARYALLRLEEGPPHTKNWRPQLLVLRVDQ

DQNVVHPQLLSLTSQLKAGKGLTIVGSVLEGTFLENHPQAQRAEESIRRLMEAEKVKG

FCQVVISSNLRDGVSHLIQSGGLGGLQHNTVLVGWPRNWRQKEDHQTWRNFIELVRET

TAGHLALLVTKNVSMFPGNPERFSEGSIDVWWIVHDGGMLMLLPFLLRHHKVWRKCKM

RIFTVAQMDDNSIQMKKDLTTFLYHLRITAEVEVVEMHESDISAYTYEKTLVMEQRSQ

ILKQMHLTKNEREREIQSITDESRGSIRRKNPANTRLRLNVPEETAGDSEEKPEEEVQ

LIHDQSAPSCPSSSPSPGEEPEGEGETDPEKVHLTWTKDKSVAEKNKGPSPVSSEGIK

DFFSMKPEWENLNQSNVRRMHTAVRLNEVIVKKSRDAKLVLLNMPGPPRNRNGDENYM

EFLEVLTEHLDRVMLVRGGGREVITIYS

Human KCC2 DNA (SEQ ID NO:1):

```
  1 atgcccaaca acctgacgga ctgcgaggac ggcgatgggg gagccaaccc gggtgatggc
 61 aaccccaagg aaagcagtcc cttcatcaac agcaccgaca cagagaaggg aaaggagtat
121 gatggcaaga acatgccctt gtttgaggag gagatggaca ccagccctat ggtgtcctcc
181 ttgctcagtg gcctggccaa ctacaccaac ctgccccagg gaagtaggga gcatgaagag
241 gcagaaaaca atgagggtgg aaaaaagaag ccggtgcagg ccccacgcat gggcaccttc
301 atgggcgtgt acctgccgtg cctgcagaac atctttggcg tcatcctctt cctgcggctc
361 acctgggtgg tgggcattgc aggcatcatg gagtccttct gcatggtgtt catctgctgc
```

FIG. 9A

```
 421 tcctgtacga tgctcacggc catctccatg agtgcaattg caacgaatgg tgttgtgcct
 481 gctggtggct cctactacat gatttccagg tctctgggcc cagagtttgg gggtgccgtg
 541 ggcctctgct tctacctggg cactaccttt gcaggagcca tgtacatcct gggcaccatc
 601 gaaatcctgc tggcttacct cttcccagcc atggccatct tcaaggcaga agatgccagt
 661 ggggaggcag cagccatgct gaacaacatg cgtgtttacg gcacctgtgt gctcacctgc
 721 atggccactg tggtgtttgt gggtgtcaag tatgtcaaca agtttgccct tgtcttcctg
 781 ggttgtgtca tcctctccat cctggccatc tatgctgggg tcatcaagtc tgccttcgac
 841 ccacccaact tcccgatctg cctcctgggt aaccgcacgc tgtctcgcca tggctttgat
 901 gtctgtgcca agctggcttg ggaaggaaat gagacggtga ccacacggct atggggcctt
 961 ttctgctcct ctcgcttcct caacgccacc tgtgatgaat acttcacccg aaacaatgtc
1021 acagagatcc agggcatccc tggtgctgcc agtggcctca tcaaagagaa cctctggagc
1081 tcctacctga ccaagggcgt gattgtggag aggagtggga tgacctcggt gggcctggcc
1141 gatggcactc ctatcgacat ggaccaccct tatgtcttca gtgatatgac ctcctacttc
1201 accctgctgg ttggcatcta cttcccctca gtcacaggga tcatggctgg ttctaaccgc
1261 tctggggacc tgagggatgc ccagaagtca atccccactg gcaccatcct ggccatcgcc
1321 accacctctg ctgtctacat cagctccgtt gttctgtttg gggcctgcat tgaggggtc
1381 gtcctgcggg acaagtttgg cgaagctgtg aatggcaacc tcgtggtggg cactctggcc
1441 tggccatctc catgggtaat tgtcatcgga tccttcttct ccacctgtgg ggctgggctg
1501 cagagcctca cgggggcccc acgcctgctg caggccatcc cgagggatgg cattgtgccc
1561 ttcctgcagg tctttggcca tggcaaggcc aatggagagc cgacctgggc cctgctcctg
1621 actgcctgca tctgcgagat tggcatcctc attgcatccc tcgacgaggt ggccccccatc
1681 ctctctatgt tcttcctgat gtgctacatg tttgtgaatc tggcctgtgc agtgcagacg
1741 ctgctgagga cacccaactg gaggccacgc tttcgatatt accactggac cctctccttc
1801 ctgggcatga gcctctgcct ggccctcatg ttcatctgct cctggtatta tgcactggta
1861 gccatgctca ttgctggact catctacaag tacattgagt accgtgggc agagaaggag
1921 tggggcgatg ggatacgagg tctgtctctc agtgcggctc gctatgccct cttacgcctg
1981 gaggaagggc ccccacacac caagaactgg aggccacagc tgctggtgct ggtgcgtgtg
2041 gaccaagacc agaatgtggt gcaccccag ctgctctcac tgacctccca gctgaaggca
2101 gggaagggcc tgaccatcgt gggctctgtc cttgagggca cctttctgga aaatcatcca
2161 caggcccagc gggcagaaga gtctatcagg cgcctgatgg aggcagagaa ggtgaaggc
2221 ttctgccagg tggtgatctc ctccaacttg cgtgatggcg tgtcccatct gatccagtcc
2281 gggggcctcg gggggctgca gcacaacact gtgcttgttg gctggccccg caactggcgc
2341 cagaaggaag atcatcagac gtggaggaac ttcattgagc tggtccggga aaccacagct
2401 ggccacttag ccctgctggt caccaagaac gttttccatg ttcctgggaa ccctgagcgc
2461 ttctctgagg gcagcatcga cgtttggtgg attgtgcacg atggaggcat gctcatgctg
2521 ctgcccttcc tgctgcggca ccacaaggtc tggcggaagt gcaagatgcg tatcttcact
2581 gtggcccaga tggatgacaa tagcatccag atgaagaagg atctgaccac atttctgtat
2641 catttacgca tcactgcgga ggtcgaggtg gtggagatgc atgagagcga catctcagct
2701 tacacctatg agaagacgtt ggtgatggag cagcgttccc agatcctcaa acagatgcat
2761 ttaaccaaga atgagcggga gcggagatc cagagtatca cagatgagtc acgaggctca
2821 atccggagaa agaatccagc caacacgcgg ctccgcctga acgtccaga agagacggct
2881 ggtgacagtg aagagaagcc agaggaggag gtgcagctga tccacgatca gagtgctccc
2941 agctgcccca gcagctcccc gtccccaggg gaggagcctg aggggaagg ggagacagat
3001 ccggagaagg tgcatctcac ctggaccaag acaagtcgg tggcagagaa gaataagggc
3061 cccagtcctg tctcctctga gggcatcaag gacttcttca catgaagcc ggagtgggag
3121 aacttgaacc agtccaacgt gcggcgcatg cacacgggcc tgcggctgga cgaggtcatc
3181 gtgaagaaat cccgggacgc caagcttgtt ttgctcaaca tgcctgggcc tccccgcaac
3241 cgcaatggtg atgaaaacta catggagttt ctcgaggtcc tcacagagca cctggaccgg
3301 gtgatgctgg tccgcgtgg tggccgagag gtcatcacca tctactcctg agaaccaggt
3361 cctgccaccc gggcccgagc gcgcccggcc gcggctccg gagccctcgc cgcgccccc
3421 gccgctgtca ccgtttacat acagaccctg tgcccgtgtc ctggcccctt accccgctgc
3481 ctgaagcccg gaggccacgc ctgttgggc tgattcggag agggcgcccc gccgcgcaga
3541 gaccagagct cctcagtgcc agtttggccc ctgggtcttc gctgcccttt ttctaagccc
3601 ggcctcgtct cgccggagga gacgctgcaa taaaggttgg gagaaggcgc ggaaggaga
3661 ggagctgggg ccttggggac ccccaggtag tccatgcggc ccattcctcc ccttcccact
3721 cccgccgcgg tcctcgctct gcgctcctcc ggcgctgctc cctggctccc ggcggccgg
3781 aggcccgcgg ggtgggaagg ccgcgcttgc cgtctccgcc gccccttctc gccgagccgt
3841 ggggcgcggg cggccgagcc tatacatagt gtacaggaga catcgcgtgt atttttaacg
```

FIG. 9B

```
3901 tccccatatt tatgtgacta gaagcgcaac agacttctcg ccatagtcga gctctcccgc
3961 tgggggcact gcggggaggc gaggcctcgg gaagctgaat tttccttgac gtccaagagt
4021 ttgagagcga aagtgcttta ggcccaggcg ggggtcgtgg cctcgttccc tcgacacctc
4081 cgtcctgctc tcgcctcttc gcccttccg cgcgcccttg gcttcccacc ctcctctcca
4141 gtcctttcc gagatgaggt gagacaaggg tccaactttt cctggattcg cctcccagcg
4201 gacgtgagct tccactgcgg ctgcagagac gcgagcaacc tcttctcatc ggctcttatg
4261 caagttgggg ccaggatagg ggaggggtgc tcctcaagag gaagaaaccg agaggcccgc
4321 gccccaccga ggaagccccg cccggtgcc ttcgctgggg agcaggcgtc tctcctcagt
4381 cggcttgtcg cctgctcccc gtatcccatg gctcctcgcc aaagactgaa attgtggagc
4441 tggagggcgc cccctcccg gagtttcctc cctgggacaa gtgagggagg agggggccga
4501 ttctggttta ggggccggac ccactgagag gccccagagc cgcccgtgat gttcctcccc
4561 cgtccccatc tggcagctcc tgtctcgcct gagggaccca gccgccttct ccgtgctctg
4621 gggccgggcc tcgctgctta gcagcggcct ctagctccgt ctcccgggga cctgggcctg
4681 agggagggct ggagtcagca cgcgctttgt ccttagcgcc tgtctgctct cctctaacta
4741 ggacccaggg cctttggctt ccccagctca tccttggccc ttccgctcca ccagcctggt
4801 ctgaggcgtg ctctgtcctt agagaaggcg cggtggccgg gttcccttcc cctagggcac
4861 attactaagg gggtcaggca ctgcatgctc gttccagcac catctgggac tgggtacagt
4921 acctccagcc ccagggccct gacctgcgca cctagcttga catctcacgc acctcccaga
4981 gctggcgcca ctgagtaatc cggacctcac cacctctttt cctttgagcc caaggcagag
5041 ctagagctgg agctggcgcc acccagacag cgtcaggtgt ggctggggta ggtttggagg
5101 tctgccagtt acgccaagtc ccctctgaga ttcgatcagg ggactggata gattctttca
5161 ggtactcaat caggaagctg gaggtgttag acaccagccc cctgcatcct tcagtagacc
5221 tccctctgaa caccacagcc aggtcctgcc ttctggggc ctgaatattc cagagctgat
5281 gtgatgggct gtgcagaagg gggctgtatc aacatcaatt agggaaccaa agttgcacta
5341 tctgggccca gattgtctgg ttggcaagag caaagtttcc gttgatgaaa cagacatccc
5401 acaacaaaaa cccaagtttt ctgtgctaca tgtgcaatat ttgttatgaa tgttatcaca
5461 agtcattcat caagttatct ttataatcac tgtagttaga tgtttcatgt ccattcaagt
5521 gacttttatt ctgagtgcaa tatttcaata gccttgtagt gataactagt gttgcttttg
5581 tttagatgat ctatgtgcag ggcaatgcaa tgaagttgaa accccttggt aataggagag
5641 gttgcaaacc aaatcaagag tatttattac tattactgct attattatta ggcctgcctt
5701 taattttcag tgtaagtgtt cagtatgccg catcctgcct cagtattgat cttgtgttct
5761 ttgtgccaat atgaaaagga gagggttggg tcttttcttt attgttgaat gctcccattt
5821 aatgctttat ggcttttact gtattacttt tttagactcc cgtctgcaca aaatgcaata
5881 aaaataattt tattataaaa aaaaaaa
```

FIG. 9C

Mouse KCC2 (K-Cl cotransporter [Slc12a5]) polypeptide and DNA sequence (Ehringer, M.A., et al. (2001) Mamm. Genome 12 (8), 657-663; ACCESSION: AF332064)

Mouse KCC2 polypeptide (SEQ ID NO:4) :

MLNNLTDCEDGDGGANPGDGNPKESSPFINSTDTEKGREYDGRN

MALFEEEMDTSPMVSSLLSGLANYTNLPQGSREHEEAENNEGGKKKPVQAPRMGTFMG

VYLPCLQNIFGVILFLRLTWVVGIAGIMESFCMVFICCSCTMLTAISMSAIATNGVVP

AGGSYYMISRSLGPEFGGAVGLCFYLGTTFAGAMYILGTIEILLAYLFPAMAIFKAED

ASGEAAAMLNNMRVYGTCVLTCMATVVFVGVKYVNKFALVFLGCVILSILAIYAGVIK

SAFDPPNFPICLLGNRTLSRHGFDVCAKLAWEGNETVTTRLWGLFCSSRLLNATCDEY

FTRNNVTEIQGIPGAASGLIKENLWSSYLTKGVIVERRGMPSVGLADGTPVDMDHPYV

FSDMTSYFTLLVGIYFPSVTGIMAGSNRSGDLRDAQKSIPTGTILAIATTSAVYISSV

VLFGACIEGVVLRDKFGEAVNGNLVVGTLAWPSPWVIVIGSFFSTCGAGLQSLTGAPR

LLQAISRDGIVPFLQVFGHGKANGEPTWALLLTACICEIGILIASLDEVAPILSMFFL

MCYMFVNLACAVQTLLRTPNWRPRFRYYHWTLSFLGMSLCLALMFICSWYYALVAMLI

AGLIYKYIEYRGAEKEWGDGIRGLSLSAARYALLRLEEGPPHTKNWRPQLLVLVRVDQ

DQNVVHPQLLSLTSQLKAGKGLTIVGSVLEGTFLDNHPQAQRAEESIRRLMEAEKVKG

FCQVVISSNLRDGVSHLIQSGGLGGLQHNTVLVGWPRNWRQKEDHQTWRNFIELVRET

TAGHLALLVTKNVSMFPGNPERFSEGSIDVWWIVHDGGMLMLLPFLLRHHKVWRKCKM

RIFTVAQMDDNSIQMKKDLTTFLYHLRITAEVEVVEMHESDISAYTYEKTLVMEQRSQ

ILKQMHLTKNEREREIQSITDESRGSIRRKNPANPRLRLNVPEETACDNEEKPEEEVQ

LIHDQSAPSCPSSSPSPGEEPEGERETDPEVHLTWTKDKSVAEKNKGPSPVSSEGIKD

FFSMKPEWENLNQSNVRRMHTAVRLNEVIVNKSRDAKLVLLNMPGPPRNRNGDENYME

FLEVLTEQLDRVMLVRGGGREVITIYS

Mouse KCC2 DNA (SEQ ID NO:3) :

```
  1 gagcaagcga gcgagcggag aaggcgggca gaggggcgcg ggcgaagcgg cgcagccatc
 61 ccgagcccgg cgccgcgcag ccaccatgct caacaacctg acggactgcg aggacggcga
121 tgggggagcc aaccccggtg atggcaaccc caaagagagc agtcccttca tcaacagcac
181 ggacacggag aagggcagag agtacgatgg caggaacatg gccctgtttg aggaggagat
241 ggacaccagc ccatggtgat cctcctgct cagtgggctg ccaactaca ccaacctacc
301 ccagggaagt agagagcatg aagaagcaga aaataatgag ggtggaaaaa agaagccggt
```

FIG. 10A

```
 361 gcaggctcct cgaatgggca ccttcatggg tgtgtacctg ccgtgcctgc agaacatctt
 421 tggtgtcatc ctcttcctgc ggctcacgtg ggtggtgggc atcgcgggca tcatggagtc
 481 cttctgtatg gtcttcattt gctgctcctg tacgatgctc acagccattt ccatgagtgc
 541 aatcgcaacc aatggtgttg tgcctgctgg tggctcgtac tacatgattt ccaggtctct
 601 gggcccggag tttgggggcg ccgtgggcct ctgcttctac ctgggcacca cctttgctgg
 661 ggctatgtac atccttggca cgatcgagat cctgctggct tatctcttcc cagctatggc
 721 catcttcaag gcagaagatg ccagtgggga ggcggccgcc atgctgaaca acatgcgggt
 781 gtatggcacc tgtgtgctca cctgcatggc caccgttgtc tttgtgggtg tcaagtacgt
 841 caacaagttt gccttggtct tcctgggttg cgtcatcctg tccatcctgg ccatctatgc
 901 aggggtcatc aagtctgcct tcgacccacc caatttcccg atctgcctcc tggggaaccg
 961 cacgctgtct cgccatggct ttgatgtctg tgccaagctg gcttgggaag gaaatgagac
1021 agtgaccaca cggctctggg cctttttctg ctcctcccgc ctcctcaatg ccacctgtga
1081 tgagtacttc acccgaaaca atgtcacaga gatccagggc attcctggtg ctgccagtgg
1141 tctcatcaaa gagaacctgt ggagttctta cctgaccaaa ggggtgattg tcgagaggcg
1201 tgggatgccc tctgtgggcc tggcagacgg taccccgta gacatggacc accctatgt
1261 cttcagtgat atgacctcct acttcaccct gctcgttggt atctacttcc cctcagtcac
1321 aggatcatg gctggctcaa accgatctgg agacctgcgg gatgcccaga gtctatccc
1381 tactggaact atcctggcca ttgctaccac ctctgctgtc tacatcagct ctgttgttct
1441 gtttggagcc tgcatcgagg ggtcgtctt acgggacaag tttggggaag ctgtgaatgg
1501 caacttggtg gtgggcaccc tggcctggcc ttctccctgg gtcatcgtca taggctcttt
1561 cttctctacc tgtggggctg gattacagag cctcacaggg gccccacgtc tgctgcaggc
1621 catctcccgg gatggcatag tgcccttcct gcaggtcttt ggccatggca aagctaatgg
1681 agagccaacc tgggcgctgc tgctgactgc ctgcatctgt gagatcggca tcctcatagc
1741 ctccctggat gaggtcgccc ctatactttc catgttcttc ctaatgtgtt acatgtttgt
1801 gaacttggct tgtgcggtgc agacgctgct gaggacaccc aactggaggc cacgatttcg
1861 ctattaccac tggactctct ccttcctggg catgagcctc tgcctggccc tcatgttcat
1921 ttgctcctgg tactacgcac tggtggccat gctcattgcc ggactcattt ataagtacat
1981 cgagtaccgg ggggcggaga aggagtggga ggatgaaatc cgaggcctgt ctctcagtgc
2041 agcacgctat gctctcttgc gcctggagga aggacctccg catacgaaga actggaggcc
2101 ccagctgctg gtgctggtgc gtgtggacca ggatcagaac gtggtgcatc cgcagctgct
2161 ctccctgacc tcccagctca aggcagggaa gggcctgacc attgtgggct ccgtccttga
2221 gggcaccttt ctggacaacc atccacaggc tcagcgggca gaggagtcta tcaggcgcct
2281 gatggaggct gagaaggtga agggcttctg ccaggtagtg atctcctcca acctgcgtga
2341 tggtgtgtcc cacctgatcc agtctggggg cctcggggga ttgcaacaca ataccgtgct
2401 ggtgggctgg cctcgcaact ggaggcagaa ggaggatcat cagacatgga ggaacttcat
2461 cgaactggtc cgggaaacta cagccggcca cctgccctg ctggtcacca agaatgtttc
2521 catgtttccc gggaaccctg agcgcttctc ggagggcagc attgacgtgt ggtggattgt
2581 gcacgacggg ggcatgctca tgctgctgcc cttcctgctg cgacaccaca aggtctggag
2641 gaaatgcaaa atgcggatct tcaccgtggc ccagatggac gataacagta tccagatgaa
2701 gaaggacctg accacgttct tgtaccactt acgcattact gcagaggtgg aggtggtgga
2761 gatgcatgag agcgacatct cggcatacac ctacgagaag acattagtaa tggagcaacg
2821 atctcagatc ctcaaacaga tgcacctcac caagaacgag cgggaacggg agatccagag
2881 catcacagac gagtctcggg ctccattcg gaggaagaat ccagccaacc cccggctccg
2941 cctcaatgtt cccgaagaga cagcgtgtga caatgaggag aagccagagg aggaggtgca
3001 gctgatccat gaccagagtg ctcccagctg ccctagcagc tcgccatctc cagggagga
3061 gcccgagggg gagagggaga cagacccaga ggtgcatctt acctggacca aggataagtc
3121 agtggcagag aagaataaag gccccagtcc cgtctcctcc gagggcatca aggacttctt
3181 cagcatgaag ccggagtggg aaaacttgaa ccagtccaat gtacgcgca tgcacacagc
3241 tgtgcggctg aacgaggtca tcgtgaataa atctcgggat gccaagctag ttttgctcaa
3301 catgccgggg cctccccgca accgcaatgg ggatgaaaac tacatggaat tcttggaggt
3361 cctcactgag caactggacc gggtgatgct ggtccgcggt ggcggccgag aggtcatcac
3421 catctactcc tgaaggccag gacctgccac tccggcccga gcgcgccgg cccgcggccc
3481 ccagagccct cgccgcgcct cccgccgct gtcaccgttt acataagacc cagttgccca
3541 tgccctggcc cctttccttc ccgctgcctg cagcccgag gccttgcccg tcggggctga
3601 cccgcagggc ggcccgtgag gccccttttc tgagcctggc ctcgccccgc cggagc
```

FIG. 10B

Rat KCC2 polypeptide and DNA sequences (Payne, J.A., et al., (1996) J. Biol. Chem. 271 (27), 16245-16252; Gillen, C.M., et al., (1996) J. Biol. Chem. 271 (27), 16237-16244; ACCESSION: U55816)

Rat KCC2 polypeptide (SEQ ID NO:6):

MLNNLTDCEDGDGGANPGDGNPKESSPFINSTDTEKGREYDGRN

MALFEEEMDTSPMVSSLLSGLANYTNLPQGSKEHEEAENNEGGKKKPVQAPRMGTFMG

VYLPCLQNIFGVILFLRLTWVVGIAGIMESFCMVFICCSCTMLTAISMSAIATNGVVP

AGGSYYMISRSLGPEFGGAVGLCFYLGTTFAGAMYILGTIEILLAYLFPAMAIFKAED

ASGEAAAMLNNMRVYGTCVLTCMATVVFVGVKYVNKFALVFLGCVILSILAIYAGVIK

SAFDPPNFPICLLGNRTLSRHGFDVCAKLAWEGNETVTTRLWGLFCSSRLLNATCDEY

FTRNNVTEIQGIPGAASGLIKENLWSSYLTKGVIVERRGMPSVGLADGTPVDMDHPYV

FSDMTSYFTLLVGIYFPSVTGIMAGSNRSGDLRDAQKSIPTGTILAIATTSAVYISSV

VLFGACIEGVVLRDKFGEAVNGNLVVGTLAWPSPWVIVIGSFFSTCGAGLQSLTGAPR

LLQAISRDGIVPFLQVFGHGKANGEPTWALLLTACICEIGILIASLDEVAPILSMFFL

MCYMFVNLACAVQTLLRTPNWRPRFRYYHWTLSFLGMSLCLALMFICSWYYALVAMLI

AGLIYKYIEYRGAEKEWGDGIRGLSLSAARYALLRLEEGPPHTKNWRPQLLVLVRVDQ

DQNVVHPQLLSLTSQLKAGKGLTIVGSVLEGTFLDNHPQAQRAEESIRRLMEAEKVKG

FCQVVISSNLRDGVSHLIQSGGLGGLQHNTVLVGWPRNWRQKEDHQTWRNFIELVRET

TAGHLALLVTKNVSMFPGNPERFSEGSIDVWWIVHDGGMLMLLPFLLRHHKVWRKCKM

RIFTVAQMDDNSIQMKKDLTTFLYHLRITAEVEVVEMHESDISAYTYEKTLVMEQRSQ

ILKQMHLTKNEREREIQSITDESRGSIRRKNPANTRLRLNVPEETACDNEEKPEEEVQ

LIHDQSAPSCPSSSPSPGEEPEGEGETDPEKVHLTWTKDKSAAQKNKGPSPVSSEGIK

DFFSMKPEWENLNQSNVRRMHTAVRLNEVIVNKSRDAKLVLLNMPGPPRNRNGDENYM

EFLEVLTEQLDRVMLVRGGGREVITIYS

Rat KCC2 DNA (SEQ ID NO:5):

```
  1 ccgctccacg gagagcaagc gacagagctc gagcaagcga gcgagcggcg aaggcgggca
 61 gaggggcgcg ggcgaagagg cgcagccatc ccgagcccgg cgccgcgcag ccaccatgct
121 caacaacctg acggactgcg aggacggcga tgggggagcc aacccgggtg acggcaatcc
181 caaggagagc agcccttca tcaacagcac ggacacggag aaggggagag agtatgatgg
241 caggaacatg gccctgtttg aggaggagat ggacaccagc cccatggtat cctccctgct
```

FIG. 11A

```
 301 cagtgggctg gccaactaca ccaacctgcc tcagggaagc aaagagcacg aagaagcaga
 361 aaacaatgag ggcggaaaga agaagccggt gcaggcccca cgcatgggca ccttcatggg
 421 cgtgtacctc ccgtgcctgc agaacatctt tggtgttatc ctctttctgc ggctcacttg
 481 ggtggtggga atcgcaggca tcatggagtc cttctgcatg gtcttcatct gctgctcctg
 541 cacgatgctc acagccattt ccatgagcgc aattgcaacc aatggtgttg tgcctgctgg
 601 tggctcctac tacatgattt ccaggtctct gggcccggag tttggggcg ccgtgggcct
 661 ctgcttctac ctgggcacta cctttgctgg ggctatgtac atcctgggca ccatcgagat
 721 cctgctggct tacctcttcc cagcgatggc catcttcaag gcagaagatg ccagtgggga
 781 ggcagccgcc atgttgaata acatgcgggt gtatggcacc tgtgtgctca cctgcatggc
 841 caccgtagtc tttgtgggcg tcaagtacgt gaacaagttt gccctggtct tcctgggttg
 901 cgtgatcctc tccatcctgg ccatctacgc agggtcatc aagtctgcct tcgatccacc
 961 caatttcccg atttgcctcc tggggaaccg cacgctgtct cgccatggct ttgatgtctg
1021 tgccaagctg gcttgggaag gaatgagac agtgaccaca cggctctggg gcctattctg
1081 ttcctcccgc ctcctcaatg ccacctgtga tgagtacttc acccgaaaca atgtcacaga
1141 gatccagggc attcctggtg ctgcaagtgg cctcatcaaa gagaacctgt ggagttccta
1201 cctgaccaag ggggtgatcg tggagaggcg tgggatgccc tctgtgggcc tggcagatgg
1261 taccccgtt gacatggacc accctatgt cttcagtgat atgacctcct acttcaccct
1321 gcttgttggc atctatttcc cctcagtcac agggatcatg gctggctcga accggtccgg
1381 agacctgcgg gatgcccaga agtctatccc tactgaact atcttggcca ttgctacgac
1441 ctctgctgtc tacatcagct ctgttgttct gttcggagcc tgcatcgaag gggtcgtcct
1501 acgggacaag tttggggaag ctgtgaatgg caatctggtg gtgggcaccc tggcctggcc
1561 ttctccttgg gtcattgtca taggctcttt cttctctacc tgcggagctg gactacagag
1621 cctcacaggg gccccacgcc tgctgcaggc catctcccgg gatggcatag tgcccttcct
1681 gcaggtcttt ggccatggca aagcaacgg agagccaacc tgggcgctgc tgctgactgc
1741 ctgcatctgt gagatcggca tcctcatcgc ctccctggat gaggtcgccc ctatcctttc
1801 catgttcttc ctgatgtgtt acatgtttgt gaacttggct tgcgcggtgc agacactgct
1861 gaggacgccc aactggaggc cacgttccg atattaccac tggaccctct ccttcctggg
1921 catgagcctc tgcctggccc tgatgttcat ttgctcctgg tattatgcgc tggtagctat
1981 gctcatcgct ggcctcatct ataagtacat cgagtcgcgg ggggcagaga aggagtgggg
2041 ggatgggatc cgaggcctgt ctctcagtgc agctcgctat gctctcttgc gtctggagga
2101 aggaccccg catacaaaga actggaggcc ccagctactg gtgctggtgc gtgtggacca
2161 ggaccagaac gtggtgcacc cgcagctgct gtccttgacc tcccagctca aggcagggaa
2221 gggcctgacc attgtgggct ctgtccttga gggcacctt ctggacaacc ccctcaggc
2281 tcagcgggca gaggagtcta tccggcgcct gatggaggct gagaaggtga agggcttctg
2341 ccaggtagtg atctcctcca acctgcgtga cggtgtgtcc cacctgatcc aatccggggg
2401 cctcgggggc ctgcaacaca cactgtgct agtgggctgg cctcgcaact ggcgacagaa
2461 ggaggatcat cagacatgga ggaacttcat cgaactcgtc cgggaaacta cagctggcca
2521 cctcgccctg ctggtcacca agaatgtttc catgttcccc gggaaccctg agcgtttctc
2581 tgagggcagc attgacgtgt ggtggatcgt gcacgacggg ggcatgctca tgctgttgcc
2641 cttcctcctg cgtcaccaca aggtctggag gaaatgcaaa atgcggatct tcaccgtggc
2701 gcagatggat gacaacagca ttcagatgaa gaaagacctg accacgtttc tgtaccactt
2761 acgaattact gcagaggtgg aagtcgtgga gatgcacgag agcgacatct cagcatacac
2821 ctacgagaag acattggtaa tggaacaacg ttctcagatc ctcaaacaga tgcacctcac
2881 caagaacgag cgggaacggg agatccagag catcacagat gaatctcggg gctccattcg
2941 gaggaagaat ccagccaaca ctcggctccg cctcaatgtt cccgaagaga cagcttgtga
3001 caacgaggag aagccagaag aggaggtgca gctgatccat gaccagagtg ctcccagctg
3061 ccctagcagc tcgccgtctc aggggagga gctgaggggg aggggggaga cagacccaga
3121 gaaggtgcat ctcacctgga ccaaggataa gtcagcggct cagaagaaca aaggccccag
3181 tccgtctcc tcggagggga tcaaggactt cttcagcatg aagccggagt gggaaaactt
3241 gaaccagtcc aacgtgcggc gcatgcacac agctgtgcgg ctgaacgagg tcatcgtgaa
3301 taaatcccgg gatgccaagt ggtgttgct caacatgccc gggcctcccc gcaaccgcaa
3361 tggagatgaa aactacatgg aattcctgga ggtcctcact gagcaactgg accggtgat
3421 gctggtccgc ggtggtggcc gagaggtcat accatctac tcctgaaggc caggacctgc
3481 cactccggcc cgagcgagcc cggccgcgcg ccccggagcc ctcgccgcgc ctcccgcg
3541 ctgtcaccgt ttacataaga ccccgttgcc cgtgcctgg ccctcttccc tcccgctgcc
3601 tgcggcccgg aggccttgcc cgtcgggct gacccggagg cggccccgtg ggcccttttt
3661 ctgagcccgg cctcgccctg ccggagtaga cgttgcaata aaggtggcga ggcggcgtgg
3721 agaggagcgg aaccgtggtc ccgggccggg gagccccgag cccgtccctc cccacgcccc
```

FIG. 11B

```
3781 gccgcgctcc ccccggaccc tggtcgctga gcccgggcgc cgctcggctg cgctatacat
3841 agtgtacagg agacatcgag tgtattttta atgtccccat atttctgtaa actagaaacg
3901 caacggactc ctcgccacgg ccgcgctctc cccgctgcgg gcgcccagga aggcggagac
3961 ccgggaagcc agggttccct gcgctcccga gctgagagcc aagtgcttta aggccggcgc
4021 tctcctttcc ctttcctgtc cacggcccgg gcttccctct cttccctcca gttcttggcg
4081 aacacaggtg aagccctgcc cggtgccttc gtggaggagc aggcgtctct cctctgttgg
4141 cttgccgcct gctcccctg tcccgtggct cctcgccaaa gactgaattt gtgggagctgg
4201 agggcacacc ctccccactt tccttcctgg gacaggtgag gggccaatgc cagtctaggg
4261 gccgactcac aggaggcctc gcgcagcctc ttggtcccca ctctgcaagt cctgcctggg
4321 gacccagccc cctggtggt tctgggcgg agctttgctg cctagcagca agtccttagt
4381 tactgtctcc agataccagg acctggagta gggaatggag tcatatgggt tcagttgttc
4441 ctggcgcttc tctgccccct gctcccctc tccccctctc gtaggacaca aggactttgg
4501 cttttcttaac tcatccttgg cgcttccgct ccaccacgcc cacctgtggg gaggagccct
4561 cagccctaga gaggcgtttg gctggttccc ttcccccagg gcacgttact aagaggacag
4621 gcactgcatg ctcctttaag cgccctctgg gactgggtac agtgcctcca gccccaggc
4681 cctggtctgc gcacctagtt agacatcatt gcccactcca gggccagggc cactagctga
4741 cctcaccacc tttttccttg agcccaaggc agagagagct gcagctggtg ccatctagac
4801 aggctcaagt gtggccagtg gcagggctcg agggccactg ccctgttgct tggctcagga
4861 cctctctgag atttgatggg gactggatat tcttccaggt agtagccatc aagtcggaag
4921 tgttggaccc aggacctgac attccttcaa gactgccctc ccttgctgtg gttttgcctt
4981 ttggggcaag agaggggctg ggcaaacggg gaggaggcag tatcaacacc gattagggaa
5041 ccaaagttgc actacctggg cccagcctct ggttggcaag agcaaagttt ctgttgatga
5101 aaacaaacag cccacaacaa cacccccccc cccgttttct gtgctccatg tgcaatattt
5161 gttatgaacc ttgtgtcgtt caagtcacct ttataatcac tgtagctaga tgttccatgt
5221 ccatccaggt gactttactc tgagtgcaat atttcaatag cctggtagtg agaagagtgt
5281 tgcttttgtt tcagccgacc tatgtgcagg gcaatgcaat gcagtccaaa acccttgtaa
5341 ataggagagg ttgcaagcca aatcaagagt atttatcgtt attactatta ttattaggcc
5401 tgcctttaat tttagtgttt cggtatttcg catcctgcct cggtattgat cgtgtgttct
5461 ctgtgccaat atgcaaagga gaggatcagt tctttccttt actgttgaat gctcccattt
5521 actgctttaa ggcttttact gtgttcattt tttagatacc tgtctg
```

FIG. 11C

SEQUENCE LISTING

<160> NUMBER OF SEQ ID NOS: 8

<210> SEQ ID NO 1
<211> LENGTH: 5907
<212> TYPE: DNA
<213> ORGANISM: Homo sapiens
<220> FEATURE:
<221> NAME/KEY: CDS
<222> LOCATION: (1)..(3351)

<400> SEQUENCE: 1

```
atg ccc aac aac ctg acg gac tgc gag gac ggc gat ggg gga gcc aac      48
Met Pro Asn Asn Leu Thr Asp Cys Glu Asp Gly Asp Gly Gly Ala Asn
 1               5                  10                  15 ccg ggt gat ggc aac ccc aag gaa agc agt ccc ttc atc aac agc acc      96
Pro Gly Asp Gly Asn Pro Lys Glu Ser Ser Pro Phe Ile Asn Ser Thr
             20                  25                  30 gac aca gag aag gga aag gag tat gat ggc aag aac atg gcc ttg ttt     144
Asp Thr Glu Lys Gly Lys Glu Tyr Asp Gly Lys Asn Met Ala Leu Phe
         35                  40                  45 gag gag gag atg gac acc agc cct atg gtg tcc tcc ttg ctc agt ggc     192
Glu Glu Glu Met Asp Thr Ser Pro Met Val Ser Ser Leu Leu Ser Gly
     50                  55                  60 ctg gcc aac tac acc aac ctg ccc cag gga agt agg gag cat gaa gag     240
Leu Ala Asn Tyr Thr Asn Leu Pro Gln Gly Ser Arg Glu His Glu Glu
 65                  70                  75                  80 gca gaa aac aat gag ggt gga aaa aag aag ccg gtg cag gcc cca cgc     288
Ala Glu Asn Asn Glu Gly Gly Lys Lys Lys Pro Val Gln Ala Pro Arg
                 85                  90                  95 atg ggc acc ttc atg ggc gtg tac ctg ccg tgc ctg cag aac atc ttt     336
Met Gly Thr Phe Met Gly Val Tyr Leu Pro Cys Leu Gln Asn Ile Phe
            100                 105                 110 ggc gtc atc ctc ttc ctg cgg ctc acc tgg gtg gtg ggc att gca ggc     384
Gly Val Ile Leu Phe Leu Arg Leu Thr Trp Val Val Gly Ile Ala Gly
        115                 120                 125 atc atg gag tcc ttc tgc atg gtg ttc atc tgc tgc tcc tgt acg atg     432
Ile Met Glu Ser Phe Cys Met Val Phe Ile Cys Cys Ser Cys Thr Met
    130                 135                 140 ctc acg gcc atc tcc atg agt gca att gca acg aat ggt gtt gtg cct     480
Leu Thr Ala Ile Ser Met Ser Ala Ile Ala Thr Asn Gly Val Val Pro
145                 150                 155                 160 gct ggt ggc tcc tac tac atg att tcc agg tct ctg ggc cca gag ttt     528
Ala Gly Gly Ser Tyr Tyr Met Ile Ser Arg Ser Leu Gly Pro Glu Phe
                165                 170                 175 ggg ggt gcc gtg ggc ctc tgc ttc tac ctg gga act acc ttt gca gga     576
Gly Gly Ala Val Gly Leu Cys Phe Tyr Leu Gly Thr Thr Phe Ala Gly
            180                 185                 190 gcc atg tac atc ctg ggc acc atc gaa atc ctg ctg gct tac ctc ttc     624
Ala Met Tyr Ile Leu Gly Thr Ile Glu Ile Leu Leu Ala Tyr Leu Phe
        195                 200                 205
```

```
cca gcc atg gcc atc ttc aag gca gaa gat gcc agt ggg gag gca gca     672
Pro Ala Met Ala Ile Phe Lys Ala Glu Asp Ala Ser Gly Glu Ala Ala
210                 215                 220 gcc atg ctg aac aac atg cgt gtt tac ggc acc tgt gtg ctc acc tgc     720
Ala Met Leu Asn Asn Met Arg Val Tyr Gly Thr Cys Val Leu Thr Cys
225                 230                 235                 240 atg gcc act gtg gtg ttt gtg ggt gtc aag tat gtc aac aag ttt gcc     768
Met Ala Thr Val Val Phe Val Gly Val Lys Tyr Val Asn Lys Phe Ala
            245                 250                 255 ctt gtc ttc ctg ggt tgt gtc atc ctc tcc atc ctg gcc atc tat gct     816
Leu Val Phe Leu Gly Cys Val Ile Leu Ser Ile Leu Ala Ile Tyr Ala
        260                 265                 270 ggg gtc atc aag tct gcc ttc gac cca ccc aac ttc ccg atc tgc ctc     864
Gly Val Ile Lys Ser Ala Phe Asp Pro Pro Asn Phe Pro Ile Cys Leu
    275                 280                 285 ctg ggt aac cgc acg ctg tct cgc cat ggc ttt gat gtc tgt gcc aag     912
Leu Gly Asn Arg Thr Leu Ser Arg His Gly Phe Asp Val Cys Ala Lys
290                 295                 300 ctg gct tgg gaa gga aat gag acg gtg acc aca cgg cta tgg ggc ctt     960
Leu Ala Trp Glu Gly Asn Glu Thr Val Thr Thr Arg Leu Trp Gly Leu
305                 310                 315                 320 ttc tgc tcc tct cgc ttc ctc aac gcc acc tgt gat gaa tac ttc acc    1008
Phe Cys Ser Ser Arg Phe Leu Asn Ala Thr Cys Asp Glu Tyr Phe Thr
            325                 330                 335 cga aac aat gtc aca gag atc cag ggc atc cct ggt gct gcc agt ggc    1056
Arg Asn Asn Val Thr Glu Ile Gln Gly Ile Pro Gly Ala Ala Ser Gly
        340                 345                 350 ctc atc aaa gag aac ctc tgg agc tcc tac ctg acc aag ggc gtg att    1104
Leu Ile Lys Glu Asn Leu Trp Ser Ser Tyr Leu Thr Lys Gly Val Ile
    355                 360                 365 gtg gag agg agt ggg atg acc tcg gtg ggc ctg gcc gat ggc act cct    1152
Val Glu Arg Ser Gly Met Thr Ser Val Gly Leu Ala Asp Gly Thr Pro
370                 375                 380 atc gac atg gac cac cct tat gtc ttc agt gat atg acc tcc tac ttc    1200
Ile Asp Met Asp His Pro Tyr Val Phe Ser Asp Met Thr Ser Tyr Phe
385                 390                 395                 400 acc ctg ctg gtt ggc atc tac ttc ccc tca gtc aca ggg atc atg gct    1248
Thr Leu Leu Val Gly Ile Tyr Phe Pro Ser Val Thr Gly Ile Met Ala
            405                 410                 415 ggt tct aac cgc tct ggg gac ctg agg gat gcc cag aag tca atc ccc    1296
Gly Ser Asn Arg Ser Gly Asp Leu Arg Asp Ala Gln Lys Ser Ile Pro
        420                 425                 430 act ggc acc atc ctg gcc atc gcc acc acc tct gct gtc tac atc agc    1344
Thr Gly Thr Ile Leu Ala Ile Ala Thr Thr Ser Ala Val Tyr Ile Ser
    435                 440                 445 tcc gtt gtt ctg ttt ggg gcc tgc att gag ggg gtc gtc ctg cgg gac    1392
Ser Val Val Leu Phe Gly Ala Cys Ile Glu Gly Val Val Leu Arg Asp
450                 455                 460 aag ttt ggc gaa gct gtg aat ggc aac ctc gtg gtg ggc act ctg gcc    1440
Lys Phe Gly Glu Ala Val Asn Gly Asn Leu Val Val Gly Thr Leu Ala
465                 470                 475                 480 tgg cca tct cca tgg gta att gtc atc gga tcc ttc ttc tcc acc tgt    1488
Trp Pro Ser Pro Trp Val Ile Val Ile Gly Ser Phe Phe Ser Thr Cys
            485                 490                 495 ggg gct ggg ctg cag agc ctc acg ggg gcc cca cgc ctg ctg cag gcc    1536
Gly Ala Gly Leu Gln Ser Leu Thr Gly Ala Pro Arg Leu Leu Gln Ala
        500                 505                 510 atc tcg agg gat ggc att gtg ccc ttc ctg cag gtc ttt ggc cat ggc    1584
Ile Ser Arg Asp Gly Ile Val Pro Phe Leu Gln Val Phe Gly His Gly
    515                 520                 525
```

| | | |
|---|---|---|
| aag gcc aat gga gag ccg acc tgg gcc ctg ctc ctg act gcc tgc atc<br>Lys Ala Asn Gly Glu Pro Thr Trp Ala Leu Leu Leu Thr Ala Cys Ile<br>530 535 540 | | 1632 |
| tgc gag att ggc atc ctc att gca tcc ctc gac gag gtg gcc ccc atc<br>Cys Glu Ile Gly Ile Leu Ile Ala Ser Leu Asp Glu Val Ala Pro Ile<br>545 550 555 560 | | 1680 |
| ctc tct atg ttc ttc ctg atg tgc tac atg ttt gtg aat ctg gcc tgt<br>Leu Ser Met Phe Phe Leu Met Cys Tyr Met Phe Val Asn Leu Ala Cys<br>565 570 575 | | 1728 |
| gca gtg cag acg ctg ctg agg aca ccc aac tgg agg cca cgc ttt cga<br>Ala Val Gln Thr Leu Leu Arg Thr Pro Asn Trp Arg Pro Arg Phe Arg<br>580 585 590 | | 1776 |
| tat tac cac tgg acc ctc tcc ttc ctg ggc atg agc ctc tgc ctg gcc<br>Tyr Tyr His Trp Thr Leu Ser Phe Leu Gly Met Ser Leu Cys Leu Ala<br>595 600 605 | | 1824 |
| ctc atg ttc atc tgc tcc tgg tat tat gca ctg gta gcc atg ctc att<br>Leu Met Phe Ile Cys Ser Trp Tyr Tyr Ala Leu Val Ala Met Leu Ile<br>610 615 620 | | 1872 |
| gct gga ctc atc tac aag tac att gag tac cgt ggg gca gag aag gag<br>Ala Gly Leu Ile Tyr Lys Tyr Ile Glu Tyr Arg Gly Ala Glu Lys Glu<br>625 630 635 640 | | 1920 |
| tgg ggc gat ggg ata cga ggt ctg tct ctc agt gcg gct cgc tat gcc<br>Trp Gly Asp Gly Ile Arg Gly Leu Ser Leu Ser Ala Ala Arg Tyr Ala<br>645 650 655 | | 1968 |
| ctc tta cgc ctg gag gaa ggg ccc cca cac acc aag aac tgg agg cca<br>Leu Leu Arg Leu Glu Glu Gly Pro Pro His Thr Lys Asn Trp Arg Pro<br>660 665 670 | | 2016 |
| cag ctg ctg gtg ctg gtg cgt gtg gac caa gac cag aat gtg gtg cac<br>Gln Leu Leu Val Leu Val Arg Val Asp Gln Asp Gln Asn Val Val His<br>675 680 685 | | 2064 |
| ccc cag ctg ctc tca ctg acc tcc cag ctg aag gca ggg aag ggc ctg<br>Pro Gln Leu Leu Ser Leu Thr Ser Gln Leu Lys Ala Gly Lys Gly Leu<br>690 695 700 | | 2112 |
| acc atc gtg ggc tct gtc ctt gag ggc acc ttt ctg gaa aat cat cca<br>Thr Ile Val Gly Ser Val Leu Glu Gly Thr Phe Leu Glu Asn His Pro<br>705 710 715 720 | | 2160 |
| cag gcc cag cgg gca gaa gag tct atc agg cgc ctg atg gag gca gag<br>Gln Ala Gln Arg Ala Glu Glu Ser Ile Arg Arg Leu Met Glu Ala Glu<br>725 730 735 | | 2208 |
| aag gtg aag ggc ttc tgc cag gtg gtg atc tcc tcc aac ttg cgt gat<br>Lys Val Lys Gly Phe Cys Gln Val Val Ile Ser Ser Asn Leu Arg Asp<br>740 745 750 | | 2256 |
| ggc gtg tcc cat ctg atc cag tcc ggg ggc ctc ggg ggg ctg cag cac<br>Gly Val Ser His Leu Ile Gln Ser Gly Gly Leu Gly Gly Leu Gln His<br>755 760 765 | | 2304 |
| aac act gtg ctt gtt ggc tgg ccc cgc aac tgg cgc cag aag gaa gat<br>Asn Thr Val Leu Val Gly Trp Pro Arg Asn Trp Arg Gln Lys Glu Asp<br>770 775 780 | | 2352 |
| cat cag acg tgg agg aac ttc att gag ctg gtc cgg gaa acc aca gct<br>His Gln Thr Trp Arg Asn Phe Ile Glu Leu Val Arg Glu Thr Thr Ala<br>785 790 795 800 | | 2400 |
| ggc cac tta gcc ctg ctg gtc acc aag aac gtt tcc atg ttt cct ggg<br>Gly His Leu Ala Leu Leu Val Thr Lys Asn Val Ser Met Phe Pro Gly<br>805 810 815 | | 2448 |
| aac cct gag cgc ttc tct gag ggc agc atc gac gtt tgg tgg att gtg<br>Asn Pro Glu Arg Phe Ser Glu Gly Ser Ile Asp Val Trp Trp Ile Val<br>820 825 830 | | 2496 |
| cac gat gga ggc atg ctc atg ctg ctg ccc ttc ctg ctg cgg cac cac<br>His Asp Gly Gly Met Leu Met Leu Leu Pro Phe Leu Leu Arg His His<br>835 840 845 | | 2544 |

| | |
|---|---:|
| aag gtc tgg cgg aag tgc aag atg cgt atc ttc act gtg gcc cag atg<br>Lys Val Trp Arg Lys Cys Lys Met Arg Ile Phe Thr Val Ala Gln Met<br>850                      855                    860 | 2592 |
| gat gac aat agc atc cag atg aag aag gat ctg acc aca ttt ctg tat<br>Asp Asp Asn Ser Ile Gln Met Lys Lys Asp Leu Thr Thr Phe Leu Tyr<br>865                      870                    875                    880 | 2640 |
| cat tta cgc atc act gcg gag gtc gag gtg gtg gag atg cat gag agc<br>His Leu Arg Ile Thr Ala Glu Val Glu Val Val Glu Met His Glu Ser<br>                    885                    890                    895 | 2688 |
| gac atc tca gct tac acc tat gag aag acg ttg gtg atg gag cag cgt<br>Asp Ile Ser Ala Tyr Thr Tyr Glu Lys Thr Leu Val Met Glu Gln Arg<br>900                      905                              910 | 2736 |
| tcc cag atc ctc aaa cag atg cat tta acc aag aat gag cgg gag cgg<br>Ser Gln Ile Leu Lys Gln Met His Leu Thr Lys Asn Glu Arg Glu Arg<br>                    915                    920                    925 | 2784 |
| gag atc cag agt atc aca gat gag tca cga ggc tca atc cgg aga aag<br>Glu Ile Gln Ser Ile Thr Asp Glu Ser Arg Gly Ser Ile Arg Arg Lys<br>930                      935                              940 | 2832 |
| aat cca gcc aac acg cgg ctc cgc ctg aac gtc cca gaa gag acg gct<br>Asn Pro Ala Asn Thr Arg Leu Arg Leu Asn Val Pro Glu Glu Thr Ala<br>945                      950                    955                    960 | 2880 |
| ggt gac agt gaa gag aag cca gag gag gag gtg cag ctg atc cac gat<br>Gly Asp Ser Glu Glu Lys Pro Glu Glu Glu Val Gln Leu Ile His Asp<br>                    965                    970                    975 | 2928 |
| cag agt gct ccc agc tgc ccc agc agc tcc ccg tcc cca ggg gag gag<br>Gln Ser Ala Pro Ser Cys Pro Ser Ser Ser Pro Ser Pro Gly Glu Glu<br>980                      985                              990 | 2976 |
| cct gag ggg gaa ggg gag aca gat ccg gag aag gtg cat ctc acc tgg<br>Pro Glu Gly Glu Gly Glu Thr Asp Pro Glu Lys Val His Leu Thr Trp<br>                    995                    1000                    1005 | 3024 |
| acc aag gac aag tcg gtg gca gag aag aat aag ggc ccc agt cct<br>Thr Lys Asp Lys Ser Val Ala Glu Lys Asn Lys Gly Pro Ser Pro<br>1010                      1015                    1020 | 3069 |
| gtc tcc tct gag ggc atc aag gac ttc ttc agc atg aag ccg gag<br>Val Ser Ser Glu Gly Ile Lys Asp Phe Phe Ser Met Lys Pro Glu<br>1025                      1030                    1035 | 3114 |
| tgg gag aac ttg aac cag tcc aac gtg cgg cgc atg cac acg gcc<br>Trp Glu Asn Leu Asn Gln Ser Asn Val Arg Arg Met His Thr Ala<br>1040                      1045                    1050 | 3159 |
| gtg cgg ctg aac gag gtc atc gtg aag aaa tcc cgg gac gcc aag<br>Val Arg Leu Asn Glu Val Ile Val Lys Lys Ser Arg Asp Ala Lys<br>1055                      1060                    1065 | 3204 |
| ctt gtt ttg ctc aac atg cct ggg cct ccc cgc aac cgc aat ggt<br>Leu Val Leu Leu Asn Met Pro Gly Pro Pro Arg Asn Arg Asn Gly<br>1070                      1075                    1080 | 3249 |
| gat gaa aac tac atg gag ttt ctc gag gtc ctc aca gag cac ctg<br>Asp Glu Asn Tyr Met Glu Phe Leu Glu Val Leu Thr Glu His Leu<br>1085                      1090                    1095 | 3294 |
| gac cgg gtg atg ctg gtc cgc ggt ggt ggc cga gag gtc atc acc<br>Asp Arg Val Met Leu Val Arg Gly Gly Gly Arg Glu Val Ile Thr<br>1100                      1105                    1110 | 3339 |
| atc tac tcc tga gaaccaggtc ctgccacccg ggcccgagcg cgcccggccc<br>Ile Tyr Ser<br>1115 | 3391 |
| gcggctccgg agccctcgcc gcgcccccg ccgctgtcac cgtttacata cagaccctgt | 3451 |
| gcccgtgtcc tggcccctta ccccgctgcc tgaagcccgg aggccacgcc tgttggggct | 3511 |
| gattcggaga gggcgccccg ccgcgcagag accagagctc ctcagtgcca gtttggcccc | 3571 |
| tgggtcttcg ctgcccttt tctaagcccg gcctcgtctc gccggaggag acgctgcaat | 3631 |

```
aaaggttggg agaaggcgcg gaaaggagag gagctggggc cttggggacc cccaggtagt    3691
ccatgcggcc cattcctccc cttcccactc ccgccgcggt cctcgctctg cgctcctccg    3751
gcgctgctcc ctggctcccg gcggcccgga ggcccgcggg gtgggaaggc cgcgcttgcc    3811
gtctccgccg ccccttctcg ccgagccgtg gggcgcgggc ggccgagcct atacatagtg    3871
tacaggagac atcgcgtgta tttttaacgt ccccatattt atgtgactag aagcgcaaca    3931
gacttctcgc catagtcgag ctctcccgct gggggcactg cggggaggcg aggcctcggg    3991
aagctgaatt ttccttgacg tccaagagtt tgagagcgaa agtgctttag gcccaggcgg    4051
gggtcgtggc ctcgttccct cgacacctcc gtcctgctct cgcctcttcg cccttccgc    4111
gcgcccttgg cttcccaccc tcctctccag tccttttccg agatgaggtg agacaagggt    4171
ccaactttc ctggattcgc ctcccagcgg acgtgagctt ccactgcggc tgcagagacg    4231
cgagcaacct cttctcatcg gctcttatgc aagttggggc caggataggg gagggtgct    4291
cctcaagagg aagaaaccga gaggcccgcg ccccaccgag gaagcccgc ccggtgcct    4351
tcgctgggga gcaggcgtct ctcctcagtc ggcttgtcgc ctgctccccg tatcccatgg    4411
ctcctcgcca aagactgaaa ttgtggagct ggagggcgcc ccctcccgg agtttcctcc    4471
ctgggacaag tgagggagga gggggccgat tctggtttag gggccggacc cactgagagg    4531
ccccagagcc gccgtgatg ttcctccccc gtccccatct ggcagctcct gtctcgcctg    4591
agggacccag ccgccttctc cgtgctctgg ggccgggcct cgctgcttag cagcggcctc    4651
tagctccgtc tcccggggac ctgggcctga ggaggctg gagtcagcac gcgctttgtc    4711
cttagcgcct gtctgctctc ctctaactag gacccagggc ctttggcttc cccagctcat    4771
ccttggcccc tccgctccac cagcctggtc tgaggcgtgc tctgtcctta gagaaggcgc    4831
ggtggccggg ttcccttccc ctagggcaca ttactaaggg ggtcaggcac tgcatgctcg    4891
ttccagcacc atctgggact gggtacagta cctccagccc cagggccctg acctgcgcac    4951
ctagcttgac atctcacgca cctcccagag ctggcgccac tgagtaatcc ggacctcacc    5011
acctctttc ctttgagccc aaggcagagc tagagctgga gctggcgcca cccagacagc    5071
gtcaggtgtg gctggggtag gtttggaggt ctgccagtta cgccaagtcc cctctgagat    5131
tcgatcaggg gactggatag attctttcag gtactcaatc aggaagctgg aggtgttaga    5191
caccagcccc ctgcatcctt cagtagacct ccctctgaac accacagcca ggtcctgcct    5251
tctgggggcc tgaatattcc agagctgatg tgatgggctg tgcagaaggg ggctgtatca    5311
acatcaatta gggaaccaaa gttgcactat ctgggcccag attgtctggt tggcaagagc    5371
aaagtttccg ttgatgaaac agacatccca caacaaaaac ccaagttttc tgtgctacat    5431
gtgcaatatt tgttatgaat gttatcacaa gtcattcatc aagttatctt tataatcact    5491
gtagttagat gtttcatgtc cattcaagtg actttattc tgagtgcaat atttcaatag    5551
ccttgtagtg ataactagtg ttgctttttgt ttagatgatc tatgtgcagg gcaatgcaat    5611
gaagttgaaa cccttggta ataggagagg ttgcaaacca atcaagagt atttattact    5671
attactgcta ttattattag gcctgccttt aatttcagt gtaagtgttc agtatgccgc    5731
atcctgcctc agtattgatc ttgtgttctt tgtgccaata tgaaaggag agggttggtt    5791
cttttccttta ttgttgaatg ctcccattta atgctttatg gcttttactg tattactttt    5851
ttagactccc gtctgcacaa aatgcaataa aaataatttt attataaaaa aaaaaa        5907
```

<210> SEQ ID NO 2
<211> LENGTH: 1116

<212> TYPE: PRT
<213> ORGANISM: Homo sapiens

<400> SEQUENCE: 2

```
Met Pro Asn Asn Leu Thr Asp Cys Glu Asp Gly Asp Gly Ala Asn
1               5                   10                  15

Pro Gly Asp Gly Asn Pro Lys Glu Ser Ser Pro Phe Ile Asn Ser Thr
                20                  25                  30

Asp Thr Glu Lys Gly Lys Glu Tyr Asp Gly Lys Asn Met Ala Leu Phe
            35                  40                  45

Glu Glu Glu Met Asp Thr Ser Pro Met Val Ser Ser Leu Leu Ser Gly
        50                  55                  60

Leu Ala Asn Tyr Thr Asn Leu Pro Gln Gly Ser Arg Glu His Glu Glu
65                  70                  75                  80

Ala Glu Asn Asn Glu Gly Gly Lys Lys Lys Pro Val Gln Ala Pro Arg
                85                  90                  95

Met Gly Thr Phe Met Gly Val Tyr Leu Pro Cys Leu Gln Asn Ile Phe
            100                 105                 110

Gly Val Ile Leu Phe Leu Arg Leu Thr Trp Val Val Gly Ile Ala Gly
        115                 120                 125

Ile Met Glu Ser Phe Cys Met Val Phe Ile Cys Cys Ser Cys Thr Met
130                 135                 140

Leu Thr Ala Ile Ser Met Ser Ala Ile Ala Thr Asn Gly Val Val Pro
145                 150                 155                 160

Ala Gly Gly Ser Tyr Tyr Met Ile Ser Arg Ser Leu Gly Pro Glu Phe
                165                 170                 175

Gly Gly Ala Val Gly Leu Cys Phe Tyr Leu Gly Thr Thr Phe Ala Gly
            180                 185                 190

Ala Met Tyr Ile Leu Gly Thr Ile Glu Ile Leu Leu Ala Tyr Leu Phe
        195                 200                 205

Pro Ala Met Ala Ile Phe Lys Ala Glu Asp Ala Ser Gly Glu Ala Ala
210                 215                 220

Ala Met Leu Asn Asn Met Arg Val Tyr Gly Thr Cys Val Leu Thr Cys
225                 230                 235                 240

Met Ala Thr Val Val Phe Val Gly Val Lys Tyr Val Asn Lys Phe Ala
                245                 250                 255

Leu Val Phe Leu Gly Cys Val Ile Leu Ser Ile Leu Ala Ile Tyr Ala
            260                 265                 270

Gly Val Ile Lys Ser Ala Phe Asp Pro Pro Asn Phe Pro Ile Cys Leu
        275                 280                 285

Leu Gly Asn Arg Thr Leu Ser Arg His Gly Phe Asp Val Cys Ala Lys
290                 295                 300

Leu Ala Trp Glu Gly Asn Glu Thr Val Thr Thr Arg Leu Trp Gly Leu
305                 310                 315                 320

Phe Cys Ser Ser Arg Phe Leu Asn Ala Thr Cys Asp Glu Tyr Phe Thr
                325                 330                 335

Arg Asn Asn Val Thr Glu Ile Gln Gly Ile Pro Gly Ala Ala Ser Gly
            340                 345                 350

Leu Ile Lys Glu Asn Leu Trp Ser Ser Tyr Leu Thr Lys Gly Val Ile
        355                 360                 365

Val Glu Arg Ser Gly Met Thr Ser Val Gly Leu Ala Asp Gly Thr Pro
370                 375                 380

Ile Asp Met Asp His Pro Tyr Val Phe Ser Asp Met Thr Ser Tyr Phe
385                 390                 395                 400
```

-continued

```
Thr Leu Leu Val Gly Ile Tyr Phe Pro Ser Val Gly Ile Met Ala
            405                 410                 415

Gly Ser Asn Arg Ser Gly Asp Leu Arg Asp Ala Gln Lys Ser Ile Pro
        420                 425                 430

Thr Gly Thr Ile Leu Ala Ile Ala Thr Thr Ser Ala Val Tyr Ile Ser
            435                 440                 445

Ser Val Val Leu Phe Gly Ala Cys Ile Glu Gly Val Val Leu Arg Asp
        450                 455                 460

Lys Phe Gly Glu Ala Val Asn Gly Asn Leu Val Val Gly Thr Leu Ala
465                 470                 475                 480

Trp Pro Ser Pro Trp Val Ile Val Ile Gly Ser Phe Phe Ser Thr Cys
                485                 490                 495

Gly Ala Gly Leu Gln Ser Leu Thr Gly Ala Pro Arg Leu Leu Gln Ala
            500                 505                 510

Ile Ser Arg Asp Gly Ile Val Pro Phe Leu Gln Val Phe Gly His Gly
        515                 520                 525

Lys Ala Asn Gly Glu Pro Thr Trp Ala Leu Leu Leu Thr Ala Cys Ile
        530                 535                 540

Cys Glu Ile Gly Ile Leu Ile Ala Ser Leu Asp Glu Val Ala Pro Ile
545                 550                 555                 560

Leu Ser Met Phe Phe Leu Met Cys Tyr Met Phe Val Asn Leu Ala Cys
                565                 570                 575

Ala Val Gln Thr Leu Leu Arg Thr Pro Asn Trp Arg Pro Arg Phe Arg
            580                 585                 590

Tyr Tyr His Trp Thr Leu Ser Phe Leu Gly Met Ser Leu Cys Leu Ala
        595                 600                 605

Leu Met Phe Ile Cys Ser Trp Tyr Tyr Ala Leu Val Ala Met Leu Ile
        610                 615                 620

Ala Gly Leu Ile Tyr Lys Tyr Ile Glu Tyr Arg Gly Ala Glu Lys Glu
625                 630                 635                 640

Trp Gly Asp Gly Ile Arg Gly Leu Ser Leu Ser Ala Ala Arg Tyr Ala
                645                 650                 655

Leu Leu Arg Leu Glu Glu Gly Pro Pro His Thr Lys Asn Trp Arg Pro
            660                 665                 670

Gln Leu Leu Val Leu Val Arg Val Asp Gln Asp Gln Asn Val Val His
        675                 680                 685

Pro Gln Leu Leu Ser Leu Thr Ser Gln Leu Lys Ala Gly Lys Gly Leu
        690                 695                 700

Thr Ile Val Gly Ser Val Leu Glu Gly Thr Phe Leu Glu Asn His Pro
705                 710                 715                 720

Gln Ala Gln Arg Ala Glu Glu Ser Ile Arg Arg Leu Met Glu Ala Glu
                725                 730                 735

Lys Val Lys Gly Phe Cys Gln Val Val Ile Ser Ser Asn Leu Arg Asp
            740                 745                 750

Gly Val Ser His Leu Ile Gln Ser Gly Gly Leu Gly Gly Leu Gln His
        755                 760                 765

Asn Thr Val Leu Val Gly Trp Pro Arg Asn Trp Arg Gln Lys Glu Asp
        770                 775                 780

His Gln Thr Trp Arg Asn Phe Ile Glu Leu Val Arg Glu Thr Thr Ala
785                 790                 795                 800

Gly His Leu Ala Leu Leu Val Thr Lys Asn Val Ser Met Phe Pro Gly
                805                 810                 815

Asn Pro Glu Arg Phe Ser Glu Gly Ser Ile Asp Val Trp Trp Ile Val
            820                 825                 830
```

```
His Asp Gly Gly Met Leu Met Leu Leu Pro Phe Leu Leu Arg His His
        835                 840                 845

Lys Val Trp Arg Lys Cys Lys Met Arg Ile Phe Thr Val Ala Gln Met
850                 855                 860

Asp Asp Asn Ser Ile Gln Met Lys Lys Asp Leu Thr Thr Phe Leu Tyr
865                 870                 875                 880

His Leu Arg Ile Thr Ala Glu Val Glu Val Val Glu Met His Glu Ser
                885                 890                 895

Asp Ile Ser Ala Tyr Thr Tyr Glu Lys Thr Leu Val Met Glu Gln Arg
            900                 905                 910

Ser Gln Ile Leu Lys Gln Met His Leu Thr Lys Asn Glu Arg Glu Arg
        915                 920                 925

Glu Ile Gln Ser Ile Thr Asp Glu Ser Arg Gly Ser Ile Arg Arg Lys
    930                 935                 940

Asn Pro Ala Asn Thr Arg Leu Arg Leu Asn Val Pro Glu Glu Thr Ala
945                 950                 955                 960

Gly Asp Ser Glu Glu Lys Pro Glu Glu Val Gln Leu Ile His Asp
                965                 970                 975

Gln Ser Ala Pro Ser Cys Pro Ser Ser Ser Pro Ser Pro Gly Glu
            980                 985                 990

Pro Glu Gly Glu Gly Glu Thr Asp Pro Glu Lys Val His Leu Thr Trp
        995                 1000                1005

Thr Lys Asp Lys Ser Val Ala Glu Lys Asn Lys Gly Pro Ser Pro
    1010                1015                1020

Val Ser Ser Glu Gly Ile Lys Asp Phe Phe Ser Met Lys Pro Glu
    1025                1030                1035

Trp Glu Asn Leu Asn Gln Ser Asn Val Arg Arg Met His Thr Ala
    1040                1045                1050

Val Arg Leu Asn Glu Val Ile Val Lys Lys Ser Arg Asp Ala Lys
    1055                1060                1065

Leu Val Leu Leu Asn Met Pro Gly Pro Pro Arg Asn Arg Asn Gly
    1070                1075                1080

Asp Glu Asn Tyr Met Glu Phe Leu Glu Val Leu Thr Glu His Leu
    1085                1090                1095

Asp Arg Val Met Leu Val Arg Gly Gly Gly Arg Glu Val Ile Thr
    1100                1105                1110

Ile Tyr Ser
    1115

<210> SEQ ID NO 3
<211> LENGTH: 3656
<212> TYPE: DNA
<213> ORGANISM: Mus musculus
<220> FEATURE:
<221> NAME/KEY: CDS
<222> LOCATION: (86)..(3433)

<400> SEQUENCE: 3
gagcaagcga gcgagcggag aaggcgggca gaggggcgcg ggcgaagcgg cgcagccatc      60
ccgagcccgg cgccgcgcag ccacc atg ctc aac aac ctg acg gac tgc gag     112
                              Met Leu Asn Asn Leu Thr Asp Cys Glu
                              1               5 gac ggc gat ggg gga gcc aac ccc ggt gat ggc aac ccc aaa gag agc      160
Asp Gly Asp Gly Gly Ala Asn Pro Gly Asp Gly Asn Pro Lys Glu Ser
10              15                  20                  25 agt ccc ttc atc aac agc acg gac acg gag aag ggc aga gag tac gat     208
```

-continued

```
                Ser Pro Phe Ile Asn Ser Thr Asp Thr Glu Lys Gly Arg Glu Tyr Asp
                                30                  35                  40 ggc agg aac atg gcc ctg ttt gag gag gag atg gac acc agc ccc atg          256
Gly Arg Asn Met Ala Leu Phe Glu Glu Glu Met Asp Thr Ser Pro Met
                45                  50                  55 gta tcc tcc ctg ctc agt ggg ctg gcc aac tac acc aac cta ccc cag          304
Val Ser Ser Leu Leu Ser Gly Leu Ala Asn Tyr Thr Asn Leu Pro Gln
            60                  65                  70 gga agt aga gag cat gaa gaa gca gaa aat aat gag ggt gga aaa aag          352
Gly Ser Arg Glu His Glu Glu Ala Glu Asn Asn Glu Gly Gly Lys Lys
        75                  80                  85 aag ccg gtg cag gct cct cga atg ggc acc ttc atg ggt gtg tac ctg          400
Lys Pro Val Gln Ala Pro Arg Met Gly Thr Phe Met Gly Val Tyr Leu
90                  95                  100                 105 ccg tgc ctg cag aac atc ttt ggt gtc atc ctc ttc ctg cgg ctc acg          448
Pro Cys Leu Gln Asn Ile Phe Gly Val Ile Leu Phe Leu Arg Leu Thr
                110                 115                 120 tgg gtg gtg ggc atc gcg ggc atc atg gag tcc ttc tgt atg gtc ttc          496
Trp Val Val Gly Ile Ala Gly Ile Met Glu Ser Phe Cys Met Val Phe
                125                 130                 135 att tgc tgc tcc tgt acg atg ctc aca gcc att tcc atg agt gca atc          544
Ile Cys Cys Ser Cys Thr Met Leu Thr Ala Ile Ser Met Ser Ala Ile
            140                 145                 150 gca acc aat ggt gtt gtg cct gct ggt ggc tcg tac tac atg att tcc          592
Ala Thr Asn Gly Val Val Pro Ala Gly Gly Ser Tyr Tyr Met Ile Ser
        155                 160                 165 agg tct ctg ggc ccg gag ttt ggg ggc gcc gtg ggc ctc tgc ttc tac          640
Arg Ser Leu Gly Pro Glu Phe Gly Gly Ala Val Gly Leu Cys Phe Tyr
170                 175                 180                 185 ctg ggc acc acc ttt gct ggg gct atg tac atc ctt ggc acg atc gag          688
Leu Gly Thr Thr Phe Ala Gly Ala Met Tyr Ile Leu Gly Thr Ile Glu
                190                 195                 200 atc ctg ctg gct tat ctc ttc cca gct atg gcc atc ttc aag gca gaa          736
Ile Leu Leu Ala Tyr Leu Phe Pro Ala Met Ala Ile Phe Lys Ala Glu
            205                 210                 215 gat gcc agt ggg gag gcg gcc gcc atg ctg aac aac atg cgg gtg tat          784
Asp Ala Ser Gly Glu Ala Ala Ala Met Leu Asn Asn Met Arg Val Tyr
        220                 225                 230 ggc acc tgt gtg ctc acc tgc atg gcc acc gtt gtc ttt gtg ggt gtc          832
Gly Thr Cys Val Leu Thr Cys Met Ala Thr Val Val Phe Val Gly Val
235                 240                 245 aag tac gtc aac aag ttt gcc ttg gtc ttc ctg ggt tgc gtc atc ctg          880
Lys Tyr Val Asn Lys Phe Ala Leu Val Phe Leu Gly Cys Val Ile Leu
250                 255                 260                 265 tcc atc ctg gcc atc tat gca ggg gtc atc aag tct gcc ttc gac cca          928
Ser Ile Leu Ala Ile Tyr Ala Gly Val Ile Lys Ser Ala Phe Asp Pro
                270                 275                 280 ccc aat ttc ccg atc tgc ctc ctg ggg aac cgc acg ctg tct cgc cat          976
Pro Asn Phe Pro Ile Cys Leu Leu Gly Asn Arg Thr Leu Ser Arg His
            285                 290                 295 ggc ttt gat gtc tgt gcc aag ctg gct tgg gaa gga aat gag aca gtg         1024
Gly Phe Asp Val Cys Ala Lys Leu Ala Trp Glu Gly Asn Glu Thr Val
        300                 305                 310 acc aca cgg ctc tgg ggc ctt ttc tgc tcc tcc cgc ctc ctc aat gcc         1072
Thr Thr Arg Leu Trp Gly Leu Phe Cys Ser Ser Arg Leu Leu Asn Ala
315                 320                 325 acc tgt gat gag tac ttc acc cga aac aat gtc aca gag atc cag ggc         1120
Thr Cys Asp Glu Tyr Phe Thr Arg Asn Asn Val Thr Glu Ile Gln Gly
330                 335                 340                 345 att cct ggt gct gcc agt ggt ctc atc aaa gag aac ctg tgg agt tct         1168
```

-continued

| | | |
|---|---|---|
| Ile Pro Gly Ala Ala Ser Gly Leu Ile Lys Glu Asn Leu Trp Ser Ser<br>350 355 360 | | |
| tac ctg acc aaa ggg gtg att gtc gag agg cgt ggg atg ccc tct gtg<br>Tyr Leu Thr Lys Gly Val Ile Val Glu Arg Arg Gly Met Pro Ser Val<br>365 370 375 | 1216 | |
| ggc ctg gca gac ggt acc ccc gta gac atg gac cac ccc tat gtc ttc<br>Gly Leu Ala Asp Gly Thr Pro Val Asp Met Asp His Pro Tyr Val Phe<br>380 385 390 | 1264 | |
| agt gat atg acc tcc tac ttc acc ctc gtt ggt atc tac ttc ccc<br>Ser Asp Met Thr Ser Tyr Phe Thr Leu Leu Val Gly Ile Tyr Phe Pro<br>395 400 405 | 1312 | |
| tca gtc aca ggg atc atg gct ggc tca aac cga tct gga gac ctg cgg<br>Ser Val Thr Gly Ile Met Ala Gly Ser Asn Arg Ser Gly Asp Leu Arg<br>410 415 420 425 | 1360 | |
| gat gcc cag aag tct atc cct act gga act atc ctg gcc att gct acc<br>Asp Ala Gln Lys Ser Ile Pro Thr Gly Thr Ile Leu Ala Ile Ala Thr<br>430 435 440 | 1408 | |
| acc tct gct gtc tac atc agc tct gtt gtt ctg ttt gga gcc tgc atc<br>Thr Ser Ala Val Tyr Ile Ser Ser Val Val Leu Phe Gly Ala Cys Ile<br>445 450 455 | 1456 | |
| gag ggg gtc gtc tta cgg gac aag ttt ggg gaa gct gtg aat ggc aac<br>Glu Gly Val Val Leu Arg Asp Lys Phe Gly Glu Ala Val Asn Gly Asn<br>460 465 470 | 1504 | |
| ttg gtg gtg ggc acc ctg gcc tgg cct tct ccc tgg gtc atc gtc ata<br>Leu Val Val Gly Thr Leu Ala Trp Pro Ser Pro Trp Val Ile Val Ile<br>475 480 485 | 1552 | |
| ggc tct ttc ttc tct acc tgt ggg gct gga tta cag agc ctc aca ggg<br>Gly Ser Phe Phe Ser Thr Cys Gly Ala Gly Leu Gln Ser Leu Thr Gly<br>490 495 500 505 | 1600 | |
| gcc cca cgt ctg ctg cag gcc atc tcc cgg gat ggc ata gtg ccc ttc<br>Ala Pro Arg Leu Leu Gln Ala Ile Ser Arg Asp Gly Ile Val Pro Phe<br>510 515 520 | 1648 | |
| ctg cag gtc ttt ggc cat ggc aaa gct aat gga gag cca acc tgg gcg<br>Leu Gln Val Phe Gly His Gly Lys Ala Asn Gly Glu Pro Thr Trp Ala<br>525 530 535 | 1696 | |
| ctg ctg ctg act gcc tgc atc tgt gag atc ggc atc ctc ata gcc tcc<br>Leu Leu Leu Thr Ala Cys Ile Cys Glu Ile Gly Ile Leu Ile Ala Ser<br>540 545 550 | 1744 | |
| ctg gat gag gtc gcc cct ata ctt tcc atg ttc ttc cta atg tgt tac<br>Leu Asp Glu Val Ala Pro Ile Leu Ser Met Phe Phe Leu Met Cys Tyr<br>555 560 565 | 1792 | |
| atg ttt gtg aac ttg gct tgt gcg gtg cag acg ctg ctg agg aca ccc<br>Met Phe Val Asn Leu Ala Cys Ala Val Gln Thr Leu Leu Arg Thr Pro<br>570 575 580 585 | 1840 | |
| aac tgg agg cca cga ttt cgc tat tac cac tgg act ctc tcc ttc ctg<br>Asn Trp Arg Pro Arg Phe Arg Tyr Tyr His Trp Thr Leu Ser Phe Leu<br>590 595 600 | 1888 | |
| ggc atg agc ctc tgc ctg gcc ctc atg ttc att tgc tcc tgg tac tac<br>Gly Met Ser Leu Cys Leu Ala Leu Met Phe Ile Cys Ser Trp Tyr Tyr<br>605 610 615 | 1936 | |
| gca ctg gtg gcc atg ctc att gcc gga ctc att tat aag tac atc gag<br>Ala Leu Val Ala Met Leu Ile Ala Gly Leu Ile Tyr Lys Tyr Ile Glu<br>620 625 630 | 1984 | |
| tac cgg ggg gcg gag aag gag tgg ggg gat gga atc cga ggc ctg tct<br>Tyr Arg Gly Ala Glu Lys Glu Trp Gly Asp Gly Ile Arg Gly Leu Ser<br>635 640 645 | 2032 | |
| ctc agt gca gca cgc tat gct ctc ttg cgc ctg gag gaa gga cct ccg<br>Leu Ser Ala Ala Arg Tyr Ala Leu Leu Arg Leu Glu Glu Gly Pro Pro<br>650 655 660 665 | 2080 | |
| cat acg aag aac tgg agg ccc cag ctg ctg gtg ctg gtg cgt gtg gac | 2128 | |

```
            His Thr Lys Asn Trp Arg Pro Gln Leu Leu Val Leu Val Arg Val Asp
                            670                 675                 680 cag gat cag aac gtg gtg cat ccg cag ctg ctc tcc ctg acc tcc cag           2176
Gln Asp Gln Asn Val Val His Pro Gln Leu Leu Ser Leu Thr Ser Gln
                685                 690                 695 ctc aag gca ggg aag ggc ctg acc att gtg ggc tcc gtc ctt gag ggc           2224
Leu Lys Ala Gly Lys Gly Leu Thr Ile Val Gly Ser Val Leu Glu Gly
            700                 705                 710 acc ttt ctg gac aac cat cca cag gct cag cgg gca gag gag tct atc           2272
Thr Phe Leu Asp Asn His Pro Gln Ala Gln Arg Ala Glu Glu Ser Ile
        715                 720                 725 agg cgc ctg atg gag gct gag aag gtg aag ggc ttc tgc cag gta gtg           2320
Arg Arg Leu Met Glu Ala Glu Lys Val Lys Gly Phe Cys Gln Val Val
    730                 735                 740                 745 atc tcc tcc aac ctg cgt gat ggt gtg tcc cac ctg atc cag tct ggg           2368
Ile Ser Ser Asn Leu Arg Asp Gly Val Ser His Leu Ile Gln Ser Gly
                    750                 755                 760 ggc ctc ggg gga ttg caa cac aat acc gtg ctg gtg ggc tgg cct cgc           2416
Gly Leu Gly Gly Leu Gln His Asn Thr Val Leu Val Gly Trp Pro Arg
                765                 770                 775 aac tgg agg cag aag gag gat cat cag aca tgg agg aac ttc atc gaa           2464
Asn Trp Arg Gln Lys Glu Asp His Gln Thr Trp Arg Asn Phe Ile Glu
            780                 785                 790 ctg gtc cgg gaa act aca gcc ggc cac ctc gcc ctg ctg gtc acc aag           2512
Leu Val Arg Glu Thr Thr Ala Gly His Leu Ala Leu Leu Val Thr Lys
        795                 800                 805 aat gtt tcc atg ttt ccc ggg aac cct gag cgc ttc tcg gag ggc agc           2560
Asn Val Ser Met Phe Pro Gly Asn Pro Glu Arg Phe Ser Glu Gly Ser
810                 815                 820                 825 att gac gtg tgg tgg att gtg cac gac ggg ggc atg ctc atg ctg ctg           2608
Ile Asp Val Trp Trp Ile Val His Asp Gly Gly Met Leu Met Leu Leu
                    830                 835                 840 ccc ttc ctg ctg cga cac cac aag gtc tgg agg aaa tgc aaa atg cgg           2656
Pro Phe Leu Leu Arg His His Lys Val Trp Arg Lys Cys Lys Met Arg
                845                 850                 855 atc ttc acc gtg gcc cag atg gac gat aac agt atc cag atg aag aag           2704
Ile Phe Thr Val Ala Gln Met Asp Asp Asn Ser Ile Gln Met Lys Lys
            860                 865                 870 gac ctg acc acg ttt ctg tac cac tta cgc att act gca gag gtg gag           2752
Asp Leu Thr Thr Phe Leu Tyr His Leu Arg Ile Thr Ala Glu Val Glu
        875                 880                 885 gtg gtg gag atg cat gag agc gac atc tcg gca tac acc tac gag aag           2800
Val Val Glu Met His Glu Ser Asp Ile Ser Ala Tyr Thr Tyr Glu Lys
890                 895                 900                 905 aca tta gta atg gag caa cga tct cag atc ctc aaa cag atg cac ctc           2848
Thr Leu Val Met Glu Gln Arg Ser Gln Ile Leu Lys Gln Met His Leu
                    910                 915                 920 acc aag aac gag cgg gaa cgg gag atc cag agc atc aca gac gag tct           2896
Thr Lys Asn Glu Arg Glu Arg Glu Ile Gln Ser Ile Thr Asp Glu Ser
                925                 930                 935 cgg ggc tcc att cgg agg aag aat cca gcc aac ccc cgg ctc cgc ctc           2944
Arg Gly Ser Ile Arg Arg Lys Asn Pro Ala Asn Pro Arg Leu Arg Leu
            940                 945                 950 aat gtt ccc gaa gag aca gcg tgt gac aat gag gag aag cca gag gag           2992
Asn Val Pro Glu Glu Thr Ala Cys Asp Asn Glu Glu Lys Pro Glu Glu
        955                 960                 965 gag gtg cag ctg atc cat gac cag agt gct ccc agc tgc cct agc agc           3040
Glu Val Gln Leu Ile His Asp Gln Ser Ala Pro Ser Cys Pro Ser Ser
970                 975                 980                 985 tcg cca tct cca ggg gag gag ccc gag ggg gag agg gag aca gac cca           3088
```

```
Ser Pro Ser Pro Gly Glu Glu Pro Glu Gly Glu Arg Glu Thr Asp  Pro
            990                 995                 1000 gag gtg cat ctt  acc tgg acc aag gat  aag tca gtg gca gag  aag        3133
Glu Val His Leu  Thr Trp Thr Lys Asp  Lys Ser Val Ala Glu  Lys
            1005                1010                1015 aat aaa ggc ccc  agt ccc gtc tcc tcc  gag ggc atc aag gac  ttc        3178
Asn Lys Gly Pro  Ser Pro Val Ser Ser  Glu Gly Ile Lys Asp  Phe
            1020                1025                1030 ttc agc atg aag  ccg gag tgg gaa aac  ttg aac cag tcc aat  gta        3223
Phe Ser Met Lys  Pro Glu Trp Glu Asn  Leu Asn Gln Ser Asn  Val
            1035                1040                1045 cgg cgc atg cac  aca gct gtg cgg ctg  aac gag gtc atc gtg  aat        3268
Arg Arg Met His  Thr Ala Val Arg Leu  Asn Glu Val Ile Val  Asn
            1050                1055                1060 aaa tct cgg gat  gcc aag cta gtt ttg  ctc aac atg ccc ggg  cct        3313
Lys Ser Arg Asp  Ala Lys Leu Val Leu  Leu Asn Met Pro Gly  Pro
            1065                1070                1075 ccc cgc aac cgc  aat ggg gat gaa aac  tac atg gaa ttc ttg  gag        3358
Pro Arg Asn Arg  Asn Gly Asp Glu Asn  Tyr Met Glu Phe Leu  Glu
            1080                1085                1090 gtc ctc act gag  caa ctg gac cgg gtg  atg ctg gtc cgc ggt  ggc        3403
Val Leu Thr Glu  Gln Leu Asp Arg Val  Met Leu Val Arg Gly  Gly
            1095                1100                1105 ggc cga gag gtc  atc acc atc tac tcc  tga aggccaggac ctgccactcc       3453
Gly Arg Glu Val  Ile Thr Ile Tyr Ser
            1110                1115 ggcccgagcg cgcccggccc gcggcccccca gagccctcgc cgcgcctccc cgccgctgtc    3513
accgtttaca taagacccag ttgcccatgc cctggcccct ttccttcccg ctgcctgcag     3573
ccctgaggcc ttgcccgtcg gggctgaccc gcagggcggc ccgtgaggcc ccttttctga    3633
gcctggcctc gccccgccgg agc                                            3656

<210> SEQ ID NO 4
<211> LENGTH: 1115
<212> TYPE: PRT
<213> ORGANISM: Mus musculus

<400> SEQUENCE: 4

Met Leu Asn Asn Leu Thr Asp Cys Glu Asp Gly Asp Gly Gly Ala Asn
1               5                   10                  15

Pro Gly Asp Gly Asn Pro Lys Glu Ser Ser Pro Phe Ile Asn Ser Thr
            20                  25                  30

Asp Thr Glu Lys Gly Arg Glu Tyr Asp Gly Arg Asn Met Ala Leu Phe
        35                  40                  45

Glu Glu Glu Met Asp Thr Ser Pro Met Val Ser Ser Leu Leu Ser Gly
    50                  55                  60

Leu Ala Asn Tyr Thr Asn Leu Pro Gln Gly Ser Arg Glu His Glu Glu
65              70                  75                  80

Ala Glu Asn Asn Glu Gly Gly Lys Lys Lys Pro Val Gln Ala Pro Arg
                85                  90                  95

Met Gly Thr Phe Met Gly Val Tyr Leu Pro Cys Leu Gln Asn Ile Phe
            100                 105                 110

Gly Val Ile Leu Phe Leu Arg Leu Thr Trp Val Val Gly Ile Ala Gly
        115                 120                 125

Ile Met Glu Ser Phe Cys Met Val Phe Ile Cys Cys Ser Cys Thr Met
    130                 135                 140

Leu Thr Ala Ile Ser Met Ser Ala Ile Ala Thr Asn Gly Val Val Pro
145             150                 155                 160
```

-continued

```
Ala Gly Gly Ser Tyr Tyr Met Ile Ser Arg Ser Leu Gly Pro Glu Phe
            165                 170                 175
Gly Gly Ala Val Gly Leu Cys Phe Tyr Leu Gly Thr Thr Phe Ala Gly
            180                 185                 190
Ala Met Tyr Ile Leu Gly Thr Ile Glu Ile Leu Leu Ala Tyr Leu Phe
            195                 200                 205
Pro Ala Met Ala Ile Phe Lys Ala Glu Asp Ala Ser Gly Glu Ala Ala
210                 215                 220
Ala Met Leu Asn Asn Met Arg Val Tyr Gly Thr Cys Val Leu Thr Cys
225                 230                 235                 240
Met Ala Thr Val Val Phe Val Gly Val Lys Tyr Val Asn Lys Phe Ala
                245                 250                 255
Leu Val Phe Leu Gly Cys Val Ile Leu Ser Ile Leu Ala Ile Tyr Ala
                260                 265                 270
Gly Val Ile Lys Ser Ala Phe Asp Pro Pro Asn Phe Pro Ile Cys Leu
            275                 280                 285
Leu Gly Asn Arg Thr Leu Ser Arg His Gly Phe Asp Val Cys Ala Lys
            290                 295                 300
Leu Ala Trp Glu Gly Asn Glu Thr Val Thr Thr Arg Leu Trp Gly Leu
305                 310                 315                 320
Phe Cys Ser Ser Arg Leu Leu Asn Ala Thr Cys Asp Glu Tyr Phe Thr
                325                 330                 335
Arg Asn Asn Val Thr Glu Ile Gln Gly Ile Pro Gly Ala Ala Ser Gly
                340                 345                 350
Leu Ile Lys Glu Asn Leu Trp Ser Ser Tyr Leu Thr Lys Gly Val Ile
            355                 360                 365
Val Glu Arg Arg Gly Met Pro Ser Val Gly Leu Ala Asp Gly Thr Pro
370                 375                 380
Val Asp Met Asp His Pro Tyr Val Phe Ser Asp Met Thr Ser Tyr Phe
385                 390                 395                 400
Thr Leu Leu Val Gly Ile Tyr Phe Pro Ser Val Thr Gly Ile Met Ala
                405                 410                 415
Gly Ser Asn Arg Ser Gly Asp Leu Arg Asp Ala Gln Lys Ser Ile Pro
                420                 425                 430
Thr Gly Thr Ile Leu Ala Ile Ala Thr Thr Ser Ala Val Tyr Ile Ser
            435                 440                 445
Ser Val Val Leu Phe Gly Ala Cys Ile Glu Gly Val Val Leu Arg Asp
450                 455                 460
Lys Phe Gly Glu Ala Val Asn Gly Asn Leu Val Val Gly Thr Leu Ala
465                 470                 475                 480
Trp Pro Ser Pro Trp Val Ile Val Ile Gly Ser Phe Phe Ser Thr Cys
                485                 490                 495
Gly Ala Gly Leu Gln Ser Leu Thr Gly Ala Pro Arg Leu Leu Gln Ala
            500                 505                 510
Ile Ser Arg Asp Gly Ile Val Pro Phe Leu Gln Val Phe Gly His Gly
            515                 520                 525
Lys Ala Asn Gly Glu Pro Thr Trp Ala Leu Leu Leu Thr Ala Cys Ile
            530                 535                 540
Cys Glu Ile Gly Ile Leu Ile Ala Ser Leu Asp Glu Val Ala Pro Ile
545                 550                 555                 560
Leu Ser Met Phe Phe Leu Met Cys Tyr Met Phe Val Asn Leu Ala Cys
                565                 570                 575
Ala Val Gln Thr Leu Leu Arg Thr Pro Asn Trp Arg Pro Arg Phe Arg
```

```
                  580             585             590
Tyr Tyr His Trp Thr Leu Ser Phe Leu Gly Met Ser Leu Cys Leu Ala
        595             600             605

Leu Met Phe Ile Cys Ser Trp Tyr Tyr Ala Leu Val Ala Met Leu Ile
        610             615             620

Ala Gly Leu Ile Tyr Lys Tyr Ile Glu Tyr Arg Gly Ala Glu Lys Glu
625             630             635             640

Trp Gly Asp Gly Ile Arg Gly Leu Ser Leu Ser Ala Ala Arg Tyr Ala
                645             650             655

Leu Leu Arg Leu Glu Glu Gly Pro Pro His Thr Lys Asn Trp Arg Pro
        660             665             670

Gln Leu Leu Val Leu Val Arg Val Asp Gln Asp Gln Asn Val Val His
        675             680             685

Pro Gln Leu Leu Ser Leu Thr Ser Gln Leu Lys Ala Gly Lys Gly Leu
        690             695             700

Thr Ile Val Gly Ser Val Leu Glu Gly Thr Phe Leu Asp Asn His Pro
705             710             715             720

Gln Ala Gln Arg Ala Glu Glu Ser Ile Arg Arg Leu Met Glu Ala Glu
                725             730             735

Lys Val Lys Gly Phe Cys Gln Val Val Ile Ser Ser Asn Leu Arg Asp
                740             745             750

Gly Val Ser His Leu Ile Gln Ser Gly Gly Leu Gly Leu Gln His
                755             760             765

Asn Thr Val Leu Val Gly Trp Pro Arg Asn Trp Arg Gln Lys Glu Asp
        770             775             780

His Gln Thr Trp Arg Asn Phe Ile Glu Leu Val Arg Glu Thr Thr Ala
785             790             795             800

Gly His Leu Ala Leu Leu Val Thr Lys Asn Val Ser Met Phe Pro Gly
                805             810             815

Asn Pro Glu Arg Phe Ser Glu Gly Ser Ile Asp Val Trp Trp Ile Val
                820             825             830

His Asp Gly Gly Met Leu Met Leu Leu Pro Phe Leu Leu Arg His His
                835             840             845

Lys Val Trp Arg Lys Cys Lys Met Arg Ile Phe Thr Val Ala Gln Met
        850             855             860

Asp Asp Asn Ser Ile Gln Met Lys Lys Asp Leu Thr Thr Phe Leu Tyr
865             870             875             880

His Leu Arg Ile Thr Ala Glu Val Glu Val Val Glu Met His Glu Ser
                885             890             895

Asp Ile Ser Ala Tyr Thr Tyr Glu Lys Thr Leu Val Met Glu Gln Arg
                900             905             910

Ser Gln Ile Leu Lys Gln Met His Leu Thr Lys Asn Glu Arg Glu Arg
        915             920             925

Glu Ile Gln Ser Ile Thr Asp Glu Ser Arg Gly Ser Ile Arg Arg Lys
        930             935             940

Asn Pro Ala Asn Pro Arg Leu Arg Leu Asn Val Pro Glu Glu Thr Ala
945             950             955             960

Cys Asp Asn Glu Glu Lys Pro Glu Glu Val Gln Leu Ile His Asp
                965             970             975

Gln Ser Ala Pro Ser Cys Pro Ser Ser Ser Pro Ser Pro Gly Glu Glu
                980             985             990

Pro Glu Gly Glu Arg Glu Thr Asp Pro Glu Val His Leu Thr Trp Thr
        995             1000            1005
```

```
Lys Asp Lys Ser Val Ala Glu Lys Asn Lys Gly Pro Ser Pro Val
    1010            1015                1020

Ser Ser Glu Gly Ile Lys Asp Phe Phe Ser Met Lys Pro Glu Trp
    1025            1030                1035

Glu Asn Leu Asn Gln Ser Asn Val Arg Arg Met His Thr Ala Val
    1040            1045                1050

Arg Leu Asn Glu Val Ile Val Asn Lys Ser Arg Asp Ala Lys Leu
    1055            1060                1065

Val Leu Leu Asn Met Pro Gly Pro Pro Arg Asn Arg Asn Gly Asp
    1070            1075                1080

Glu Asn Tyr Met Glu Phe Leu Glu Val Leu Thr Glu Gln Leu Asp
    1085            1090                1095

Arg Val Met Leu Val Arg Gly Gly Gly Arg Glu Val Ile Thr Ile
    1100            1105                1110

Tyr Ser
    1115

<210> SEQ ID NO 5
<211> LENGTH: 5566
<212> TYPE: DNA
<213> ORGANISM: Rattus norvegicus
<220> FEATURE:
<221> NAME/KEY: CDS
<222> LOCATION: (116)..(3466)

<400> SEQUENCE: 5
ccgctccacg gagagcaagc gacagagctc gagcaagcga gcgagcggcg aaggcgggca      60
gaggggcgcg ggcgaagagg cgcagccatc ccgagcccgg cgccgcgcag ccacc atg     118
                                                              Met
                                                                1 ctc aac aac ctg acg gac tgc gag gac ggc gat ggg gga gcc aac ccg       166
Leu Asn Asn Leu Thr Asp Cys Glu Asp Gly Asp Gly Gly Ala Asn Pro
        5                   10                  15 ggt gac ggc aat ccc aag gag agc agc ccc ttc atc aac agc acg gac       214
Gly Asp Gly Asn Pro Lys Glu Ser Ser Pro Phe Ile Asn Ser Thr Asp
    20                  25                  30 acg gag aag ggg aga gag tat gat ggc agg aac atg gcc ctg ttt gag       262
Thr Glu Lys Gly Arg Glu Tyr Asp Gly Arg Asn Met Ala Leu Phe Glu
35                  40                  45 gag gag atg gac acc agc ccc atg gta tcc tcc ctg ctc agt ggg ctg       310
Glu Glu Met Asp Thr Ser Pro Met Val Ser Ser Leu Leu Ser Gly Leu
 50                  55                  60                  65 gcc aac tac acc aac ctg cct cag gga agc aaa gag cac gaa gaa gca       358
Ala Asn Tyr Thr Asn Leu Pro Gln Gly Ser Lys Glu His Glu Glu Ala
                70                  75                  80 gaa aac aat gag ggc gga aag aag aag ccg gtg cag gcc cca cgc atg       406
Glu Asn Asn Glu Gly Gly Lys Lys Lys Pro Val Gln Ala Pro Arg Met
            85                  90                  95 ggc acc ttc atg ggc gtg tac ctc ccg tgc ctg cag aac atc ttt ggt       454
Gly Thr Phe Met Gly Val Tyr Leu Pro Cys Leu Gln Asn Ile Phe Gly
        100                 105                 110 gtt atc ctc ttt ctg cgg ctc act tgg gtg gtg gga atc gca ggc atc       502
Val Ile Leu Phe Leu Arg Leu Thr Trp Val Val Gly Ile Ala Gly Ile
    115                 120                 125 atg gag tcc ttc tgc atg gtc ttc atc tgc tgc tcc tgc acg atg ctc       550
Met Glu Ser Phe Cys Met Val Phe Ile Cys Cys Ser Cys Thr Met Leu
130                 135                 140                 145 aca gcc att tcc atg agc gca att gca acc aat ggt gtt gtg cct gct       598
Thr Ala Ile Ser Met Ser Ala Ile Ala Thr Asn Gly Val Val Pro Ala
                150                 155                 160
```

| | | |
|---|---|---|
| ggt ggc tcc tac tac atg att tcc agg tct ctg ggc ccg gag ttt ggg<br>Gly Gly Ser Tyr Tyr Met Ile Ser Arg Ser Leu Gly Pro Glu Phe Gly<br>165 170 175 | | 646 |
| ggc gcc gtg ggc ctc tgc ttc tac ctg ggc act acc ttt gct ggg gct<br>Gly Ala Val Gly Leu Cys Phe Tyr Leu Gly Thr Thr Phe Ala Gly Ala<br>180 185 190 | | 694 |
| atg tac atc ctg ggc acc atc gag atc ctg ctg gct tac ctc ttc cca<br>Met Tyr Ile Leu Gly Thr Ile Glu Ile Leu Leu Ala Tyr Leu Phe Pro<br>195 200 205 | | 742 |
| gcg atg gcc atc ttc aag gca gaa gat gcc agt ggg gag gca gcc gcc<br>Ala Met Ala Ile Phe Lys Ala Glu Asp Ala Ser Gly Glu Ala Ala Ala<br>210 215 220 225 | | 790 |
| atg ttg aat aac atg cgg gtg tat ggc acc tgt gtg ctc acc tgc atg<br>Met Leu Asn Asn Met Arg Val Tyr Gly Thr Cys Val Leu Thr Cys Met<br>230 235 240 | | 838 |
| gcc acc gta gtc ttt gtg ggc gtc aag tac gtg aac aag ttt gcc ctg<br>Ala Thr Val Val Phe Val Gly Val Lys Tyr Val Asn Lys Phe Ala Leu<br>245 250 255 | | 886 |
| gtc ttc ctg ggt tgc gtg atc ctc tcc atc ctg gcc atc tac gca ggg<br>Val Phe Leu Gly Cys Val Ile Leu Ser Ile Leu Ala Ile Tyr Ala Gly<br>260 265 270 | | 934 |
| gtc atc aag tct gcc ttc gat cca ccc aat ttc ccg att tgc ctc ctg<br>Val Ile Lys Ser Ala Phe Asp Pro Pro Asn Phe Pro Ile Cys Leu Leu<br>275 280 285 | | 982 |
| ggg aac cgc acg ctg tct cgc cat ggc ttt gat gtc tgt gcc aag ctg<br>Gly Asn Arg Thr Leu Ser Arg His Gly Phe Asp Val Cys Ala Lys Leu<br>290 295 300 305 | | 1030 |
| gct tgg gaa gga aat gag aca gtg acc aca cgg ctc tgg ggc cta ttc<br>Ala Trp Glu Gly Asn Glu Thr Val Thr Thr Arg Leu Trp Gly Leu Phe<br>310 315 320 | | 1078 |
| tgt tcc tcc cgc ctc ctc aat gcc acc tgt gat gag tac ttc acc cga<br>Cys Ser Ser Arg Leu Leu Asn Ala Thr Cys Asp Glu Tyr Phe Thr Arg<br>325 330 335 | | 1126 |
| aac aat gtc aca gag atc cag ggc att cct ggt gct gca agt ggc ctc<br>Asn Asn Val Thr Glu Ile Gln Gly Ile Pro Gly Ala Ala Ser Gly Leu<br>340 345 350 | | 1174 |
| atc aaa gag aac ctg tgg agt tcc tac ctg acc aag ggg gtg atc gtg<br>Ile Lys Glu Asn Leu Trp Ser Ser Tyr Leu Thr Lys Gly Val Ile Val<br>355 360 365 | | 1222 |
| gag agg cgt ggg atg ccc tct gtg ggc ctg gca gat ggt acc ccc gtt<br>Glu Arg Arg Gly Met Pro Ser Val Gly Leu Ala Asp Gly Thr Pro Val<br>370 375 380 385 | | 1270 |
| gac atg gac cac ccc tat gtc ttc agt gat atg acc tcc tac ttc acc<br>Asp Met Asp His Pro Tyr Val Phe Ser Asp Met Thr Ser Tyr Phe Thr<br>390 395 400 | | 1318 |
| ctg ctt gtt ggc atc tat ttc ccc tca gtc aca ggg atc atg gct ggc<br>Leu Leu Val Gly Ile Tyr Phe Pro Ser Val Thr Gly Ile Met Ala Gly<br>405 410 415 | | 1366 |
| tcg aac cgg tcc gga gac ctg cgg gat gcc cag aag tct atc cct act<br>Ser Asn Arg Ser Gly Asp Leu Arg Asp Ala Gln Lys Ser Ile Pro Thr<br>420 425 430 | | 1414 |
| gga act atc ttg gcc att gct acg acc tct gct gtc tac atc agc tct<br>Gly Thr Ile Leu Ala Ile Ala Thr Thr Ser Ala Val Tyr Ile Ser Ser<br>435 440 445 | | 1462 |
| gtt gtc ctg ttc gga gcc tgc atc gaa ggg gtc gtc cta cgg gac aag<br>Val Val Leu Phe Gly Ala Cys Ile Glu Gly Val Val Leu Arg Asp Lys<br>450 455 460 465 | | 1510 |
| ttt ggg gaa gct gtg aat ggc aat ctg gtg gtg ggc acc ctg gcc tgg<br>Phe Gly Glu Ala Val Asn Gly Asn Leu Val Val Gly Thr Leu Ala Trp<br>470 475 480 | | 1558 |

```
cct tct cct tgg gtc att gtc ata ggc tct ttc ttc tct acc tgc gga    1606
Pro Ser Pro Trp Val Ile Val Ile Gly Ser Phe Phe Ser Thr Cys Gly
            485                 490                 495 gct gga cta cag agc ctc aca ggg gcc cca cgc ctg ctg cag gcc atc    1654
Ala Gly Leu Gln Ser Leu Thr Gly Ala Pro Arg Leu Leu Gln Ala Ile
        500                 505                 510 tcc cgg gat ggc ata gtg ccc ttc ctg cag gtc ttt ggc cat ggc aaa    1702
Ser Arg Asp Gly Ile Val Pro Phe Leu Gln Val Phe Gly His Gly Lys
    515                 520                 525 gcc aac gga gag cca acc tgg gcg ctg ctg act gcc tgc atc tgt        1750
Ala Asn Gly Glu Pro Thr Trp Ala Leu Leu Thr Ala Cys Ile Cys
530                 535                 540                 545 gag atc ggc atc ctc atc gcc tcc ctg gat gag gtc gcc cct atc ctt    1798
Glu Ile Gly Ile Leu Ile Ala Ser Leu Asp Glu Val Ala Pro Ile Leu
                550                 555                 560 tcc atg ttc ttc ctg atg tgt tac atg ttt gtg aac ttg gct tgc gcg    1846
Ser Met Phe Phe Leu Met Cys Tyr Met Phe Val Asn Leu Ala Cys Ala
            565                 570                 575 gtg cag aca ctg ctg agg acg ccc aac tgg agg cca cgc ttc cga tat    1894
Val Gln Thr Leu Leu Arg Thr Pro Asn Trp Arg Pro Arg Phe Arg Tyr
        580                 585                 590 tac cac tgg acc ctc tcc ttc ctg ggc atg agc ctc tgc ctg gcc ctg    1942
Tyr His Trp Thr Leu Ser Phe Leu Gly Met Ser Leu Cys Leu Ala Leu
    595                 600                 605 atg ttc att tgc tcc tgg tat tat gcg ctg gta gct atg ctc atc gct    1990
Met Phe Ile Cys Ser Trp Tyr Tyr Ala Leu Val Ala Met Leu Ile Ala
610                 615                 620                 625 ggc ctc atc tat aag tac atc gag tac cgg ggg gca gag aag gag tgg    2038
Gly Leu Ile Tyr Lys Tyr Ile Glu Tyr Arg Gly Ala Glu Lys Glu Trp
                630                 635                 640 ggg gat ggg atc cga ggc ctg tct ctc agt gca gct cgc tat gct ctc    2086
Gly Asp Gly Ile Arg Gly Leu Ser Leu Ser Ala Ala Arg Tyr Ala Leu
            645                 650                 655 ttg cgt ctg gag gaa gga ccc ccg cat aca aag aac tgg agg ccc cag    2134
Leu Arg Leu Glu Glu Gly Pro Pro His Thr Lys Asn Trp Arg Pro Gln
        660                 665                 670 cta ctg gtg ctg gtg cgt gtg gac cag gac cag aac gtg gtg cac ccg    2182
Leu Leu Val Leu Val Arg Val Asp Gln Asp Gln Asn Val Val His Pro
    675                 680                 685 cag ctg ctg tcc ttg acc tcc cag ctc aag gca ggg aag ggc ctg acc    2230
Gln Leu Leu Ser Leu Thr Ser Gln Leu Lys Ala Gly Lys Gly Leu Thr
690                 695                 700                 705 att gtg ggc tct gtc ctt gag ggc acc ttt ctg gac aac cac cct cag    2278
Ile Val Gly Ser Val Leu Glu Gly Thr Phe Leu Asp Asn His Pro Gln
                710                 715                 720 gct cag cgg gca gag gag tct atc cgg cgc ctg atg gag gct gag aag    2326
Ala Gln Arg Ala Glu Glu Ser Ile Arg Arg Leu Met Glu Ala Glu Lys
            725                 730                 735 gtg aag ggc ttc tgc cag gta gtg atc tcc tcc aac ctg cgt gac ggt    2374
Val Lys Gly Phe Cys Gln Val Val Ile Ser Ser Asn Leu Arg Asp Gly
        740                 745                 750 gtg tcc cac ctg atc caa tcc ggg ggc ctc ggg ggc ctg caa cac aac    2422
Val Ser His Leu Ile Gln Ser Gly Gly Leu Gly Gly Leu Gln His Asn
    755                 760                 765 act gtg cta gtg ggc tgg cct cgc aac tgg cga cag aag gag gat cat    2470
Thr Val Leu Val Gly Trp Pro Arg Asn Trp Arg Gln Lys Glu Asp His
770                 775                 780                 785 cag aca tgg agg aac ttc atc gaa ctc gtc cgg gaa act aca gct ggc    2518
Gln Thr Trp Arg Asn Phe Ile Glu Leu Val Arg Glu Thr Thr Ala Gly
                790                 795                 800
```

```
cac ctc gcc ctg ctg gtc acc aag aat gtt tcc atg ttc ccc ggg aac    2566
His Leu Ala Leu Leu Val Thr Lys Asn Val Ser Met Phe Pro Gly Asn
            805                 810                 815 cct gag cgt ttc tct gag ggc agc att gac gtg tgg tgg atc gtg cac    2614
Pro Glu Arg Phe Ser Glu Gly Ser Ile Asp Val Trp Trp Ile Val His
        820                 825                 830 gac ggg ggc atg ctc atg ctg ttg ccc ttc ctc ctg cgt cac cac aag    2662
Asp Gly Gly Met Leu Met Leu Leu Pro Phe Leu Leu Arg His His Lys
835                 840                 845 gtc tgg agg aaa tgc aaa atg cgg atc ttc acc gtg gcg cag atg gat    2710
Val Trp Arg Lys Cys Lys Met Arg Ile Phe Thr Val Ala Gln Met Asp
850                 855                 860                 865 gac aac agc att cag atg aag aaa gac ctg acc acg ttt ctg tac cac    2758
Asp Asn Ser Ile Gln Met Lys Lys Asp Leu Thr Thr Phe Leu Tyr His
            870                 875                 880 tta cga att act gca gag gtg gaa gtc gtg gag atg cac gag agc gac    2806
Leu Arg Ile Thr Ala Glu Val Glu Val Val Glu Met His Glu Ser Asp
        885                 890                 895 atc tca gca tac acc tac gag aag aca ttg gta atg gaa caa cgt tct    2854
Ile Ser Ala Tyr Thr Tyr Glu Lys Thr Leu Val Met Glu Gln Arg Ser
900                 905                 910 cag atc ctc aaa cag atg cac ctc acc aag aac gag cgg gaa cgg gag    2902
Gln Ile Leu Lys Gln Met His Leu Thr Lys Asn Glu Arg Glu Arg Glu
915                 920                 925 atc cag agc atc aca gat gaa tct cgg ggc tcc att cgg agg aag aat    2950
Ile Gln Ser Ile Thr Asp Glu Ser Arg Gly Ser Ile Arg Arg Lys Asn
930                 935                 940                 945 cca gcc aac act cgg ctc cgc ctc aat gtt ccc gaa gag aca gct tgt    2998
Pro Ala Asn Thr Arg Leu Arg Leu Asn Val Pro Glu Glu Thr Ala Cys
            950                 955                 960 gac aac gag gag aag cca gaa gag gag gtg cag ctg atc cat gac cag    3046
Asp Asn Glu Glu Lys Pro Glu Glu Glu Val Gln Leu Ile His Asp Gln
        965                 970                 975 agt gct ccc agc tgc cct agc agc tcg ccg tct cca ggg gag gag cct    3094
Ser Ala Pro Ser Cys Pro Ser Ser Ser Pro Ser Pro Gly Glu Glu Pro
980                 985                 990 gag ggg gag ggg gag aca gac cca gag aag gtg cat ctc acc tgg acc    3142
Glu Gly Glu Gly Glu Thr Asp Pro Glu Lys Val His Leu Thr Trp Thr
    995                 1000                1005 aag gat aag tca gcg gct cag aag aac aaa ggc ccc agt ccc gtc       3187
Lys Asp Lys Ser Ala Ala Gln Lys Asn Lys Gly Pro Ser Pro Val
1010                1015                1020 tcc tcg gag ggg atc aag gac ttc ttc agc atg aag ccg gag tgg       3232
Ser Ser Glu Gly Ile Lys Asp Phe Phe Ser Met Lys Pro Glu Trp
1025                1030                1035 gaa aac ttg aac cag tcc aac gtg cgg cgc atg cac aca gct gtg       3277
Glu Asn Leu Asn Gln Ser Asn Val Arg Arg Met His Thr Ala Val
1040                1045                1050 cgg ctg aac gag gtc atc gtg aat aaa tcc cgg gat gcc aag ttg       3322
Arg Leu Asn Glu Val Ile Val Asn Lys Ser Arg Asp Ala Lys Leu
1055                1060                1065 gtg ttg ctc aac atg ccc ggg cct ccc cgc aac cgc aat gga gat       3367
Val Leu Leu Asn Met Pro Gly Pro Pro Arg Asn Arg Asn Gly Asp
1070                1075                1080 gaa aac tac atg gaa ttc ctg gag gtc ctc act gag caa ctg gac       3412
Glu Asn Tyr Met Glu Phe Leu Glu Val Leu Thr Glu Gln Leu Asp
1085                1090                1095 cgg gtg atg ctg gtc cgc ggt ggt ggc cga gag gtc atc acc atc       3457
Arg Val Met Leu Val Arg Gly Gly Gly Arg Glu Val Ile Thr Ile
1100                1105                1110
```

```
tac tcc tga aggccaggac ctgccactcc ggcccgagcg agcccggccc        3506
Tyr Ser
1115 gcggccccgg agccctcgcc gcgcctcccc gccgctgtca ccgtttacat aagacccgt  3566
tgcccgtgcc ctggccctct tccctcccgc tgcctgcggc ccggaggcct tgcccgtcgg  3626
ggctgacccg gagggcggcc cgtgggcccc ttttctgagc ccggcctcgc cctgccggag  3686
tagacgttgc aataaaggtg gcgaggcggc gtggagagga gcggaaccgt ggtcccgggc  3746
cggggagccc cgagcccgtc cctcccacg ccccgccgcg ctcccccgg accctggtcg  3806
ctgagcccgg gcgccgctcg gctgcgctat acatagtgta caggagacat cgagtgtatt  3866
tttaatgtcc ccatatttct gtaaactaga acgcaacgg actcctcgcc acggccgcgc  3926
tctccccgct gcgggcgccc aggaaggcgg agacccggga agccagggtt ccctgcgctc  3986
ccgagctgag agccaagtgc tttaaggccg gcgctctcct ttccctttcc tgtccacggc  4046
ccgggcttcc ctctcttccc tccagttctt ggcgaacaca ggtgaagccc tgcccggtgc  4106
cttcgtggag gagcaggcgt ctctcctctg ttggcttgcc gcctgctccc cctgtcccgt  4166
ggctcctcgc caaagactga atttgtggag ctggagggca caccctcccc actttccttc  4226
ctgggacagg tgaggggcca atgccagtct aggggccgac tcacaggagg cctcgcgcag  4286
cctcttggtc cccactctgc aagtcctgcc tgggaccca gccccctgg tggttctggg   4346
gcggagcttt gctgcctagc agcaagtcct tagttactgt ctccagatac caggacctgg  4406
agtagggaat ggagtcatat gggttcagtt gttcctggcg cttctctgcc ccctgctccc  4466
cctctccccc tctcgtagga cacaaggact ttggctttct taactcatcc ttggcgcttc  4526
cgctccacca cgcccacctg tggggaggag ccctcagccc tagagaggcg tttggctggt  4586
tcccttcccc cagggcacgt tactaagagg acaggcactg catgctcctt taagcgccct  4646
ctgggactgg gtacagtgcc tccagcccca gggcctggt ctgcgcacct agttagacat   4706
cattgcccac tccagggcca gggccactag ctgacctcac cacctttttc cttgagccca  4766
aggcagagag agctgcagct ggtgccatct agacaggctc aagtgtggcc agtgcaggg   4826
ctcgagggcc actgccctgt tgcttggctc aggacctctc tgagatttga tggggactgg  4886
atattcttcc aggtagtagc catcaagtcg gaagtgttgg acccaggacc tgacattcct  4946
tcaagactgc cctcccttgc tgtggttttg ccttttgggg caagagaggg gctgggcaaa  5006
cggggaggag gcagtatcaa caccgattag ggaaccaaag ttgcactacc tgggcccagc  5066
ctctggttgg caagagcaaa gtttctgttg atgaaaacaa acagcccaca acaacccc    5126
ccccccgtt ttctgtgctc catgtgcaat atttgttatg aaccttgtgt cgttcaagtc   5186
acctttataa tcactgtagc tagatgttcc atgtccatcc aggtgacttt actctgagtg  5246
caatatttca atagcctggt agtgagaaga gtgttgcttt tgtttcagcc gacctatgtg  5306
cagggcaatg caatgcagtc caaaacccctt gtaaatagga gaggttgcaa gccaaatcaa  5366
gagtatttat cgttattact attattatta ggcctgcctt taattttagt gtttcggtat  5426
ttcgcatcct gcctcggtat tgatcgtgtg ttctctgtgc caatatgcaa aggagaggat  5486
cagttctttc ctttactgtt gaatgctccc atttactgct ttaaggcttt tactgtgttc  5546
atttttaga tacctgtctg                                               5566
```

<210> SEQ ID NO 6
<211> LENGTH: 1116
<212> TYPE: PRT
<213> ORGANISM: Rattus norvegicus

<400> SEQUENCE: 6

```
Met Leu Asn Asn Leu Thr Asp Cys Glu Asp Gly Asp Gly Gly Ala Asn
1               5                   10                  15

Pro Gly Asp Gly Asn Pro Lys Glu Ser Ser Pro Phe Ile Asn Ser Thr
            20                  25                  30

Asp Thr Glu Lys Gly Arg Glu Tyr Asp Gly Arg Asn Met Ala Leu Phe
        35                  40                  45

Glu Glu Glu Met Asp Thr Ser Pro Met Val Ser Ser Leu Leu Ser Gly
    50                  55                  60

Leu Ala Asn Tyr Thr Asn Leu Pro Gln Gly Ser Lys Glu His Glu Glu
65                  70                  75                  80

Ala Glu Asn Asn Glu Gly Gly Lys Lys Lys Pro Val Gln Ala Pro Arg
                85                  90                  95

Met Gly Thr Phe Met Gly Val Tyr Leu Pro Cys Leu Gln Asn Ile Phe
            100                 105                 110

Gly Val Ile Leu Phe Leu Arg Leu Thr Trp Val Val Gly Ile Ala Gly
        115                 120                 125

Ile Met Glu Ser Phe Cys Met Val Phe Ile Cys Cys Ser Cys Thr Met
    130                 135                 140

Leu Thr Ala Ile Ser Met Ser Ala Ile Ala Thr Asn Gly Val Val Pro
145                 150                 155                 160

Ala Gly Gly Ser Tyr Tyr Met Ile Ser Arg Ser Leu Gly Pro Glu Phe
                165                 170                 175

Gly Gly Ala Val Gly Leu Cys Phe Tyr Leu Gly Thr Thr Phe Ala Gly
            180                 185                 190

Ala Met Tyr Ile Leu Gly Thr Ile Glu Ile Leu Leu Ala Tyr Leu Phe
        195                 200                 205

Pro Ala Met Ala Ile Phe Lys Ala Glu Asp Ala Ser Gly Glu Ala Ala
    210                 215                 220

Ala Met Leu Asn Asn Met Arg Val Tyr Gly Thr Cys Val Leu Thr Cys
225                 230                 235                 240

Met Ala Thr Val Val Phe Val Gly Val Lys Tyr Val Asn Lys Phe Ala
                245                 250                 255

Leu Val Phe Leu Gly Cys Val Ile Leu Ser Ile Leu Ala Ile Tyr Ala
            260                 265                 270

Gly Val Ile Lys Ser Ala Phe Asp Pro Pro Asn Phe Pro Ile Cys Leu
        275                 280                 285

Leu Gly Asn Arg Thr Leu Ser Arg His Gly Phe Asp Val Cys Ala Lys
    290                 295                 300

Leu Ala Trp Glu Gly Asn Glu Thr Val Thr Thr Arg Leu Trp Gly Leu
305                 310                 315                 320

Phe Cys Ser Ser Arg Leu Leu Asn Ala Thr Cys Asp Glu Tyr Phe Thr
                325                 330                 335

Arg Asn Asn Val Thr Glu Ile Gln Gly Ile Pro Gly Ala Ala Ser Gly
            340                 345                 350

Leu Ile Lys Glu Asn Leu Trp Ser Ser Tyr Leu Thr Lys Gly Val Ile
        355                 360                 365

Val Glu Arg Arg Gly Met Pro Ser Val Gly Leu Ala Asp Gly Thr Pro
    370                 375                 380

Val Asp Met Asp His Pro Tyr Val Phe Ser Asp Met Thr Ser Tyr Phe
385                 390                 395                 400

Thr Leu Leu Val Gly Ile Tyr Phe Pro Ser Val Thr Gly Ile Met Ala
                405                 410                 415
```

Gly Ser Asn Arg Ser Gly Asp Leu Arg Asp Ala Gln Lys Ser Ile Pro
            420                 425                 430

Thr Gly Thr Ile Leu Ala Ile Ala Thr Thr Ser Ala Val Tyr Ile Ser
            435                 440                 445

Ser Val Val Leu Phe Gly Ala Cys Ile Glu Gly Val Val Leu Arg Asp
450                 455                 460

Lys Phe Gly Glu Ala Val Asn Gly Asn Leu Val Val Gly Thr Leu Ala
465                 470                 475                 480

Trp Pro Ser Pro Trp Val Ile Val Ile Gly Ser Phe Phe Ser Thr Cys
                485                 490                 495

Gly Ala Gly Leu Gln Ser Leu Thr Gly Ala Pro Arg Leu Leu Gln Ala
            500                 505                 510

Ile Ser Arg Asp Gly Ile Val Pro Phe Leu Gln Val Phe Gly His Gly
            515                 520                 525

Lys Ala Asn Gly Glu Pro Thr Trp Ala Leu Leu Leu Thr Ala Cys Ile
530                 535                 540

Cys Glu Ile Gly Ile Leu Ile Ala Ser Leu Asp Glu Val Ala Pro Ile
545                 550                 555                 560

Leu Ser Met Phe Phe Leu Met Cys Tyr Met Phe Val Asn Leu Ala Cys
                565                 570                 575

Ala Val Gln Thr Leu Leu Arg Thr Pro Asn Trp Arg Pro Arg Phe Arg
            580                 585                 590

Tyr Tyr His Trp Thr Leu Ser Phe Leu Gly Met Ser Leu Cys Leu Ala
            595                 600                 605

Leu Met Phe Ile Cys Ser Trp Tyr Tyr Ala Leu Val Ala Met Leu Ile
            610                 615                 620

Ala Gly Leu Ile Tyr Lys Tyr Ile Glu Tyr Arg Gly Ala Glu Lys Glu
625                 630                 635                 640

Trp Gly Asp Gly Ile Arg Gly Leu Ser Leu Ser Ala Ala Arg Tyr Ala
                645                 650                 655

Leu Leu Arg Leu Glu Glu Gly Pro Pro His Thr Lys Asn Trp Arg Pro
            660                 665                 670

Gln Leu Leu Val Leu Val Arg Val Asp Gln Asp Gln Asn Val Val His
            675                 680                 685

Pro Gln Leu Leu Ser Leu Thr Ser Gln Leu Lys Ala Gly Lys Gly Leu
            690                 695                 700

Thr Ile Val Gly Ser Val Leu Glu Gly Thr Phe Leu Asp Asn His Pro
705                 710                 715                 720

Gln Ala Gln Arg Ala Glu Glu Ser Ile Arg Arg Leu Met Glu Ala Glu
                725                 730                 735

Lys Val Lys Gly Phe Cys Gln Val Val Ile Ser Ser Asn Leu Arg Asp
            740                 745                 750

Gly Val Ser His Leu Ile Gln Ser Gly Gly Leu Gly Gly Leu Gln His
            755                 760                 765

Asn Thr Val Leu Val Gly Trp Pro Arg Asn Trp Arg Gln Lys Glu Asp
            770                 775                 780

His Gln Thr Trp Arg Asn Phe Ile Glu Leu Val Arg Glu Thr Thr Ala
785                 790                 795                 800

Gly His Leu Ala Leu Leu Val Thr Lys Asn Val Ser Met Phe Pro Gly
                805                 810                 815

Asn Pro Glu Arg Phe Ser Glu Gly Ser Ile Asp Val Trp Trp Ile Val
            820                 825                 830

His Asp Gly Gly Met Leu Met Leu Leu Pro Phe Leu Leu Arg His His

```
                835                 840                 845
Lys Val Trp Arg Lys Cys Lys Met Arg Ile Phe Thr Val Ala Gln Met
    850                 855                 860

Asp Asp Asn Ser Ile Gln Met Lys Lys Asp Leu Thr Thr Phe Leu Tyr
865                 870                 875                 880

His Leu Arg Ile Thr Ala Glu Val Glu Val Val Met His Glu Ser
                885                 890                 895

Asp Ile Ser Ala Tyr Thr Tyr Glu Lys Thr Leu Val Met Glu Gln Arg
                900                 905                 910

Ser Gln Ile Leu Lys Gln Met His Leu Thr Lys Asn Glu Arg Glu Arg
            915                 920                 925

Glu Ile Gln Ser Ile Thr Asp Glu Ser Arg Gly Ser Ile Arg Arg Lys
        930                 935                 940

Asn Pro Ala Asn Thr Arg Leu Arg Leu Asn Val Pro Glu Glu Thr Ala
945                 950                 955                 960

Cys Asp Asn Glu Glu Lys Pro Glu Glu Val Gln Leu Ile His Asp
                965                 970                 975

Gln Ser Ala Pro Ser Cys Pro Ser Ser Ser Pro Ser Pro Gly Glu Glu
            980                 985                 990

Pro Glu Gly Glu Gly Glu Thr Asp  Pro Glu Lys Val His  Leu Thr Trp
        995                 1000                1005

Thr Lys  Asp Lys Ser Ala Ala  Gln Lys Asn Lys  Gly Pro Ser Pro
    1010                1015                1020

Val Ser  Ser Glu Gly Ile Lys  Asp Phe Phe Ser Met  Lys Pro Glu
    1025                1030                1035

Trp Glu  Asn Leu Asn Gln Ser  Asn Val Arg Arg Met  His Thr Ala
    1040                1045                1050

Val Arg  Leu Asn Glu Val Ile  Val Asn Lys Ser Arg  Asp Ala Lys
    1055                1060                1065

Leu Val  Leu Leu Asn Met Pro  Gly Pro Pro Arg Asn  Arg Asn Gly
    1070                1075                1080

Asp Glu  Asn Tyr Met Glu Phe  Leu Glu Val Leu Thr  Glu Gln Leu
    1085                1090                1095

Asp Arg  Val Met Leu Val Arg  Gly Gly Gly Arg Glu  Val Ile Thr
    1100                1105                1110

Ile Tyr  Ser
    1115

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
tctccttggg attgccgtca                                              20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
tcttcttgag actgcagtca                                              20
```

METHOD FOR IDENTIFYING COMPOUNDS FOR TREATMENT OF PAIN

CROSS REFERENCE TO RELATED APPLICATIONS

This application is a divisional application of U.S. patent application Ser. No. 10/556,221 filed Apr. 17, 2006, now pending, which is the 371 National Phase of International Application No. PCT/CA2004/000726, filed May 14, 2004, which was published in English under PCT Article 21(2) as International Publication No. WO 2004/101072. This application further claims the benefit, under 35 U.S.C. §119(e), of U.S. provisional patent application Ser. No. 60/470,885 filed May 16, 2003. All of these applications are incorporated herein by reference in their entirety.

FIELD OF THE INVENTION

The invention relates to the modulation of anion levels in a central nervous system (CNS) neural cell, and particularly relates to the modulation of CNS intracellular chloride levels and uses thereof for treating, preventing, diagnosing and prognosticating pain.

BACKGROUND OF THE INVENTION

The need for new and improved methods and agents for pain treatment is a significant ongoing concern in medicine. Acute pain, e.g. related to injury or disease, can be severe and have critical effects on patient recovery. An even greater concern is chronic pain, which affects a large proportion of the population, causing not only significant discomfort, but can result in low self-esteem, depression, anger, and can interfere with or completely prevent sufferer from typical daily activities.

While a number of studies have been done in this area, many mechanisms and pathways involved in pain sensation remain poorly understood. As in the case of the sensation of various stimuli, it has been suggested that pain sensation is related to altered neuronal excitability.

Ion cotransport has in some cases been thought to play a role in the processing of certain stimuli. For example, Howard et al. (28) have demonstrated that mice generated with a targeted deletion of the Slc12a6 gene, which encodes the KCC3 exporter, exhibit features of agenesis of the corpus callosum, including a locomotor deficit, peripheral neuropathy and a sensorimotor gating deficit. Sung et al. (29) report that in mice where there is a disruption of the Slc12a2 gene, which encodes the NKCC1 cotransporter, sensitivity to thermal stimulus is greatly reduced, compared to both wild-type and heterozygous (NKCC1$^{+/-}$) mice.

There remains a need to better define the mechanisms involved in pain sensation to provide new strategies of therapeutic intervention in this regard.

SUMMARY OF THE INVENTION

This invention relates to pain and methods of treating, preventing, diagnosing and prognosticating such pain. This invention also relates to pain associated with neuropathic pain and CNS dysfunction. This invention also relates to methods of decreasing an intracellular chloride level in a central nervous system (CNS) neural cell.

According to one aspect, the invention provides a method of treating or preventing pain in a subject, the method comprising decreasing an intracellular chloride level in a central nervous system (CNS) neural cell of the subject. In an embodiment, the method comprises modulating the activity or expression of a chloride transporter in the CNS cell, thereby to decrease the chloride level. In a further embodiment, the chloride transporter is KCC2 the method comprises increasing KCC2 activity or expression. In another embodiment, the CNS neural cell is a spinal cord neural cell. In yet another embodiment, the signal of the pain originates in a peripheral nervous system (PNS) cell or sensory fiber trans-synaptic to the CNS neural cell. In still another embodiment, the pain is neuropathic pain, and in further embodiments the neuropathic pain is associated with a nerve or tract injury or is selected from the group consisting of somatic and visceral pain. In yet another embodiment, the pain is selected from the group consisting of chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury and recurrent acute pain.

In an embodiment, the method comprises administering to the subject a compound capable of decreasing the intracellular chloride level in the CNS cell. In yet another embodiment, the compound is capable of modulating the activity or expression of a chloride transporter in the CNS cell. In yet a further embodiment, the chloride transporter is KCC2, and yet further, the compound is capable of increasing KCC2 activity or expression. In another embodiment, the compound is an inhibitor of TrkB, such as K-252a or an anti-TrkB antibody. In another embodiment, the compound is an inhibitor of cyclic AMP-dependent kinase (PKA) (e.g. H-89). In another embodiment, the compound is an inhibitor of calmodulin-dependant kinase (CAM kinase), and further, it is KN-93. In an embodiment, KCC2 comprises an amino acid sequence substantially identical to a sequence selected from the group consisting of SEQ ID NO: 2, 4, 6 and a fragment thereof.

According to another aspect of the present invention, there is provided a composition for the treatment or the prevention of pain in a subject, the composition comprising a compound capable of decreasing an intracellular chloride level in a CNS neural cell; and a pharmaceutically acceptable carrier. In an embodiment, the compound is capable of modulating the activity or expression of a chloride transporter in the CNS neural cell. In a further embodiment, the chloride transporter is KCC2, and further, the compound is capable of increasing KCC2 activity or expression.

According to still another aspect of the invention, there is provided a commercial package comprising the composition described herein together with instructions for its use in the treatment or prevention of pain.

According to yet another aspect of the invention, there is provided a commercial package comprising a compound capable of decreasing an intracellular chloride level in a CNS neural cell together with instructions for its use the treatment or prevention of pain. In an embodiment, the compound is capable of modulating the activity or expression of a chloride transporter in said CNS neural cell. In a further embodiment, the chloride transporter is KCC2, and further, the compound is capable of increasing said KCC2 activity or expression.

According to a further aspect of the present invention, there is provided use of the composition described herein for the treatment or prevention of pain and/or for the preparation of a medicament for the treatment or prevention of pain.

According to yet a further aspect of the present invention, there is provided use of a compound capable of decreasing an intracellular chloride level in a CNS neural cell for the treatment or prevention of pain and/or for the preparation of a medicament for the treatment or prevention of pain. In an embodiment, the compound is capable of modulating the activity or expression of a chloride transporter in said CNS cell. In a further embodiment, the chloride transporter is KCC2, and further, the compound is capable of increasing KCC2 activity or expression. In another embodiment, the compound is an inhibitor of TrkB, and further, it is selected from the group consisting of K-252a and an anti-TrkB antibody. In another embodiment, the compound is an inhibitor of cyclic AMP-dependent kinase (PKA), and further, it is H-89. In another embodiment, the compound is an inhibitor of calmodulin-dependant kinase, and further, it is KN-93.

According to still a further aspect of the invention, there is provided a method of identifying or characterizing a compound for treatment or prevention of pain, the method comprising contacting a test compound with a CNS-derived cell; and determining whether the intracellular chloride level is decreased in the presence of the test compound; wherein the decrease is an indication that the test compound may be used for treatment or prevention of pain.

According to another aspect of the present invention, there is provided a method of identifying or characterizing a compound for treatment or prevention of pain, the method comprising contacting a test compound with a CNS-derived cell expressing a chloride transporter; and determining whether activity or expression of the chloride transporter is modulated in the presence of the test compound in such a way that the level intracellular chloride is decreased; wherein the modulation is an indication that the test compound may be used for treatment or prevention of pain. In an embodiment, the chloride transporter is KCC2, and further, the method comprises determining whether said KCC2 expression or activity is increased in the presence of the test compound and the modulation is an increase. In another embodiment, KCC2 activity is determined by measuring a parameter selected from the group consisting of potassium transport, chloride transport, intracellular chloride level and anion reversal potential. In still another embodiment, the pain is selected from the group consisting of chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury and recurrent acute pain.

According to yet another aspect of the present invention, there is provided a method of identifying or characterizing a compound for treatment or prevention of pain, said method comprising contacting a test compound with, a CNS-derived cell comprising a first nucleic acid comprising a transcriptionally regulatory element normally associated with a chloride transporter gene, operably linked to a second nucleic acid comprising a reporter gene capable of encoding a reporter protein; and determining whether reporter gene expression or reporter protein activity is modulated in the presence of the test compound; wherein the modulation in reporter gene expression or reporter protein activity being an indication that the test compound may be used for treatment or prevention of pain. In a further embodiment, the chloride transporter is KCC2, and further, the reporter gene expression or reporter protein activity is increased in the presence of the test compound.

According to one aspect of the present invention, there is provided a method for decreasing nociception in a subject, the method comprising decreasing intracellular chloride in a CNS neural cell of the subject. In an embodiment, the method comprises modulating chloride transporter activity or expression in the CNS neural cell. In a further embodiment, the chloride transporter is KCC2, and further, the method comprises increasing KCC2 activity or expression. In another embodiment, the method further comprises contacting the CNS neural cell with a compound capable of increasing KCC2 activity or expression. In yet another embodiment, the compound is an inhibitor of TrkB, and further, it is selected from the group consisting of K-252a and an anti-TrkB antibody. In still another embodiment, the compound is an inhibitor of cyclic AMP-dependent kinase (PKA), and further, it is H-89. In yet another embodiment, the compound is an inhibitor of calmodulin-dependant kinase, and further, it is KN-93. In still another embodiment, KCC2 comprises an amino acid sequence substantially identical to a sequence selected from the group consisting of SEQ ID NO: 2, 4, 6 and a fragment thereof.

According to another aspect of the invention, there is provided a method for diagnosing or prognosticating pain associated with CNS dysfunction in a subject experiencing pain, the method comprising determining whether a test CNS intracellular chloride level is increased relative to a corresponding control chloride level; wherein the increase is an indication that the subject is experiencing pain associated with CNS dysfunction. In an embodiment, the method further comprises determining whether CNS chloride transporter activity or expression is modulated relative to a control transporter activity or expression. In another embodiment, the chloride transporter is KCC2, and further, the method comprises determining whether KCC2 activity or expression is decreased relative to the control activity or expression. In still another embodiment, the control intracellular chloride level is selected from the group consisting of an established standard; a corresponding intracellular chloride level determined in the subject at an earlier time; a corresponding intracellular chloride level determined in the subject when the subject is experiencing less pain or substantially no pain; and a corresponding intracellular chloride level determined in a control subject experiencing less pain or substantially no pain. In yet another embodiment, the control activity or expression is selected from the group consisting of an established standard of KCC2 activity or expression; a corresponding level of KCC2 activity or expression determined in the subject at an earlier time; a corresponding level of KCC2 activity or expression determined in the subject when the subject is experiencing less pain or substantially no pain; and a corresponding level of KCC2 activity or expression determined in a control subject experiencing less pain or substantially no pain. In a further embodiment, KCC2 activity is determined by measuring a parameter selected from the group consisting of potassium transport, chloride transport, intracellular chloride level and anion reversal potential. In still a further embodiment, the intracellular chloride level is determined by administering an indicator compound indicative of chloride level to the subject such that it is contacted with a CNS neural cell of the subject; and assessing an in vivo signal associated with the indicator compound. In yet another embodiment, the pain associated with CNS dysfunction is neuropathic pain. In still yet another embodiment, the indicator compound is a radionuclide, and further, it is selected from the group consisting of $^{201}$Tl, $^{99}$Tcm-tetrofosmin, $^{99}$Tcm-MIBI, $^{99}$Tcm-HMPAO and $^{36}$Cl. In still another embodiment, the in vivo signal is assessed by an imaging technique. In yet still another embodiment, the in vivo signal is the retention index of the indicator compound. In a further embodiment, the imaging technique is selected from the group consisting of single photon emission computed tomography, positron emission tomography and magnetic resonance imaging. In yet a further embodiment, the indicator compound is indicative of KCC2 expression, and further, it is an antibody directed against KCC2.

According to yet another aspect of the invention, there is provided a method of treating pain associated with CNS dysfunction in a subject, the method comprising diagnosing or prognosticating, according to the methods described herein, pain associated with CNS dysfunction in the subject; and decreasing an intracellular chloride level in a CNS cell of the subject.

In an embodiment, the above-mentioned subject is a mammal, in a further embodiment, a human.

BRIEF DESCRIPTION OF THE DRAWINGS

FIG. 9: Polypeptide (SEQ ID NO: 2; FIG. 9A) and DNA (SEQ ID NO: 1; FIGS. 9A-9C) sequences of human KCC2.

FIG. 10: Polypeptide (SEQ ID NO: 4; FIG. 10A) and DNA (SEQ ID NO: 3; FIGS. 10A-10B) sequences of mouse KCC2.

FIG. 11: Polypeptide (SEQ ID NO: 6; FIG. 11A) and DNA (SEQ ID NO: 5; FIGS. 11A-11C) sequences of rat KCC2.

DETAILED DESCRIPTION OF THE INVENTION

Figure 1A:
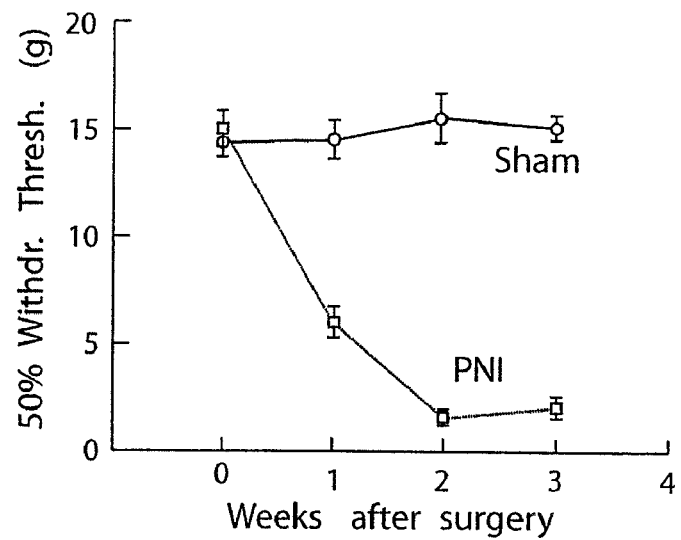
FIG. 1: Peripheral nerve injury (PNI) induced a collapse of the $V_{anion}$ in Lamina I (LI) neurons in the ipsilateral superficial dorsal horn (SDH). a) Chronic constriction injury of the sciatic nerve (n=23), but not sham surgery (n=11), caused a significant reduction in the 50% nociceptive withdrawal threshold to mechanical stimulation of the hindpaw in rats (p<0.01). b) Ranges of $E_{anion}$ recorded from LI neurons of naïve (△) and PNI (○) rats. Solid symbol=mean $E_{anion}$±SEM. c) All classes of LI neurons (i.e. with phasic (P), single-spike (SS) and tonic (T) firing properties [19]) showed a shift in $E_{anion}$ in response to PNI. Scale bar is 50 mV (y), 150 ms (x). d) Mean peak current measured in LI neurons from naïve (▲) and PNI (●) rats in response to applied GABA at various $V_m$. Horizontal standard error bars represent inter-neuron differences in recording pipette offset. Inset: Representative traces from one neuron. Scale bar is 0.6 nA (y), 1.0 s (x).

Described herein is a novel mechanism of disinhibition following peripheral nerve injury. It involves a transsynaptic disruption of anion homeostasis in neurons of lamina I of the superficial dorsal horn (SDH), one of the main spinal nociceptive output pathways (7). The resulting shift in the transmembrane anion gradient is shown herein to cause normally inhibitory anionic synaptic currents to be excitatory, substantially driving up the net excitability of lamina I neurons. As shown herein, peripheral nerve injury is sensed by transmission of a signal transsynaptically resulting in an increase in intracellular chloride levels in central nervous system (CNS) neurons. Further, the studies described herein demonstrate that decreasing CNS neuronal chloride levels can reverse this phenomenon, as shown via local blockade or knock-down of the spinal KCC2 exporter in intact rats which markedly reduced nociceptive threshold, confirming that the reported disruption of anion homeostasis in lamina I neurons was sufficient to cause neuropathic pain.

Therefore, the studies described herein have investigated the mechanism of pain sensation via the study of downstream events following peripheral nerve injury. As such, it is shown herein that such events are transmitted transsynaptically (e.g. by a peripheral nervous system (PNS cell or a sensory fiber) to central nervous system (CNS) neurons, in an embodiment, to spinal cord neurons. Further studies herein demonstrate that transmission of the nociceptive signal and sensation of pain is ultimately effected by a modulation of intracellular chloride level (e.g. modulated by a chloride transporter such as the potassium-chloride cotransporter KCC2) in a CNS tissue. KCC2 (see (37) for a review) is a potassium-chloride cotransporter which has been identified in rat, mouse and human (for human KCC2 see for example US Patent application Serial No. 20030027983 of Mount et al.; published Feb. 6, 2003). Studies of homozygous and heterozygous disruptions of the KCC2 gene in mouse revealed a seizure phenotype, suggesting a possible role for KCC2 in epilepsy (38). The precise role of KCC2 in CNS function is not yet completely understood.

Applicants demonstrate herein a correlation between the intracellular chloride level (e.g. by virtue of the activity/expression of a chloride transporter such as KCC2) in a CNS cell or tissue, and the sensation of pain. As shown in the examples below, peripheral nerve injury (PNI) results in the hyperexcitation or sensitization of CNS neurons, e.g. of the spinal cord, e.g. lamina I (LI) neurons of the superficial dorsal horn (SDH). Such hyperexcitability occurs transsynaptically (i.e. downstream from the injured peripheral neuron), a phenomenon which has not been described prior to applicants' studies herein. Such hyperexcitability results in a reduction of the nociceptive threshold.

As shown herein, the hyperexcitability noted above correlates with an increase in intracellular chloride levels (e.g. modulation [e.g. decrease] in chloride transporter [such as KCC2] activity and/or expression) in the SDH. The role of KCC2 in this regard was confirmed via administration of the KCC2 blocker DIOA or a KCC2 antisense oligonucleotide to spinal tissue, both resulting in a rapid decrease in the threshold for pain sensitivity. Therefore, a reduction in KCC2 activity and/or expression, if it results in increased CNS neuronal chloride levels, may result in a decrease in the threshold for pain sensitivity, and, conversely, an increase or induction of KCC2 activity and/or expression, if it results in a decrease in CNS neuronal chloride, may result in an increase in the threshold for pain sensitivity thus providing for prevention and treatment of pain. On the other hand, it has been reported that under certain pathophysiological conditions, e.g. where $[K^+]_o$ is elevated, KCC2 may accumulate $Cl^-$ in neurons, thereby enhancing neuronal excitability (42). Under such conditions, it is envisioned that KCC2 would have the opposite effect on CNS neuronal chloride, and thus result in an increase in CNS neuronal chloride and in turn decreased nociceptive threshold and increased pain sensation. As such, modulation of the activity and/or expression of KCC2 may, depending on the directionality of the flux of chloride ion, contribute to or alleviate a pain sensation.

Therefore, in a first aspect, the invention relates to methods and materials for the treatment of pain, based on the modulation of CNS intracellular chloride level and further the modulation of the activity and/or expression of a chloride transporter, e.g. the KCC2 potassium-chloride cotransporter. As used herein, a "chloride transporter" is defined as a polypeptide/protein or complex thereof associated with the cell membrane that is able to effect the passage of chloride anions across the cell membrane. "Export(er)" refers to a net passage from the inside to the outside of the cell, and "import (er)" refers to a net passage from the outside to the inside of the cell.

Therefore, in an embodiment, the present invention relates to methods for treating pain by decreasing the intracellular chloride level in a cell, e.g. a CNS neural cell. In a further embodiment, modulators of a chloride transporter (e.g. KCC2) can be used to decrease intracellular chloride levels. In an embodiment, the invention relates to the application, systemic or local, of compounds or drugs that decrease the intracellular level of chloride in a CNS neural cell as a means to attenuate pain. In order achieve this result, the above-mentioned compounds or drugs may modulate the function or expression of the chloride transporter (e.g. KCC2 cotransporter) in CNS neurons. In yet a further embodiment, the compounds or drugs may increase the expression or activity of the chloride transporter or KCC2.

In an embodiment, the CNS neural cell in which the intracellular chloride levels are being modulated can be located in the superficial dorsal horn or the spinal cord. In addition, the cell may also be transsynaptic to a peripheral nerve cell or sensory fiber from which a signal for pain originates.

In an embodiment, the invention also relates to the treatment of acute and chronic pain, more specifically to the treatment of neuropathic pain. "Neuropathic pain", as used herein, refers to chronic pain associated with nerve injury (e.g. following crush, transection or compression of nerves or following nerve degeneration resulting from disease). In an embodiment, neuropathic pain is associated with a nerve or tract injury. In a further embodiment, the neuropathic pain is associated with visceral and/or somatic pain. The invention further relates to decreasing CNS neuronal chloride levels (e.g. via modulation of chloride transporter [such as KCC2] activity and/or expression) to reduce nociception. "Nociception" as used herein refers to the sensory component of pain. Pain may be the result of various stimuli, including but not limited to pressure, injury, thermal stimuli or chemical (e.g. ionic) stimuli. In embodiments, the pain may be associated with many conditions such as chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury and/or recurrent acute pain. The invention also relates to methods of diagnosis and prognostication to assess pain associated with CNS dysfunction. In an embodiment, such diagnosis/prognostication may be performed prior to the method of treatment described herein, or during a treatment regimen, to further characterize the nature of the pain or its progression, and thus provide information which may be used e.g. to select a course of treatment for such pain in accordance with the results obtained from such diagnosis/prognostication. As used herein, "pain associated with CNS dysfunction" relates to a pain sensation that is caused by an alteration in ion (e.g. anion) homeostasis in a CNS tissue. In an embodiment, the anion is a chloride ion. In a further embodiment, the alteration is an increase in an intracellular chloride level in a CNS cell. In yet another embodiment, the activity or expression of a chloride transporter may be modulated (e.g. KCC2 activity or expression may be modulated [e.g. decreased]) when a subject experiences pain associated with a CNS dysfunction.

"KCC2" as used herein refers to a particular type of potassium-chloride cotransporter expressed in neurons. In embodiments, KCC2 comprises the sequence of the polypeptide of SEQ ID NOs: 2 (human KCC2; see also FIG. 9), 4 (mouse KCC2; see also FIG. 10) or 6 (rat KCC2; see also FIG. 11), fragments thereof or sequences substantially identical thereto. In further embodiments, KCC2 is encoded by the nucleic acid sequences capable of encoding the polypeptides of SEQ ID NO: 2, 4 or 6, or fragments thereof or sequences substantially identical thereto or related by hybridization criteria (see below). In further embodiments, such nucleic acid sequences comprise of SEQ ID NO: 1 (human KCC2 DNA; see also FIG. 9), 3 (mouse KCC2 DNA; see also FIG. 10) or 5 (rat KCC2 DNA; see also FIG. 11), fragments thereof or sequences substantially identical thereto or related by hybridization criteria (see below).

"Chloride transporter) activity" as used herein refers to the transport of chloride, across the cell membrane. Such transport activity may be measured by direct or indirect means using various methods known in the art, examples of which are described herein. "KCC2 activity" as used herein refers to any detectable phenotype associated with KCC2. In an embodiment, KCC2 activity includes, but is not limited to potassium transport, chloride transport, which may, for example, be determined by assessing levels (either directly or indirectly) of potassium and/or chloride inside and/or outside the cell using, for example, reversal potential measurements with patch clamping methods, chloride/potassium sensitive dyes (see for example Haugland, R. P., *Handbook of Fluorescent Probes and Research Products*, ninth ed., 2002, Molecular Probes, Inc., Eugene, Oreg., USA) electrodes, etc. In addition, KCC2 activity may also affect the neural cell's anion reversal potential ($E_{anion}$). The anion reversal potential may be determined, for example, by using gramicidin-perforated patch clamp recording.

"Chloride transporter expression" (e.g. KCC2 expression) relates both to production of a chloride transporter transcript (e.g. a KCC2 transcript) or a chloride transporter polypeptide or protein (e.g. a KCC2 polypeptide or protein). Chloride transporter expression (e.g. KCC2 expression) may therefore, in embodiments, be determined by assessing protein levels directly (e.g., by immunocytochemistry and/or western analysis) or a level of a chloride transporter-encoding nucleic acid (e.g. chloride transporter-encoding nucleic acid such as chloride transporter mRNA levels) that may be determined by using, for example, methods such as reverse-transcriptase polymerase chain reaction [RT-PCR] methods, micro-array-based methods or by Northern analysis).

Compounds capable of decreasing intracellular. chloride level in a CNS neural cell may, for example, modulate chloride transporter activity and expression (e.g. KCC2 activity and expression). In an embodiment, the chloride transporter activity or expression (e.g. KCC2 activity or expression) may be increased. In an embodiment, these compounds can be administered in a way such that they contact a CNS tissue or a CNS cell. The compounds that can be used include, but are not limited to, those which directly or indirectly modify the activity of the protein and those which modulate the production and/or stability of the protein (e.g. at the level of transcription, translation, maturation, post-translational modification, phosphorylation and degradation).

One class of such compounds are those that act via modulation of phosphorylation of one or more sites on KCC2. Upon cloning KCC2 (20), it has been reported that KCC2 does not contain consensus phosphorylation sites for PKA, yet does contain five for PKC ($Thr^{34}$, $Ser^{728}$, $Thr^{787}$, $Ser^{940}$ & $Ser^{1034}$). One consensus site was identified for tyrosine protein phosphorylation ($Tyr^{1081}$) in the carboxyl-terminal. This tyrosine kinase consensus phosphorylation site is not present in the KCC1 or KCC4 isoforms, yet it is conserved in the KCC3 protein (21). As such, compounds capable of upregulating or increasing KCC2 activity include, but are not limited to, protein kinases inhibitors (e.g. N-ethylmaleimide (23-25), staurosporine (29), and receptor tyrosine kinase inhibitors such as K-252a); antibodies or antibody fragments generated against certain kinases or kinase phosphorylation sites on KCC2, or compounds which interfere more directly (e.g. oligopeptides capable of competing with phosphorylation sites on KCC2) or less directly (e.g. compounds which modulate kinase activity and/or expression) with KCC2 phosphorylation. In an embodiment, such a compound may act at the level of phosphorylation-mediated signaling pathways and ultimately affect KCC2 phosphorylation. In another embodiment, TrkB may be modulated to affect KCC2 phosphorylation and ultimately modulate KCC2 activity. Thus, In an embodiment, compounds that inhibit TrkB activity may, for example, be used in this regard. Such compounds may include, but are not limited to, K-252a (commercially available from Calbiochem) or a neutralizing antibody against TrkB (anti-TrkB antibody [e.g. IgG])(commercially available from BD Transduction Laboratories). In yet another embodiment, modulation, e.g. inhibition, of cyclic AMP-dependant kinase or PKA may be useful in modulating KCC2 phosphorylation and ultimately be used in the treatment or prevention of pain. For example, the PKA inhibitor H-89 (commercially available from EMD Biosciences) may be used in this regard. In a further embodiment, modulation, e.g. inhibition, of calmodulin-dependant kinase (CAM kinase, e.g. II and IV) may alleviate or prevent pain in a subject by modulating KCC2 activity, e.g. phosphorylation. Compounds capable of inhibiting such a kinase include, but are not limited to, KN-93 (commercially available from EMD Biosciences). In yet another embodiment, modulators, e.g. inhibitors, of other members of the TrkB pathway, e.g. phosphatidylinositol-specific phospholipase C or phosphatidylcholine-specific phospholipase C, e.g. phospholipase C gamma (PLCγ), may be used to decrease intracellular chloride levels in a CNS neural cell. Such compounds include, but are not limited to, tricyclodecan-9-yl-xanthogenate, 1-O-octadecyl-2-O-methyl-rac-glycero-3-phosphorylcholine, neomycin sulfate, spermine tetrahydrochloride, 1-[6-((17beta-3-methoxyestra-1,3,5(10)-trien-17-yl)amino)hexyl]-1H-pyrrole-2,5-dione, or 1-[6-((17beta-3-methoxyestra-1,3,5(10)-trien-17-yl)amino)hexyl]-2,5-pyrrolidinedione.

Further, modulation of KCC2 expression may also arise from modulation (e.g. mediated by phosphorylation) of transcription factors which regulate KCC2 expression. In a further aspect, the invention provides a method for treating pain or preventing/decreasing nociception in a subject or animal, comprising modulating, in embodiments reducing or decreasing, intracellular chloride levels in a CNS neuron or tissue. In an embodiment, such decrease in intracellular chloride levels is achieved by modulating, e.g. decreasing, activity or expression of a chloride transporter (e.g. KCC2) in a CNS neuron or tissue of the subject. In a further embodiment, the subject is a vertebrate. In another embodiment, the subject is a mammal, in a yet further embodiment, a human. In an embodiment, the CNS tissue is spinal cord tissue and the neural cell is a spinal cord neural cell.

Accordingly, the invention therefore provides methods of treating pain comprising administering a compound capable of modulating, in an embodiment, decreasing or reducing intracellular chloride levels in CNS tissue (e.g. a CNS neural cell) in a subject. In an embodiment, the modulation, e.g. increase, in chloride transporter (e.g. KCC2) activity and/or expression effects the decrease in intracellular chloride level in the subject. In an embodiment, the CNS tissue is spinal cord tissue and the neural cell is a spinal cord neural cell.

In an embodiment, KCC2 comprises an amino acid sequence substantially identical to a sequence set forth in SEQ ID NO: 2, 4, 6 or a fragment thereof. In another embodiment, KCC2 may be encoded by a nucleic acid substantially identical to a nucleotide sequence capable of encoding SEQ ID NO: 2, 4, 6 or a fragment thereof, such as a sequence substantially identical to the sequence set forth in SEQ ID NO: 1, 3, 5 or a fragment thereof.

As noted above, a homolog, variant and/or fragment of a KCC2 which retains activity may also be used in the methods of the invention. Homologs include protein sequences which are substantially identical to the amino acid sequence of a KCC2, sharing significant structural and functional homology with a KCC2. Variants include, but are not limited to, proteins or peptides which differ from a KCC2 by any modifications, and/or amino acid substitutions, deletions or additions. Modifications can occur anywhere including the polypeptide backbone, (i.e. the amino acid sequence), the amino acid side chains and the amino or carboxy termini. Such substitutions, deletions or additions may involve one or more amino acids. Fragments include a fragment or a portion of a KCC2 or a fragment or a portion of a homolog or variant of a KCC2.

With regard to increasing or upregulating expression of KCC2 in a cell, various methods of introducing KCC2-encoding nucleic acids into the cell may be used, examples of which are described below. Methods such as the gene therapy methods discussed below may be used in this regard. Examples of KCC2-encoding nucleic acids include nucleic acids capable of encoding a polypeptide of SEQ ID NO: 2, 4 or 6 (e.g. the nucleic acids of SEQ ID NO: 1, 3 and 5), or nucleic acids substantially identical thereto. The method may also comprise administering to an area or neural tissue, e.g. CNS tissue, a cell comprising such a KCC2-encoding nucleic acid, via for example transplantation or introduction of a neural cell or precursor thereto (e.g. a stem cell) comprising such a KCC2-encoding nucleic acid. Further, the method may entail administering to the subject a compound capable of modulating, e.g. unpregulating or increasing, expression of a KCC2. Such a compound may for example be identified and characterized by the screening methods described below. Such a compound may further be provided as a composition comprising the compound and a pharmaceutically acceptable carrier. In an embodiment, the composition is formulated for or adapted for administration to the CNS. Such a compound or composition may be provided in a commercial package together with instructions for its use.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term "homologous" does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with any of SEQ ID NO: 1 to 6.

Substantially complementary nucleic acids are nucleic acids in which the "complement" of one molecule is substantially identical to the other molecule. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in, both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing, in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

According to a further aspect, the invention also provides a method for decreasing nociception in a subject. In an embodiment, this method comprises modulating, e.g. decreasing, intracellular chloride levels in a cell, e.g. a CNS cell, in a subject. In a further embodiment, the method also comprises modulating, e.g. increasing, chloride transporter activity or expression, e.g. KCC2 activity or expression. In yet another embodiment, the method also comprises contacting the CNS neural cell with a compound capable of modulating chloride transporter activity. Such compounds include, but are not limited to a TrkB inhibitor (such as K-252a or anti-TrkB antibody), a PKA inhibitor (such as H-89) or a CAM kinase inhibitor (such as KN-93).

The invention further provides a composition for the prevention and/or treatment of pain comprising a compound capable of modulating, e.g. decreasing, intracellular chloride levels in admixture with a pharmaceutically acceptable carrier. In an embodiment, such composition may modulate, e.g. increase or upregulate, chloride transporter activity, e.g. KCC2, activity and/or expression. In an embodiment, such a composition is suitable for or adapted for administration to a CNS neural cell or tissue, such as spinal cord tissue or cell. In yet a further embodiment, such a composition may be an inducer of KCC2 expression or activity. As used herein, an "inducer" is a compound that upregulates or enhances directly or indirectly the expression of the KCC2 gene, stability of the KCC2 mRNA, translation of the KCC2 mRNA, maturation of the KCC2 polypeptide, transport, e.g. recycling, of the KCC2 polypeptide to the cell membrane, or transporter activity of the KCC2 polypeptide. In an embodiment, the "inducer" can also down-regulate or inhibit KCC2 inhibitors.

The invention further provides a use of the above-mentioned composition or the above-mentioned compound, capable of modulating, e.g. decreasing, intracellular chloride levels for the treatment or prevention of pain. The invention also provides a use of the above-mentioned composition or the above-mentioned compound, capable of modulating, e.g. decreasing, intracellular chloride levels for the preparation of a medicament for treatment or prevention of pain. In an embodiment, the compound or composition modulates, e.g. increases or upregulates, chloride transporter (e.g. KCC2) activity and/or expression. In yet another embodiment, the compound or composition may comprise a TrkB inhibitor (such as K-252a or anti-TrkB antibody), a PKA inhibitor (such as H-89) or a CAM kinase inhibitor (such as KN-93). In yet another embodiment, the medicament may be formulated for administration to a CNS tissue, e.g. CNS cell, of a subject. Further, the compound may be, for example, an inducer of KCC2 expression or activity.

The invention further provides commercial packages comprising a compound capable of modulating, e.g. decreasing, intracellular chloride levels or the above-described composition together with instructions for its use in the treatment or prevention of pain. In an embodiment, the compound may modulate, e.g. increase or upregulate, chloride transporter or KCC2 activity and/or expression.

In various embodiments, a compound capable of modulating, e.g. decreasing, intracellular chloride levels in a CNS cell may be used therapeutically in formulations or medicaments to treat pain. The compound may, for example, modulate, e.g. increase or upregulate chloride transporter (e.g. KCC2) activity and/or expression. The invention also provides corresponding methods of medical treatment, in which a therapeutic dose of a compound capable of modulating, in an embodiment decreasing, intracellular chloride levels, is administered in a pharmacologically acceptable formulation. Accordingly, the invention also provides therapeutic compositions comprising a compound capable of modulating, in an embodiment decreasing intracellular chloride levels, and a pharmacologically acceptable excipient or carrier. The therapeutic composition may be soluble in an aqueous solution at a physiologically acceptable pH.

In an embodiment, a compound of the invention is administered such that it comes into contact with a CNS tissue or a CNS neuron. As used herein, the "central nervous system" or CNS is the portion of the nervous system comprising the brain and the spinal cord (e.g. in the lumbar region). By contrast, the "peripheral nervous system" or PNS is the portion of the nervous system other than the brain and the spinal cord. In an embodiment, the CNS tissue is the superficial dorsal horn, in a further embodiment, a lamina I neuron. As such, in embodiments a compound of the invention can be administered to treat CNS cells in vivo via direct intracranial or intrathecal injection or injection into the cerebrospinal fluid. Alternatively, the compound can be administered systemically (e.g. intravenously, or orally) in a form capable of crossing the blood brain barrier and entering the CNS. "Neural" and "neuronal" are used herein interchangeably and both relate to neurons and the nervous system.

The invention also provides pharmaceutical compositions (medicaments) comprising a compound capable of modulating, in an embodiment decreasing intracellular chloride levels in a CNS cell. In an embodiment, such compositions include the compound, in a therapeutically or prophylactically effective amount sufficient to treat or attenuate pain, and a pharmaceutically acceptable carrier. A "therapeutically effective amount" refers to an amount effective, at dosages and for periods of time necessary, to achieve the desired therapeutic result, such as reduction of pain. A therapeutically effective amount of a compound capable of modulating, in an embodiment decreasing, intracellular chloride levels in a CNS cell, may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount-effective, at dosages and for periods of time necessary, to achieve the desired prophylactic result, such as preventing or inhibiting onset of pain or increases in the severity of pain. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, intracranial, intrathecal, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compound capable of modulating, in an embodiment increasing or upregulating, KCC2 activity and/or expression, can be administered in a time release formulation, for example in a composition which includes a slow release polymer. The active compounds can be prepared with carriers that will protect the compound against rapid release, such as a controlled release formulation; including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. a compound capable of modulating, in an embodiment decreasing, intracellular chloride levels in a CNS cell) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, a compound capable of modulating, in an embodiment decreasing, intracellular chloride levels in a CNS cell, may be formulated with one or more additional compounds that enhance its solubility.

In accordance with another aspect of the invention, therapeutic compositions of the present invention, comprising a compound capable of modulating, in an embodiment decreasing, intracellular chloride levels in a CNS cell, may be provided in containers or commercial packages which further comprise instructions for their use for the treatment of pain.

Given that a decreased intracellular chloride level in a cell is associated with a modulation, e.g. an increase, in level/activity of chloride transporter (KCC2), which further correlates with a decrease in pain sensation as described herein, a further aspect of the present invention is the treatment of pain by administering to a subject (e.g. to CNS tissue) a nucleic acid molecule encoding a KCC2, or a variant or fragment thereof which retains KCC2 activity. Suitable methods of administration include gene therapy methods.

A nucleic acid of the invention may be delivered to cells in vivo using methods such as direct injection of DNA, receptor-mediated DNA uptake, viral-mediated transfection or non-viral transfection and lipid based transfection, all of which may involve the use of gene therapy vectors. Direct injection has been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) J. Biol. Chem. 263: 14621; Wilson et al. (1992) J. Biol. Chem. 267:963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126). Defective retroviruses are well characterized for use as gene therapy vectors (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include .psi.Crip, .psi.Cre, .psi.2 and .psi.Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

For use as a gene therapy vector, the genome of an adenovirus may be manipulated so that it encodes and expresses a polypeptide compound of the invention, but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld at al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle-cells (Quantin et al. (1992) Proc. Natl. Acad. Sci. USA 89:2581-2584).

Adeno-associated virus (AAV) may be used as a gene therapy vector for delivery, of DNA for gene therapy purposes. AAV is a naturally occurring defective virus that requires another virus, such as an adenovirus or a herpes virus, as a helper virus for efficient replication and a productive life cycle (Muzyczka et al. Curr. Topics in Micro. and Immunol. (1992) 158:97-129). AAV may be used to integrate DNA into non-dividing cells (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). An AAV vector such as that described in Tratschin et al. (1985) Mol. Cell. Biol. 5:3251-3260 may be used to introduce DNA into cells (see for example Hermonat et al. (1984) Proc. Natl. Acad. Sci. USA 81:6466-6470; Tratschin at al. (1985) Mol. Cell. Biol. 4:2072-2081; Wondisford et al. (1988) Mol. Endocrinol. 2:32-39; Tratschin at al. (1984) J. Virol. 51:611-619; and Flotte et al. (1993) J. Biol. Chem. 268:3781-3790). Lentiviral gene therapy vectors may also be adapted for use in the invention.

General methods for gene therapy are known in the art. See for example, U.S. Pat. No. 5,399,346 by Anderson et al. A biocompatible capsule for delivering genetic material is described in PCT Publication WO 95/05452 by Baetge et al. Methods of gene transfer into hematopoietic cells have also previously been reported (see Clapp, D. W., et al., Blood 78: 1132-1139 (1991); Anderson, Science 288:627-9 (2000); and Cavazzana-Calvo et al., Science 288:669-72 (2000)). The invention further relates to transplantation methods, to introduce into a subject a cell comprising a nucleic acid capable of encoding a KCC2, or to introduce into a subject a cell which has been treated in vitro or ex vivo with a compound capable of decreasing intracellular chloride levels (e.g. by culturing the cell in an appropriate medium comprising the compound). In an embodiment, such a cell is a neural cell or a precursor thereof, e.g. a stem cell capable of developing/differentiating into a neural cell (neuron progenitor cell). Methods relating to neural stem cell isolation, proliferation, characterization and/or transplantation are described in for example U.S. Pat. Nos. 5,851,832; 5,968,829; 5,411,883; 5,750,376; 6,040,180; 5,753,506 and 6,001,654. The nucleic acid may be present in a vector as described above, the vector being introduced into the cell in vitro, using for example the methods described above. In an embodiment, the cell is autologous, and is obtained from the subject. In embodiments, the cell is allogeneic or xenogeneic.

Given the correlation between intracellular chloride levels in a CNS cell and pain, compounds which are capable of modulating, e.g. decreasing, intracellular chloride levels in a CNS cell can be used for the prevention and treatment of pain. In an embodiment, compounds that modulate, e.g. increase or upregulate, chloride transporter, such as KCC2, activity/expression can be used for decreasing intracellular chloride levels and ultimately prevent or treat pain. Therefore, the invention further relates to screening methods for the identification and characterization of compounds capable of modulating intracellular chloride levels and/or chloride transporter activity and/or expression. Therefore, the invention further provides a method of determining whether a candidate compound is capable of modulating intracellular chloride levels in a cell, and in turn is useful for the prevention and treatment of pain. In an embodiment, the method comprises contacting a CNS-derived cell with said candidate compound and determining whether the intracellular chloride level has decreased in the presence of the test compound. A decrease in intracellular chloride level is indicative that the test compound may be used for the treatment or the prevention of pain. As used herein, a "CNS-derived cell" is a cell isolated or derived from a CNS tissue, and in embodiments includes both primary neuronal cultures, immortalized neuronal cell lines, as well as accepted in vitro neuronal model systems (e.g. cells differentiated into neurons in vitro). In an embodiment, the above-mentioned cell possesses a chloride transporter or KCC2 activity. In yet a further embodiment, the cell endogenously expresses a chloride transporter (e.g. KCC2). In a further embodiment the above-mentioned cell has been genetically engineered to express a chloride transporter gene or a KCC2 gene. In an embodiment, the cell may be an appropriate host cell comprising an exogenously introduced source of a chloride transporter, such as KCC2. Such a host cell may be prepared by the introduction of nucleic acid sequences encoding a chloride transporter or KCC2 into the host cell and providing conditions for the expression of such nucleic acid. In an embodiment, such a nucleic acid is DNA. Such host cells may be eukaryotic, such as amphibian or mammalian cells. In an embodiment, such host cells are human.

The invention also provides another method for the identification or characterization of compounds useful for the treatment and prevention of pain. In an embodiment, the method comprises contacting a CNS-derived cell with the candidate compound and determining whether chloride transporter activity has been modulated in the presence of the test compound. A modulation, e.g. increase, in chloride transporter activity is indicative that the test compound may be used for the treatment or the prevention of pain. In an embodiment, the chloride transporter is KCC2. KCC2 activity may be determined, for example, by measuring potassium transport, chloride transport, intracellular chloride levels and anion reversal potential.

The above-mentioned methods may be employed either with a single test compound or a plurality or library (e.g. a combinatorial library) of test compounds. In the latter case, synergistic effects provided by combinations of compounds may also be identified and characterized. The above-mentioned compounds may be used for prevention and/or treatment of pain, or may be used as lead compounds for the development and testing of additional compounds having improved specificity, efficacy and/or pharmacological (e.g. pharmacokinetic) properties. In an embodiment the compound may be a prodrug which is altered into its active form at the appropriate site of action, e.g. in CNS tissue (e.g. in the spinal cord). In certain embodiments, one or a plurality of the steps of the screening/testing methods of the invention may be automated.

As noted above, the invention further relates to methods for the identification and characterization of compounds capable of modulating, in an embodiment increasing, chloride transporter, e.g. KCC2, gene expression. Such a method may comprise assaying chloride transporter, e.g. KCC2, gene expression in the presence versus the absence of a test compound. Such gene expression may be measured by detection of the corresponding RNA or protein, or via the use of a suitable reporter construct comprising a transcriptional regulatory element(s) normally associated with such chloride transporter or KCC2 gene, operably-linked to a reporter gene. A first nucleic acid sequence may "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of protein coding sequences with which they are operably-linked. The expression of such a reporter gene may be measured on the transcriptional or translational level, e.g. by the amount of RNA or protein produced. RNA may be detected by for example Northern analysis or by the reverse transcriptase-polymerase chain reaction (RT-PCR) method (see for example Sambrook et al (1989) Molecular Cloning: A Laboratory Manual (second edition), Cold Spring Harbor Laboratory Press, Cold Spring Harbor, N.Y., USA). Protein levels may be detected either directly using affinity reagents (e.g. an antibody or fragment thereof [for methods, see for example Harlow, E. and Lane, D (1988) *Antibodies: A Laboratory Manual*, Cold Spring Harbor Laboratory Press, Cold Spring Harbor, N.Y.]; a ligand which binds the protein) or by other properties (e.g. fluorescence in the case of green fluorescent protein) or by measurement of the protein's activity, which may entail enzymatic activity to produce a detectable product (e.g. with altered spectroscopic properties) or a detectable phenotype (e.g. alterations in cell growth). Suitable reporter genes include but are not limited to chloramphenicol acetyltransferase, beta-D galactosidase, luciferase, or green fluorescent protein. In an embodiment, a candidate compound may further be assayed to determine if it is capable of modulating a chloride transporter-mediated process (e.g. KCC2-mediated process) or chloride transporter activity (e.g. KCC2 activity). In an embodiment, such chloride transporter-mediated process is ion transport, e.g. potassium or chloride transport, as determined by for example by assessing potassium and/or chloride levels (e.g. intracellularly) or by measuring anion reversal potential (electrophysiologically), membrane potential, for example as described in the examples below.

The invention also relates to the diagnosis and prognostication of pain. In an embodiment, the pain is caused by an alteration in ion, e.g. anion or chloride, homeostasis in the nervous system, e.g. central nervous system, of a subject. Without wishing to being bound to any particular theory, a reduced capacity of potassium and chloride export from neurons in the central nervous system (CNS) may lead to persistent neuronal hyperexcitability and ultimately pain.

The invention thus provides a method for diagnosing or prognosticating pain associated with CNS dysfunction. As used herein, "CNS dysfunction" is an alteration in neuronal ionic homeostasis in the CNS. In an embodiment, the pain associated with such CNS dysfunction is neuropathic pain. In an embodiment, the method comprises determining an intracellular chloride level in a CNS neural cell and comparing the chloride level to a corresponding control level. In this particular method, an increase in the test level relative to a control level is an indication that the subject is experiencing pain associated with CNS dysfunction. In an embodiment, the method may comprise determining whether CNS chloride transporter activity or expression (e.g. KCC2 activity or expression) is modulated, e.g. upregulated or increased, relative to a control activity or expression. In yet another embodiment, the control chloride level can be selected from an established standard, a corresponding chloride level determined in the subject at an earlier time; a corresponding chloride level determined in said subject when the subject is experiencing less pain (relative to the current sensation of pain noted above) or substantially no pain; or a corresponding chloride level determined in a control subject experiencing less pain (relative to the current sensation of pain in the test subject noted above) or substantially no pain. In an embodiment, a subject or control subject experiencing less pain or substantially no pain presents no evident lesions to his central or peripheral nervous system (e.g. neuropathic pain) or persistent pain. In yet another embodiment, the control activity or expression can be selected amongst an established standard of KCC2 activity or expression; a corresponding level of KCC2 activity or expression determined in the subject at an earlier time; a corresponding level of KCC2 activity or expression determined in the subject when the subject is experiencing less pain (as above) or substantially no pain; or a corresponding level of KCC2 activity or expression determined in a control subject experiencing less pain (as above) or substantially no pain. In an embodiment, the KCC2 activity may be determined as described above.

For example, intracellular chloride levels may be determined by administering, to a subject, an indicator compound (such as a compound indicative of chloride level) that is capable of contacting a CNS neural cell of that subject. Following the administration of the indicator compound, assessment of the in vivo signal associated with such indicator compound may be performed. In an embodiment, an indicator compound, such as a radionuclide (e.g. Thallium-201 ($^{201}$Tl), $^{99}$Tcm-tetrofosmin, $^{99}$Tcm-MIBI or $^{99m}$Tc-HMPAO or chloride conjugates thereof) or a compound indicative of KCC2 expression (such as an immunodetection-based reagent (e.g. antibody, single chain antibody or Fab fragment directed against the KCC2 polypeptide)) may be employed. In yet another embodiment, the indicator compound, upon intravenous injection, may cross the blood-brain-barrier and accumulate in neurons of the CNS analogously to potassium, i.e. to reflect potassium levels. In another embodiment, the dose of such radionuclide (e.g. $^{201}$Tl) may be about 100 MBq (3mCi). In yet another embodiment, the radionuclide (e.g. $^{201}$Tl) may be injected 15-20 minutes prior to SPECT imaging. Following injection of the indicator compound, an imaging technique may be performed to assess the in vivo signal associated with the indicator compound. Such imaging techniques include, but are not limited to, single photon emission computed tomography (SPECT), positron emission tomography and/or magnetic resonance imaging. The imaging technique may enable the assessment of the in vivo signal of the indicator Compound, such as the neural potassium gradient. Images can be obtained, for example, using gamma camera equipped with a high-resolution (5-7 mm) collimator and interfaced with a dedicated computer system. In an embodiment, serial projection images can be acquired over a 180° arc. In yet another embodiment, the radionuclide (e.g. $^{201}$Tl) retention by neurons can be expressed as a retention index (RI). The "retention index" as described herein is defined as:

$$\frac{\text{Delayed retention} - \text{early retention}}{\text{Early retention}} \times 100$$

In an embodiment, the "retention" of the retention index is herein defined as the amount of indicator compound (e.g. tracer or radionuclide) retained by a specific tissue at a certain time. In a further embodiment, the early retention is assessed before the delayed retention. In a further embodiment, the retention index is measured in a CNS tissue.

In an embodiment, the methods of diagnosis/prognostication noted above may be performed in conjunction with the therapeutic/prophylactic methods noted above, for preventing or treating pain associated with CNS dysfunction in a subject. Such a method thus comprises the diagnosis or prognostication of pain associated with CNS dysfunction and, in accordance with the diagnosis/prognosis, decreasing intracellular chloride levels in a CNS cell of the subject thereby to prevent or treat pain.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

Throughout this application, various references are referred to describe more fully the state of the art to which this invention pertains. The disclosures of these references are hereby incorporated by reference into the present disclosure.

EXAMPLES

Example 1

Methods

Nerve Injury. Briefly, peripheral nerve injury was induced by surgically implanting a polyethylene cuff (~2 mm long, 0.7 mm inner diameter) around the sciatic nerve of adult, male, Spague-Dawley rats as previously described (16). A group of rats also received sham surgery. Only animals that showed a gradual decrease in mechanical threshold (over 14-17 days) down to 2.0 g or less were used for further experiments.
Behavioural Testing. Thermal and mechanical threshold for nociceptive withdrawal reflexes were tested as previously described (17).
Slice preparation. Parasagittal slices (300-350 µm) of spinal cord were prepared from adult (>50 days old) male rats as previously described (9). Slices were continually superfused (2-3 ml·min$^{-1}$) with artificial cerebrospinal fluid (ACSF) containing (in mM): 126 NaCl, 2.6 NaHCO$_3$, 10 glucose, 2.5 KCl, 2 CaCl$_2$, 2 MgCl$_2$, 1.25 NaH$_2$PO$_4$, 0.001 TTX (bubbled with 95% O$_2$-5% CO$_2$, pH~7.4); when evaluating GABA$_A$/GlyR-mediated currents, 10 µM 6-cyano-7-nitroquinoxaline-2,3-dione (CNQX) and 40 µM D2-amino-5-phosphonovaleric acid (APV) were added to block fast glutamatergic transmission.
Recordings. For perforated patch recordings, the pipette tip was filled with a solution containing (in mM): 130 cesium gluconate (CsGluc), 5 CsCl, 2 MgCl$_2$, 11 BAPTA Calcium chelator (buffer), 1 CaCl$_2$, 4 ATP, 0.4 GTP, 10 HEPES (pH~7.4). The pipette was back-filled with this same solution supplemented with 25 µg/ml gramicidin D (gramicidin stock was at 10 mg/ml in DMSO). Recordings in this mode were selected when access resistance was stable between 25-0.45 MΩ. For whole-cell voltage-clamp recordings, pipettes were filled with the above solution without gramicidin D. Similarly, whole-cell current-clamp recordings were performed using pipettes filled with the same intracellular, solution as with voltage-clamp, except potassium methyl sulfate (KMeSO$_4$) was used to replace CsGluc. To clamp E$_{anion}$ at 0 mV, CsGluc was replaced with 110 mM CsCl in the intracellular solution. All whole-cell recordings at E$_{anion}$=0 mV were made at Vm=−60 mV in the presence of GluR-blockers. GABA was applied locally for 30-250 ms by pressure ejection through a patch micropipette. Data acquisition and analysis of PSCs was performed as previously described (9). All measurements are given as means±SEM, except where indicated. Statistical significance was tested using Student's t-tests for comparison of mean values, chi-square tests for contingency tables, and mixed design ANOVAs (post-hoc-Tukey's HSD) for repeated measures.
Calcium Imaging. Slices were prepared from PNI and naïve rats as detailed above for electrophysiological analysis. After 15 min incubation in ACSF, slices were loaded with 10 µM Fura-2-AM (a fluorometric calcium indicator, AM=acetoxymethyl) in HEPES-buffered saline (+10% DMSO) for 1 hour. Slices were washed for ~15 min with ACSF before being mounted in the recording chamber, where they continued to be superfused by ACSF (2-3 ml·min$^{-1}$). [Ca$^{2+}$]$_i$ was fluorometrically measured using a Zeiss Axioscope equipped with epifluorescence optics. Images were acquired using a TILL Photonics monochromator coupled to a CCD camera and regions of interest (for ratioing) were drawn on clearly distinct neuronal cell bodies.
Immunoblotting. Horizontal slices (150 µm) of the SDH were made from the lumbar enlargement of both PNI and naïve adult rats. Tissue extracts were prepared by homogenizing the slices with a Teflon pestle in a buffer containing 0.32 M sucrose, 0.5 mM Tris-HCl, pH 7.5, 2 mM ethylenediaminetetracetic acid (EDTA), 2.5 mM β-mercaptoethanol, and a cocktail of protease inhibitors (Complete™, Roche Diagnostics). Supernatants from 3,000 g (20 min) and 10,000 g (30 min) centrifugations were collected. Equal amounts of proteins (20 µg/lane) diluted in sample buffer were preheated at 37° C. for 30 min, resolved by SDS-PAGE, and electroblotted onto nitrocellulose membranes. Membranes were blocked 30 min in 5% nonfat dry milk in TBST buffer (150 mM NaCl, 10 mM Tris-HCl, pH 7.4, 0.05% Tween-20) and incubated overnight at 4° C. with a rabbit anti-KCC2 antibody (1:1000, Upstate Biotechnology). After several washes in TBST, membranes were incubated for 30 min at room temperature with peroxidase-labeled goat anti-rabbit antibody (1:2000). Chemiluminescent bands were detected using Super Signal Femto™ (Pierce Biotechnology). Digital images were captured with the VersaDoc™ imaging system (BioRad) and data were analysed with Quantity One™ software (BioRad).
Oligodeoxynucleotides. KCC2 antisense and scrambled oligodeoxynucleotides, phosphorothioated at all positions were designed as previously described (18): antisense, 5'-TCTC-CTTGGGATTGCCGTCA-3' (SEQ ID NO: 7; +59 relative to the ATG starting signal); scrambled, 5'-TCTTCTTGAGACT-GCAGTCA-3' (SEQ ID NO: 8).
Intrathecal Injections. At least three days prior to drug administration, rats were anaesthetized with sodium pentobarbital (65 mg kg$^{-1}$) and a lumbar spinal catheter was inserted into the intrathecal space, as previously described (11). Briefly, a small opening was created at the cisterna magna, and a catheter was inserted into the subarachnoid space and caudally directed ~8 cm to the lumbar enlargement of the spinal cord. Upon recovery from surgery, lower body paralysis was induced via i.t. (intrathecal) lidocaine (2%, 30 µl) injection to confirm proper catheter localization. Only animals exhibiting appropriate, transient paralysis to lidocaine, as well a lack of motor deficits were used for behavioural testing. Following drug/vehicle administration, animals were sacrificed and their vertebral column dissected to visually confirm correct placement of the catheter. Drugs included DIOA (10-30 µg, in OA % NaCl, 10% DMSO) and oligodeoxynucleotides (single doses of 2 mg at 0 h, 12 h & 24 h; 0.9% NaCl). Behavioural testing was performed as above; normal (~15 g) mechanical threshold for withdrawal responses was confirmed in naïve rats prior to receiving drug or vehicle. At the doses used, none of the compounds produced motor disturbances or sedation as assessed by grasping, righting and placing reflexes and behavioral observations (17).

Computer simulations. (see FIG. 5) All simulations were performed with NEURON 4.3.1 using a compartment model of a generic spinal lamina I fusiform neuron with morphology and passive membrane properties based on (19). Dendrites bifurcated up to fourth order and an axon similar to that described in (19) were attached to the soma. Fast $Na^+$ and delayed rectifier $K^+$ currents based on (30) were inserted at 0.1 and 0.01 $S/cm^2$, respectively, in the soma and axon initial segment and nodes; voltage threshold for spiking was −49 mV. Two sets of inhibitory synapses were distributed randomly in the perisomatic region and four sets of excitatory synapses were more distal; each set was driven by an independent Poisson process at rates extrapolated from (31) and (32).

Electron microscopy. (see FIG. 6) Tissue was prepared for ultrastructural analysis as previously described (35). Briefly, rats were perfused through the aortic arch with 0.9% NaCl followed by a fixative solution containing 4% paraformaldehyde (Sigma-Aldrich, Germany). After perfusion, spinal cords were removed, coronal blocks were dissected, then 60 μm thin sections were cut cryoprotected and freeze-thawed over liquid nitrogen and rinsed several times in phosphate buffer before incubation in the primary antiserum. After incubation in blocking solution containing 2% bovine serum albumin (BSA), sections were incubated in rabbit anti-KCC2 (1:500, Upstate Biotechnology, USA) for 48 hours at 4° C. After extensive washing, sections were incubated with 1 nm gold-conjugated anti-rabbit secondary antibody (1:250, Aurion) for 12 hours at 4° C. followed by silver intensification (SE-EM, Aurion). Sections were treated with 0.5% $OsO_4$ (20 min), dehydrated in graded ethanol, then in propylene oxide and embedded in Durcupan ACM (Fluka). After ultra-sectioning (Ultracut™ UCT, Leica, Germany), specimens were examined using an electron microscope (Philips Tecnai 12, equipped with MegaView™ CCD camera). Non-consecutive (spacing>3 μm) ultrathin sections were analyzed in the electron microscope. Boutons with synaptic profiles were randomly selected and analyzed in laminae I & II and white matter for the expression of the KCC2 protein (36).

Intrathecal administration of K-252a. (see FIG. 8) K-252a was prepared in 25 ul of 0.9% NaCl solution containing 10% DMSO. Intrathecal catheterization was performed by creating a small opening at the cisterna magna, and inserting P10 polyethylene tubing into the subarachnoid space—caudally directed ~8 cm to the lumbar enlargement of the spinal cord.

Example 2

Results

Figure 1B:
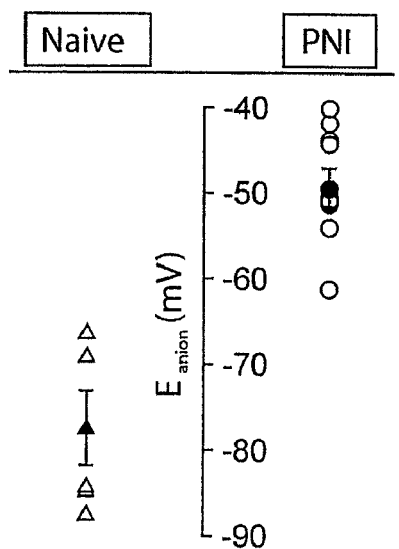
Figure 1C:
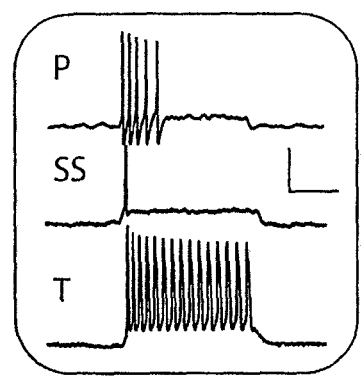
Figure 1D:
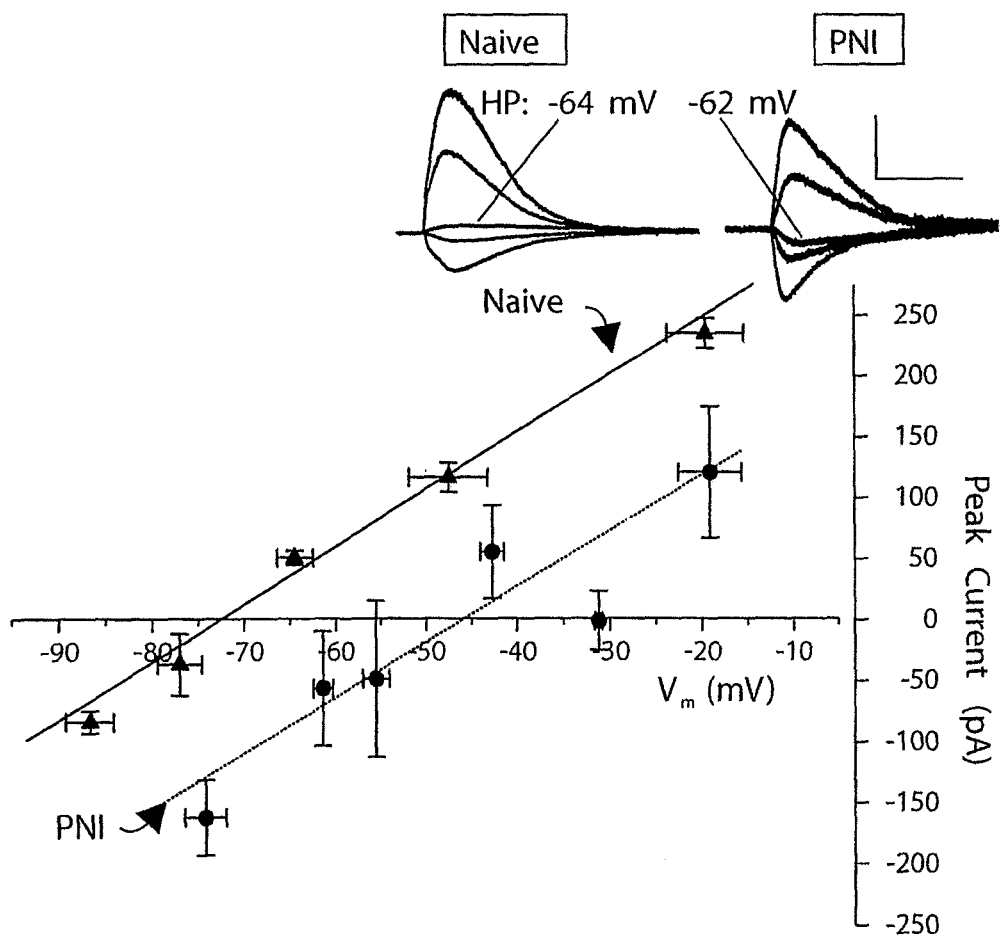
Figure 2A:
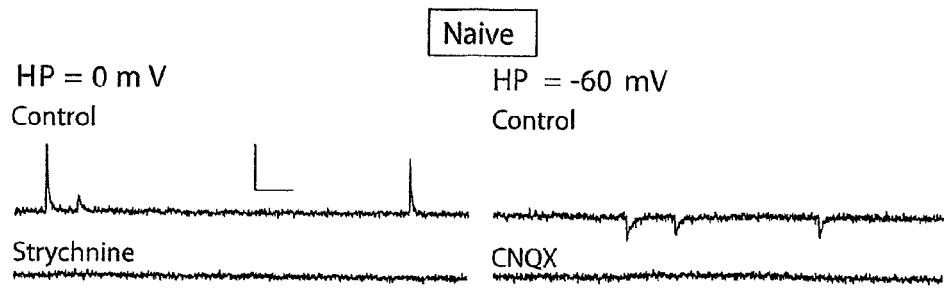
FIG. 2: Switch from GlyR(receptor)-only to mixed GABA$_A$R- and GlyR-mediated miniature postsynaptic currents (mPSCs) following PNI in LI neurons. a) Raw traces of outward (left) and inward (right) miniature synaptic events from a naïve rat LI neuron. All outward mPSCs were abolished by strychnine, while all inward mPSCs (recorded in the presence of strychnine and bicuculline) were abolished by the GluR antagonist CNQX. HP—Holding Potential. Scale bar is 20 pA (y), 300 ms (x). b) Raw traces of inward (left) and outward (right) miniature synaptic events recorded from a PNI rat LI neuron. Unlike in naïve rats, both strychnine and bicuculline were required to abolish all outward mPSCs. Inward mPSCs remained completely sensitive to CNQX. Scale bar is 20 pA (y), 300 ms (x). c) left—Superimposed individual mPSCs recorded from PNI rat LI neurons. GlyR-only and GABA$_A$R-only and mixed GABA$_A$R/Glyr-mediated were clearly identifiable by their sensitivity to strychnine and/or bicuculline. Right—Averages of >100 GlyR- and GABA$_A$R-mediated mPSCs recorded from a PNI rat LI neuron. Scale bar is 15 pA (y), 20 ms (x). d) Mean peak conductance of mPSCs recorded from naïve (N; n=10 for GlyR; n=5 for GluR) and PNI (P; n=9 for GlyR; n=8 for GluR) LI neurons. P(B) indicates GlyR-mediated mPSCs recorded in PNI rat LI neurons (n=12) at 0 mV in the presence of bicuculline. e) Net charge carried by GlyR-mediated mPSCs in naïve rats (n=6), by bicuculline-isolated GlyR-mediated mPSCs in PNI rats [PNI(Bic); n=4], and by mixed GABA$_A$R/GlyR-mediated mPSCs in PNI rat LI neurons (PNI; n=12). f) Cumulative probability plot illustrating the difference between the GlyR-only mPSC inter-event interval (I.E.I.) in naïve LI neurons and that of bicuculline-isolated GlyR-only mPSCs in PNI rat LI neurons [PNI(Bic)], both recorded at $E_{anion}$=0 mV. The addition of the GABA$_A$R-mediated mPSCs (PNI) compensated the GlyR-only mPSC frequency decrease. Inset—No effect of PNI on the frequency of GluR-mediated mPSCs.
Figure 2B:
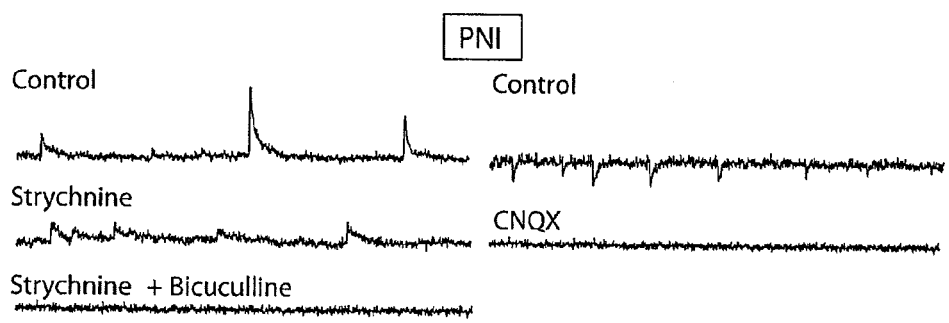
Figure 2C:
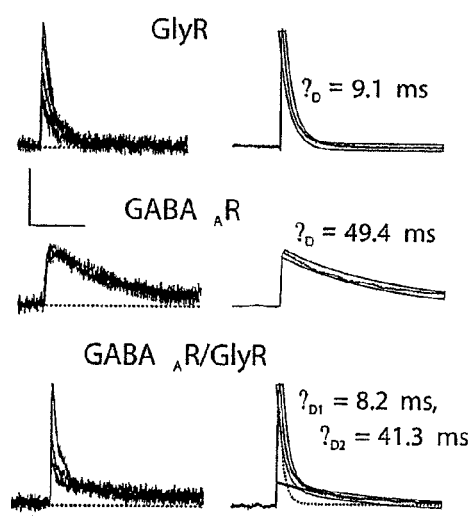

Peripheral neuropathy was induced in rats by chronically constricting the sciatic nerve (FIG. 1a). To test whether the hyperexcitability (sensitization) of SDH neurons that follows peripheral nerve injury (PNI) is associated with modification of the anion gradient ($V_{anion}$) anion reversal potential ($E_{anion}$) was measured using gramicidin-perforated patch clamp recording. This technique avoids disrupting the intracellular anion concentration (8). Responses to exogenous GABA application showed that the anion reversal potential ($E_{anion}$) of lamina I (LI) neurons taken from PNI rats was −49.0±2.3 mV (range: −40 to −62.2 mV, n=9) compared to −72.6±3.5 mV (range: −63.0 to −79.9 mV, n=5; p<0.005) in LI neurons from naïve rats (FIG. 1b-d). Resting membrane potential was not significantly different between PNI (−62±4 mV, n=7) and naïve rat LI neurons (−61±2 mV, n=16; p>0.1). Spontaneous and evoked postsynaptic currents (PSCs), recorded from PNI rat LI neurons in the presence of fast glutamate receptor (GluR) blockers were also inward (depolarizing from rest), their mean reversal potential increasing by 16.1 mV relative to that in lamina I neurons from naïve rats (n=6, PNI; n=4, naïve). It was then investigated whether other properties of synaptic transmission were altered in the SDH after PNI. Inhibitory miniature PSCs (mPSCs) in LI neurons from naïve rats are mediated by glycine receptors (GlyRs) alone despite GABA and glycine corelease from local inhibitory interneurons (9; FIG. 2a). While GluR-mediated mPSCs were unaffected by PNI (FIG. 2b), in all cells tested from PNI rats, a population of outward mPSCs at 0 mV persisted in the presence of the GlyR antagonist strychnine (up to 1 μm; n=4). These remaining mPSCs were mediated by $GABA_AR_S$, as they were blocked by bicuculline (10 μM) and displayed prolonged decay kinetics compared to the GlyR-mediated component ($\tau_{D(GABA_AR)}$=34.0±2.9 ms, n=5, vs. $\tau_{D(GlyR)}$=11.3±1.3 ms, n=6; p<0.01; FIG. 2C).

Kinetic analysis further revealed that the decay phase of 36.9±2.3% of mPSCs followed a dual exponential function ($\tau_{D1}$=7.5±2.0 ms and $\tau_{D2}$=51.3±7.9 ms; n=6; FIG. 2c). These events possessed both a $GABA_AR$ and a GlyR-mediated component, as either strychnine or bicuculline could lead to the abolition of their respective components (n=4). Therefore, in parallel with the collapsed $V_{anion}$, PNI caused reorganization at LI synapses thereby unmasking $GABA_AR$-only and mixed $GABA_AR$/GlyR-mediated mPSCs, in addition to those mediated by GlyRs alone. This synaptic organization is similar to that observed in immature LI-II neurons (9). The net effect of this synaptic switch is that it yielded a population of quantal synaptic events with significantly longer decay kinetics.

Figure 2D:
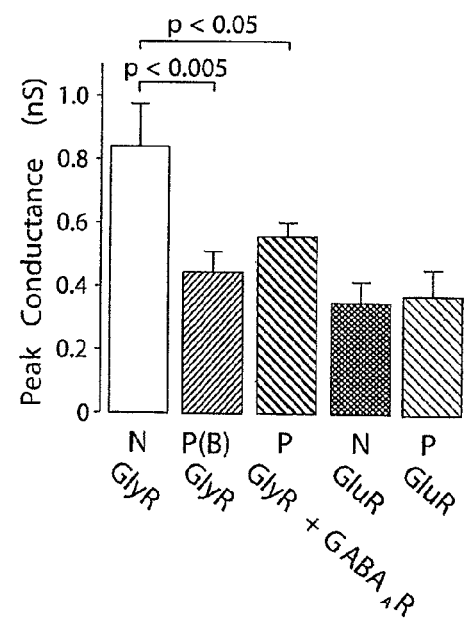

To examine the function of the PNI-induced $GABA_AR$-mediated contribution to mPSCs, we analysed both the peak conductance and the frequency of mPSCs. This was performed using CsCl-filled pipettes to clamp the $E_{anion}$ at 0 mV in both LI neurons taken from PNI and naïve rats to prevent biased detection of mPSCs resulting from changes in driving force. Peak conductance of GlyR-only mPSCs recorded in LI neurons taken from PNI rats was significantly smaller (~2-fold) than that recorded from naïve rat LI neurons (FIG. 2d). The addition of $GABA_AR$-mediated events in the PNI condition, however, partially compensated the decrease in GlyR-only conductance. The peak conductance of GluR-mediated quantal events was not significantly different between LI neurons taken from naïve and PHI rats (FIG. 2d).

Figure 2E:
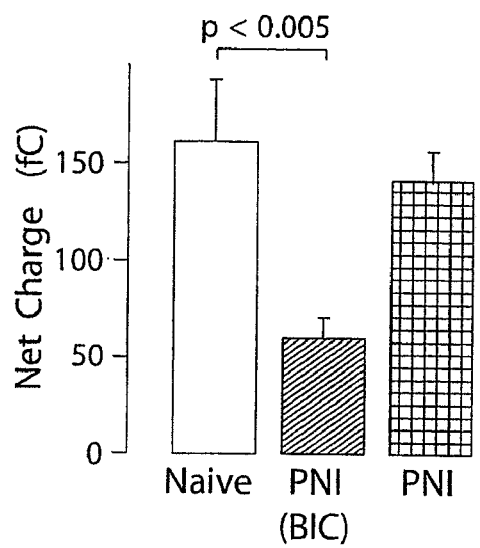

Factoring together the changes in peak conductance, kinetics, and driving force, the net charge carried by GlyR-only mPSCs at resting membrane potential in LI neurons taken from PNI rats was nearly 3-fold smaller than that in naïve rats (FIG. 2e). With the contribution of $GABA_ARs$, however, the net charge carried by mPSCs in PNI rats rose back to that mediated by GlyRs in naïve rats. This result suggests that, although equivalent in magnitude, hyperpolarizing charge in naïve LI neurons was carried by GlyR-mediated mPSCs alone, whereas depolarizing charge was transferred predominantly via $GABA_ARs$ in PNI rat LI neurons, due to the prolonged decay kinetics of $GABA_AR$-mediated mPSCs.

Figure 2F:
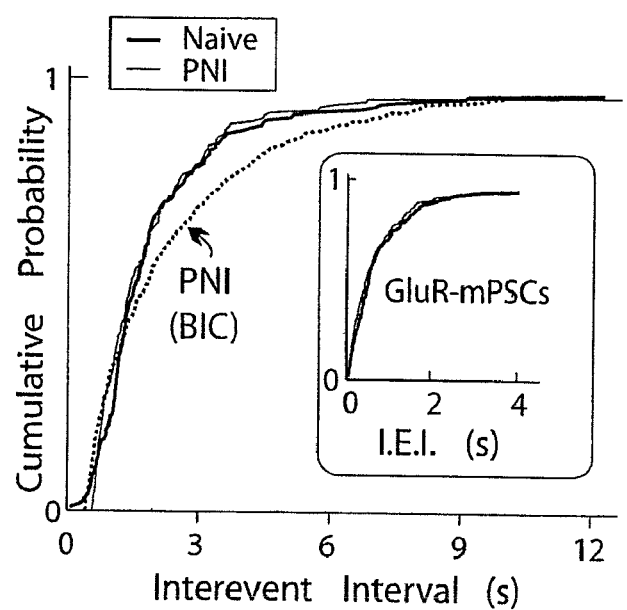

The frequency of GlyR-only mPSCs recorded in LI neurons from PNI rats was observed to be significantly less (0.13±0.04 Hz, n=5) than that for GlyR-only mPSCs in naïve rat LI neurons (0.18±0.04 Hz, n=6; p<0.05; FIG. 2f). As with peak conductance, however, the addition of the $GABA_AR$-mediated mPSCs compensated the PNI-induced decrease in frequency (0.22±0.10 Hz, n=4, for all $GABA_AR$ and/or GlyR-mediated events combined; p>0.5): In contrast, there was no significant change in the frequency of GluR-mediated events in LI neurons isolated from PNI rats (1.51±0.90 Hz, n=9) compared to LI neurons from naïve rats (0.82±0.40 Hz, n=S; p>0.3; FIG. 2f).

Figure 3A:
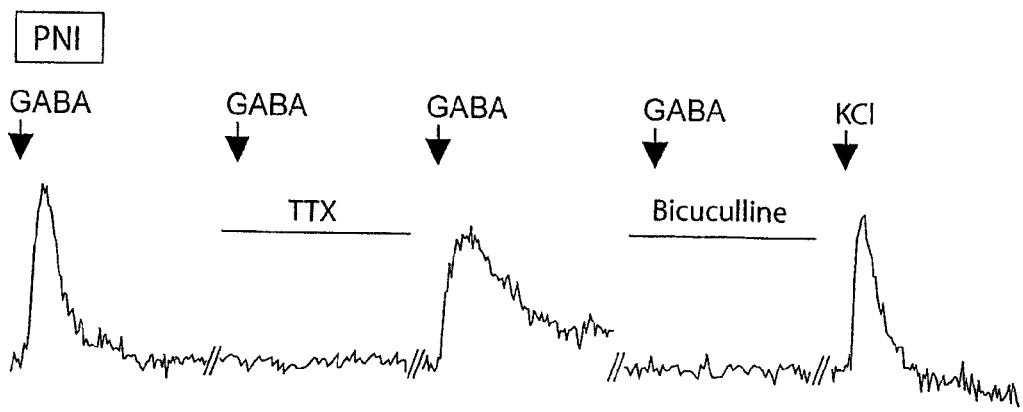
FIG. 3: PNI-induced downregulation of KCC2 in SDH lamina I neurons ipsilateral to PNI led to GlyR/GABA$_A$R-mediated excitation. a) Brief GABA application (30 ms pressure puff) caused a tetrodotoxin (TTX) and bicuculline-sensitive rise in $[Ca^{2+}]_i$ in a LI neuron from a fura-2-am ($Ca^{2+}$ indicator) loaded slices of a PNI rat. b) KCl application, but not GABA application (up to 250 ms-long pressure puffs) caused no change in $[Ca^{2+}]_i$ in a naïve rat LI neuron. In the presence of the KCC2-specific antagonist DIOA, GABA application did elicit a rise in $[Ca^{2+}]_i$ naïve, rat LI neuron. Scale bar is 0.02 (y), 10 s (x). c) Percentage of LI neurons displaying a GABA-evoked increase in $[Ca^{2+}]_i$. The proportion was significantly higher in PNI rats ($\chi^2_{corrected}$=3.91) and in the presence of DIOA in naïve rats ($\chi^2_{corrected}$=4.43). d) Representative trace confirming that exogenous GABA could repeatedly elicit action potentials in a lamina I neuron. Upper scale bar is 5 mV (y), 200 ms (x). Lower scale bar is 30 mV (y), 4 s (x). Inset—response to a depolarizing pulse confirming this was a single-spike neuron (19). Scale bar is 20 mV (y), 300 ms (x). e) Similarly, focal stimuli (in the presence of glutamate receptor blockers) elicited bicuculline-sensitive monosynaptic depolarizing postsynaptic potentials that could evoke action potentials in a lamina I neuron from PNI rats. Scale bar is 5 mV (y), 250 ms (x). Inset—response to a depolarizing pulse confirming this was a phasic neuron (19). Scale bar is 20 mV (y), 300 ms (x). f) Left—Immunoblotting revealed that KCC2 levels were decreased in the lumbar SDH lying ipsilateral (Ipsi), but not contralateral (Con), to the site of the PNI. Right—Average intensities (±SEM) of KCC2 protein (normalized to actin) measured from immunoblots (n=4) as in left (Ipsi normalized to Con).
Figure 3B:
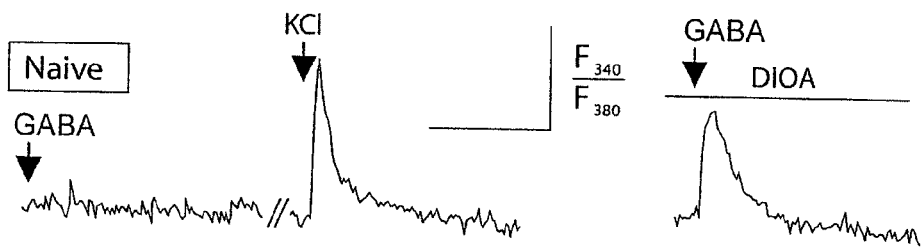
Figure 3C:
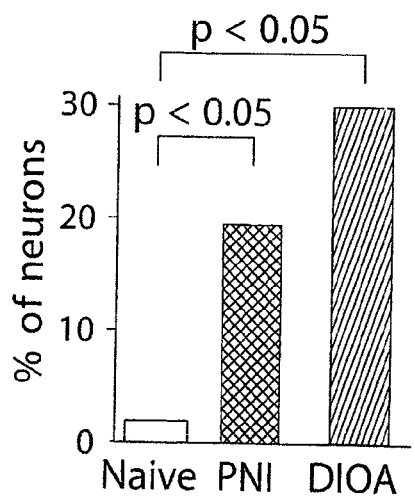
Figure 3D:
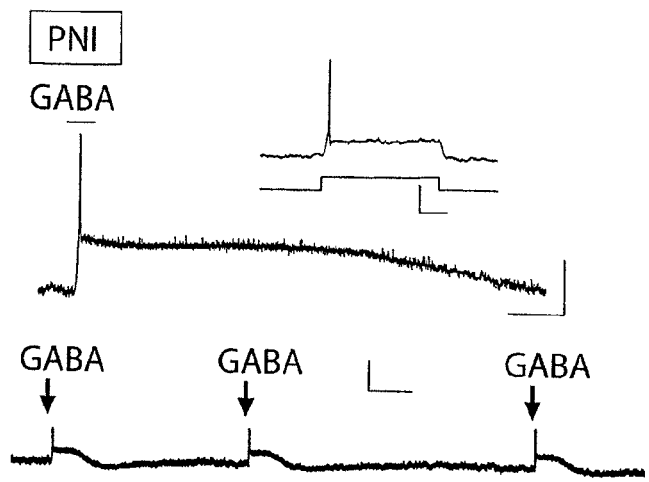
Figure 3E:
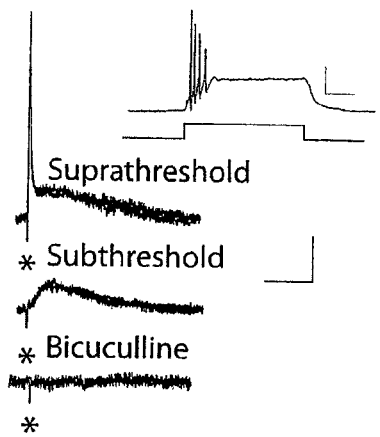
Figure 3F:
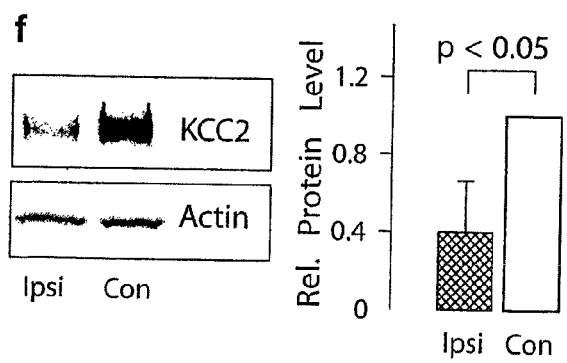

If depolarizing $GABA_AR$/GlyR-mediated postsynaptic currents exert a net excitatory influence in PNI LI neurons, they should directly evoke action potentials, and consequently lead to $Ca^{2+}$ influx. To test this hypothesis, we employed $Ca^{2+}$-imaging using fura-2-am loaded LI neurons in slice to obtain a large data set. Administration of exogenous GABA to neuronal somata caused a significant increase in the concentration of intracellular $Ca^{2+}$ ($[Ca^{2+}]_i$) in 19% of LI neurons (n=53; FIGS. 3a,c) lying ipsilateral to the site of PNI. This represents a seven-fold increase compared to LI neurons found in naïve and/or contralateral dorsal horn, where an increase in $[Ca^{2+}]_i$ to GABA application was observed in only 1 of 37 neurons tested (FIGS. 3b,c). These responses were blocked by bicuculline (10 µM; n=5) and by the voltage sensitive sodium channel blocker tetrodotoxin (TTX; 1 µM; n=31). We then further confirmed electrophysiologically that applied GABA and synaptically elicited anionic postsynaptic potentials can directly evoke action potentials (FIGS. 3d,e). These results indicate that postsynaptic anion fluxes can cause net excitation in lamina I neurons in PNI rats. We then compared KCC2 protein levels by immunoblotting on horizontal slices of SDH. The KCC2 expression level in the lumbar SDH ipsilateral to the PNI was significantly reduced (>2-fold) relative to the side contralateral to the injury (FIG. 3f). In naïve rats, there was no significant difference between the two sides (n=3).

If a decrease in the expression of the KCC2 exporter leads to an increase in neuronal $[Cl^-]_i$ and, in turn, $GABA_AR$-mediated depolarization, a pharmacological blockade of the KCC2 exporter in LI neurons from naïve rats should have the same effect. To test for this possibility, we bath applied the selective KCC2 blocker DIOA (30 µM) to naïve spinal slices. As in the PNI condition, GABA application in the presence of DIOA caused an increase in $[Ca^{2+}]_i$ in 30% of naïve LI neurons tested (FIGS. 3b,c).

Figure 5A:
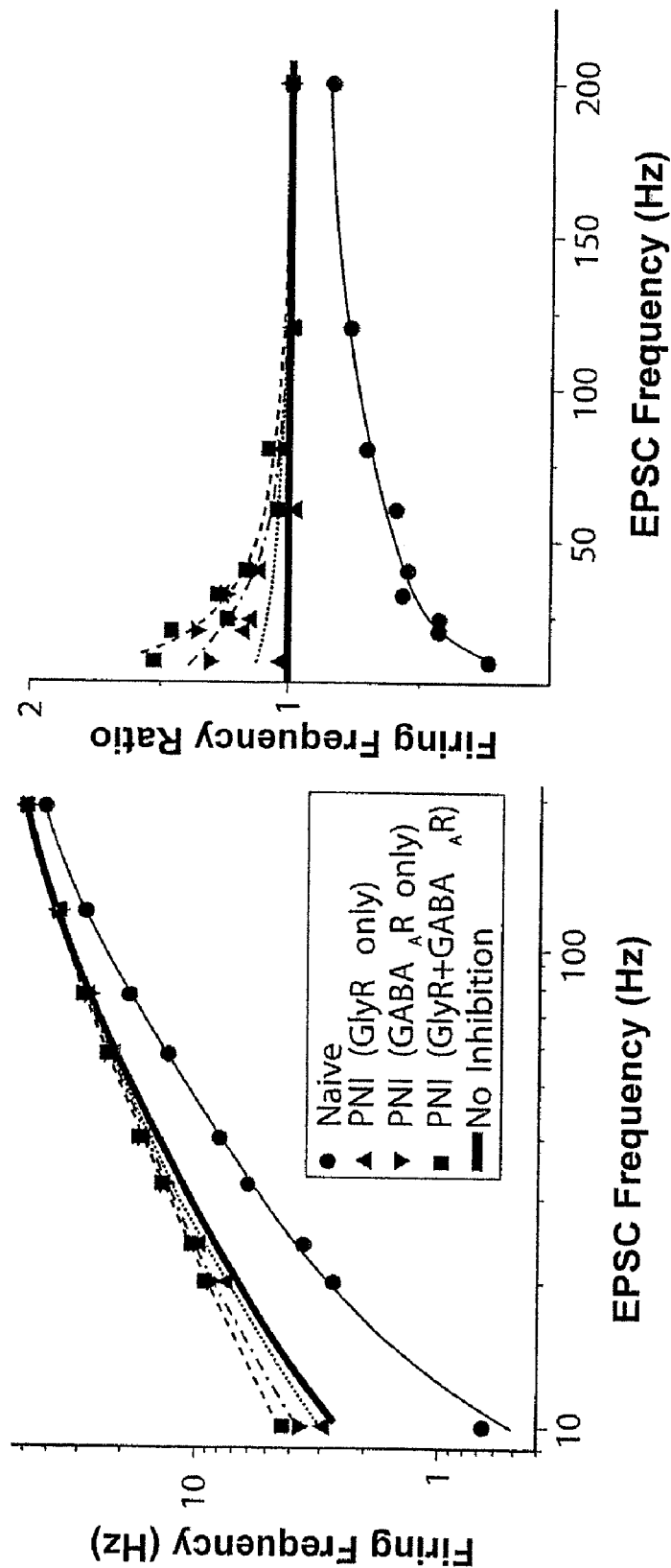
FIG. 5: Computer simulations of in vivo synaptic conditions confirmed that sensitization of Lamina I neurons occurred as a function of the shift in the $E_{anion}$. a) Left—Computer simulations using a model neuron (see Examples) demonstrate how PNI-induced changes to GlyR- and $GABA_AR$-mediated PSCs [PNI(GlyR+$GABA_AR$)] affect the output firing frequency of LI neurons as a function of GluR-mediated PSC frequency. Also shown is the result in LI neurons after PNI if only considering the effect of GlyR-mediated [PNI(GlyR-only)] or $GABA_AR$-mediated [PNI($GABA_AR$-only)] synaptic events. Right—Same data as shown in the left panel, but expressed in terms of firing frequency ratio, which was calculated as the quotient of a specific data set divided by the No Inhibition data set (i.e., a firing frequency ratio of one is equivalent to no inhibition). While the normally hyperpolarizing GlyR-mediated PSCs (mean $E_{anion}$=−72.8 mV in naïve rats) had a net inhibitory effect on the output firing frequency ($f_{out}$), depolarizing GlyR-mediated PSCs (mean $E_{anion}$=−49.0 mV in PNI rats), enhanced $f_{out}$ beyond that predicted to result with no inhibition, demonstrating a net excitatory effect. This excitatory effect was more prevalent when the $GABA_AR$ component was incorporated due to the increased charge carried by $GABA_AR$-mediated PSCs. b) Left—Effect of different values of $E_{anion}$ (over the range observed in our study) on the firing frequency of a LI neuron after PNI. Right—Same data as left panel expressed in terms of firing frequency ratio (as above).
Figure 5B:
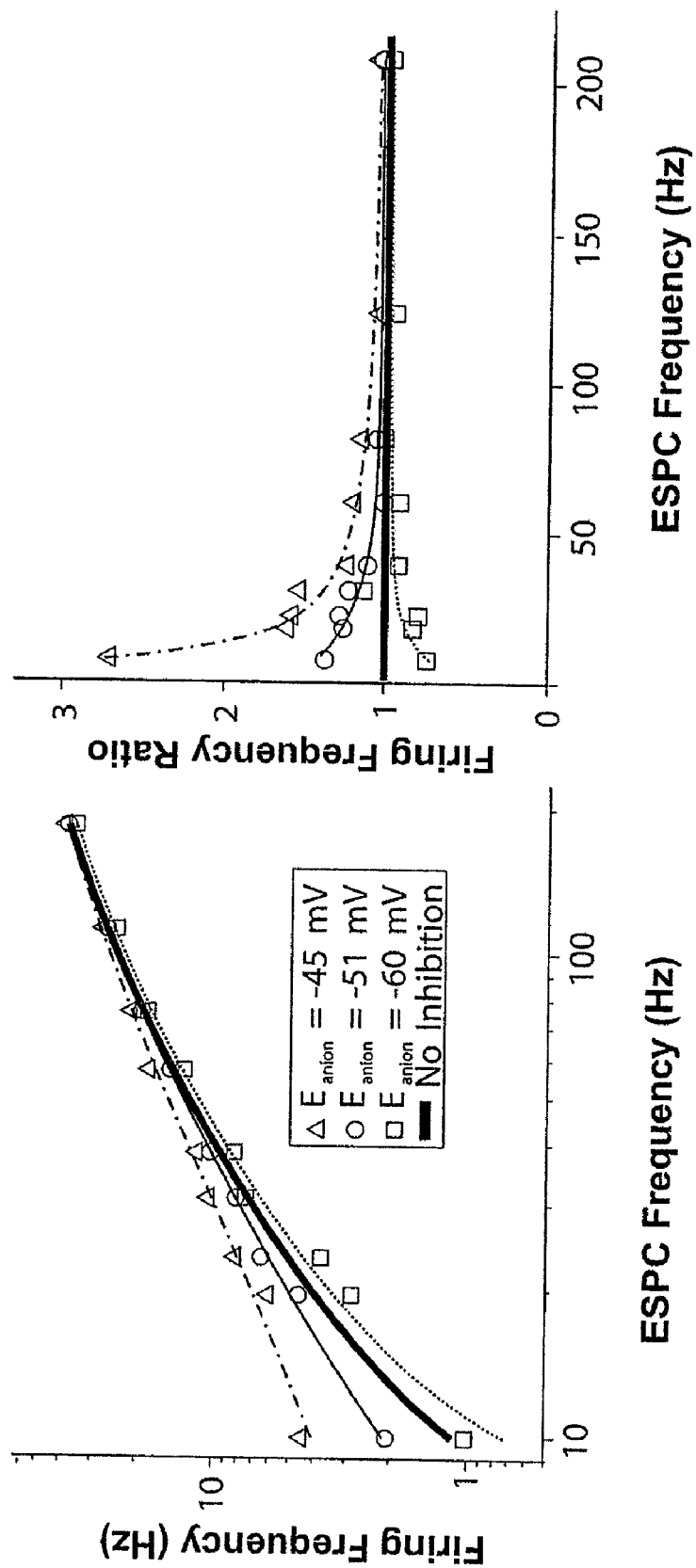

To assess whether the empirically determined-changes in $GABA_AR$/GlyR-mediated postsynaptic control were sufficient to account for the central sensitization which follows PNI, we simulated in vivo conditions using a biophysically-realistic neuron model (FIG. 5). The simulation confirmed that, after PNI, the extent of LI neuronal sensitization varied as a function of their $E_{anion}$, ranging from slight disinhibition to a net hyperexcitation.

Figure 4A:
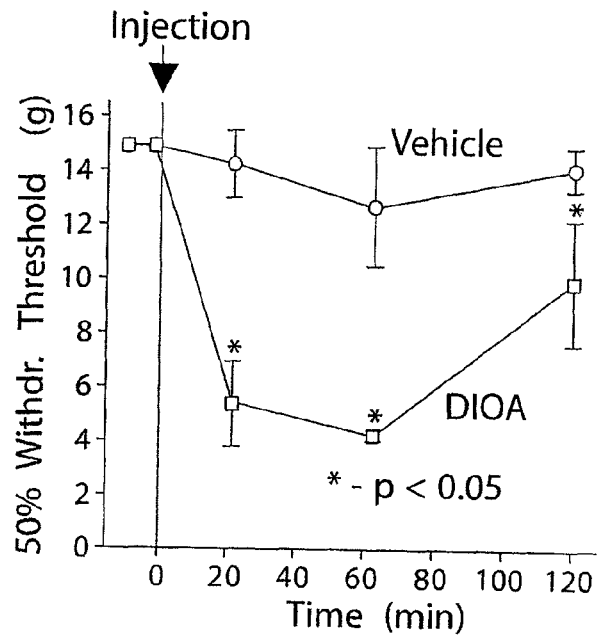
FIG. 4: Selective blockade or knock-down of the postsynaptic KCC2 exporter in the SDH significantly reduced nociceptive threshold. a) Tactile nociceptive withdrawal threshold as a function of time after intrathecal injections of DIOA (n=5) or vehicle (n=3). b) Thermal nociceptive withdrawal latency as a function of time after intrathecal injections of DIOA (n=3) or vehicle (n=3). Upon withdrawal, the rats also often licked their paw indicating nociception. c) Spontaneous mPSCs recorded with a CsCl (cesium chloride) pipette (to clamp $E_{anion}$ at 0 mV) in a LI neuron in the presence and absence of DIOA. Scale bar is 20 pA (y), 300 ms (x). d) Cumulative probability plot (n=4 neurons×50 mPSCs) demonstrating that DIOA neither affected the peak conductance of synaptic events (p>0.5), nor GABA-evoked responses (n=5; p>0.5, Inset) and therefore does not act on GlyRs nor GABA$_A$Rs. $G_{peak}$=peak conductance. e) Local lumbar spinal (intrathecal) administration of a KCC2 antisense oligodeoxynucleotide (each 12 h) caused a significant decrease in the tactile nociceptive withdrawal threshold in naïve rats (n=8), compared to those that received the scrambled oligodeoxynucleotide (n=7). Inset, Decrease in spinal KCC2 protein levels (measured by immunoblots) following antisense (AS, 12 h or 36 h) or scrambled (S, 36 h) oligodeoxynucleotide treatment. f) Lack of KCC2 immunoreactivity in dorsal root ganglia (DRG) in a naïve rat, compared to SDH. g) Electron micrograph illustrating the selective expression of KCC2 in SDH dendrites (D), but not synaptic boutons (B) (for quantitative details see FIG. 6). Arrows point to synapses. Scale bar is 0.2 μm.
Figure 4B:
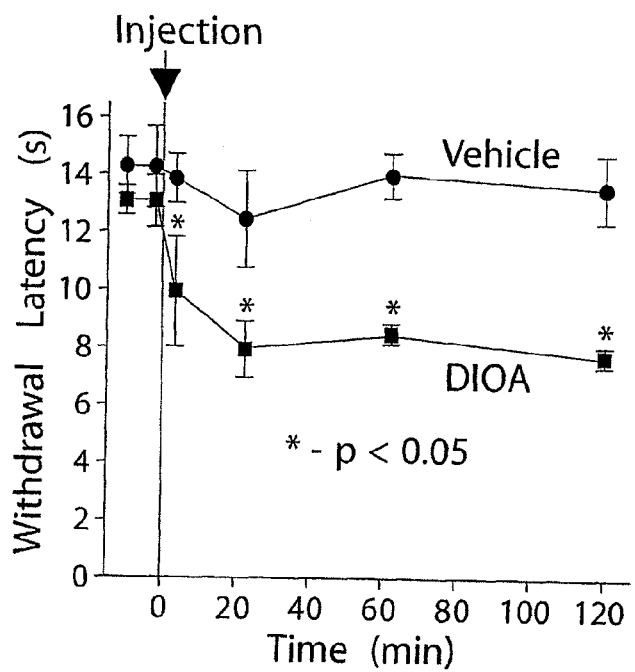
Figure 4C:
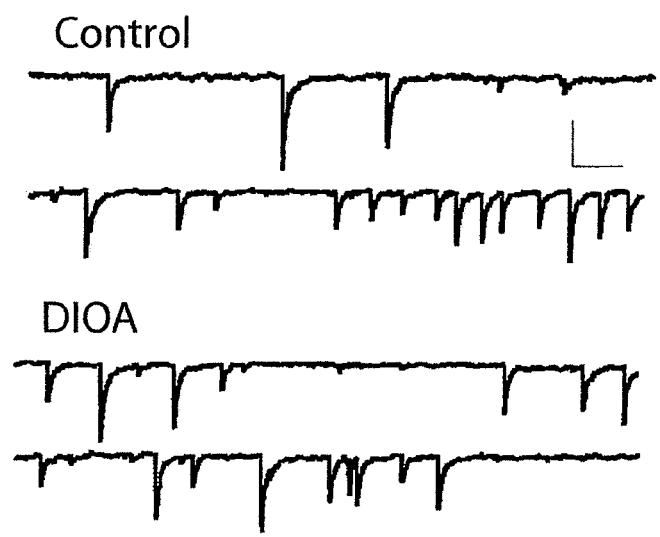
Figure 4D:
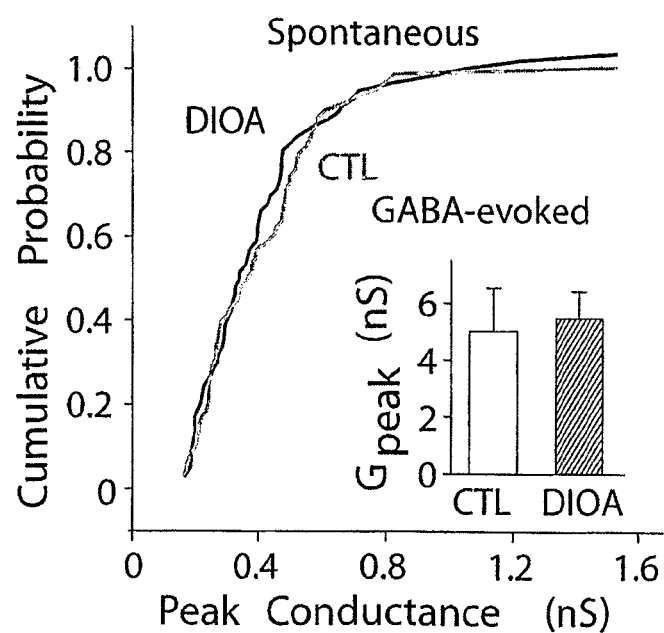
Figure 4E:
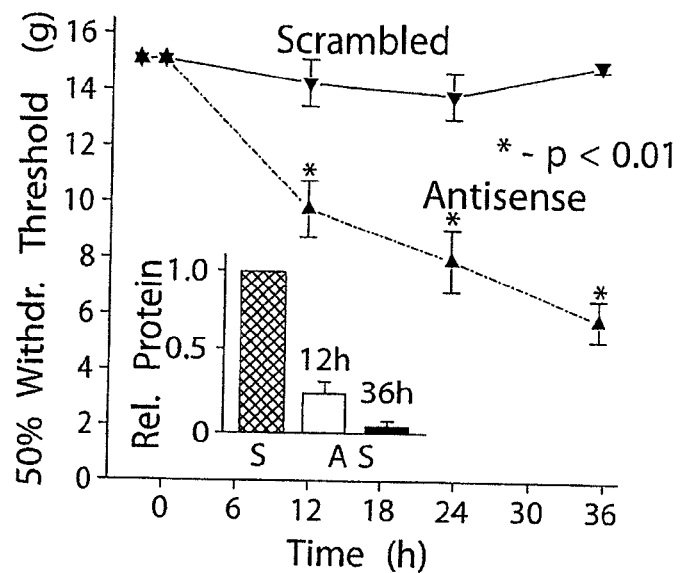

To test whether this hyperexcitability (sensitization) would result in a decrease in the stimulus threshold to evoke a nociceptive withdrawal reflex, we administered DIOA (15-30 µg) directly to the lumbar enlargement of the spinal cord in intact rats via an intrathecal catheter. DIOA caused a rapid and reversible decrease in nociceptive threshold to both mechanical and thermal stimuli (FIG. 4a-b). A similar decrease in nociceptive threshold was further obtained via selective knock-down of the exporter using spinal administration of an antisense oligodeoxynucleotide against KCC2 mRNA (FIG. 4e), further confirming the functional impact of KCC2 downregulation.

Figure 7:
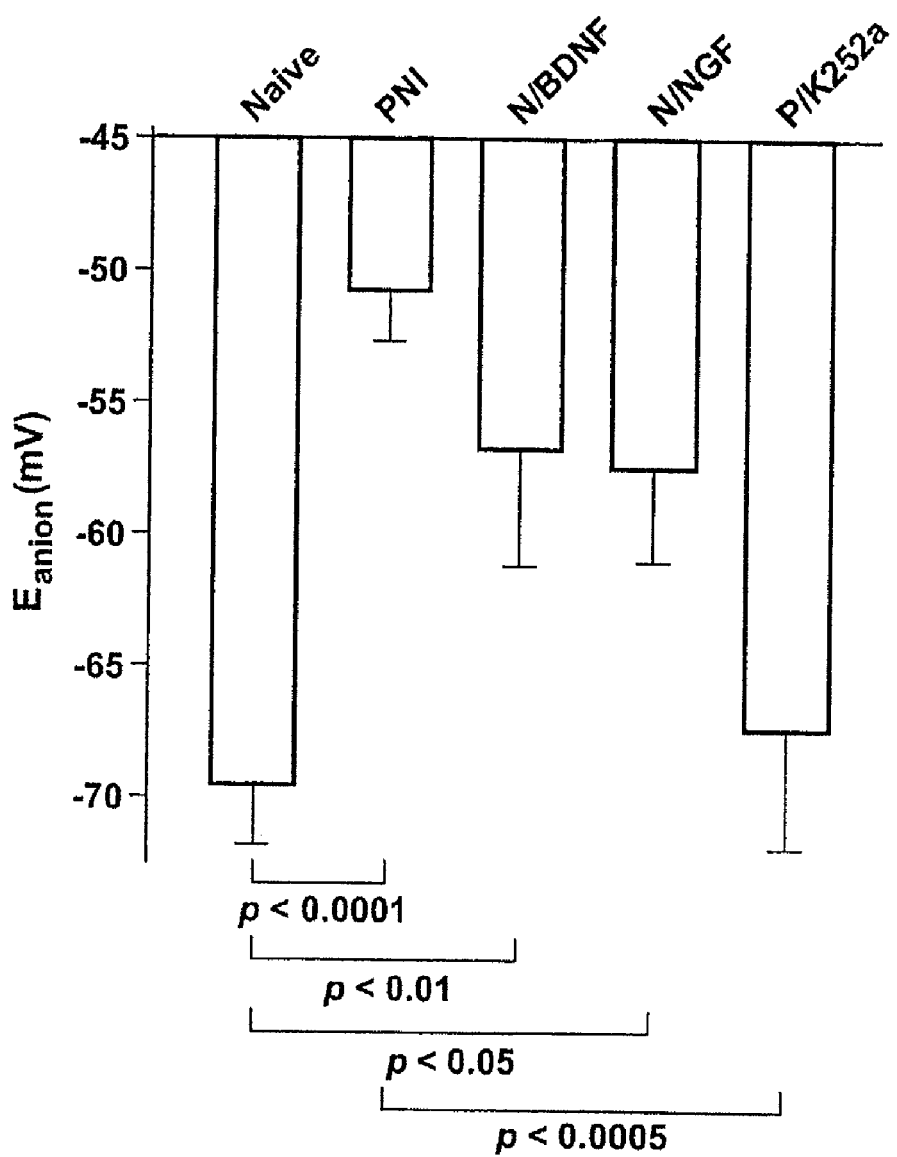
FIG. 7: Effect of various treatments on anion (bicarbonate and chloride) reversal potential ($E_{anion}$) recorded from lamina I neurons of naïve and PNI rats.
Figure 8:
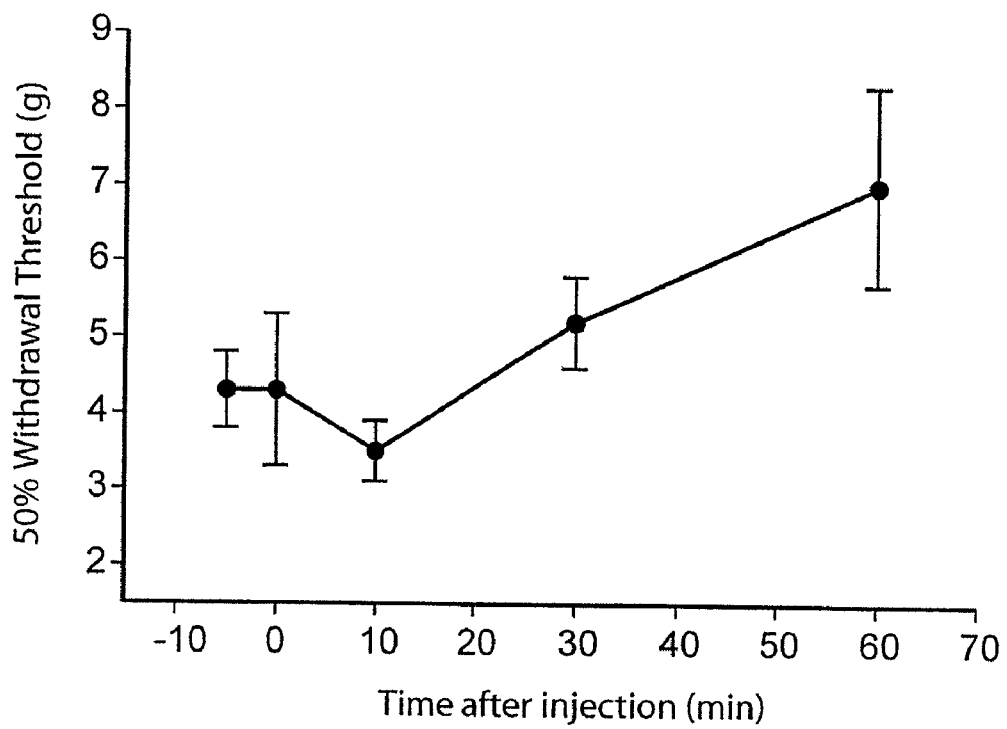
FIG. 8: Intrathecal administration of the receptor tyrosine kinase inhibitor K-252a (6 nM) resulted in an increase in the threshold for tactile nociceptive withdrawal.

As shown in FIG. 7, we demonstrate that in lamina I neurons taken from rats with peripheral neuropathy, the transmembrane anion reversal potential ($E_{anion}$) is significantly more depolarized than that in lamina I neurons from naïve rats. The anion (bicarbonate and chloride) reversal potential ($E_{anion}$) of recorded from lamina I neurons taken from naïve rats was significantly less than that recorded from the lamina I neurons of rats that had received a peripheral nerve injury (PNI). Bath application of both BDNF (50 ng/ml; N/BDNF) and NGF (50 ng/ml; N/NGF) caused the $E_{anion}$ recorded from naïve rat lamina I neurons to become significantly depolarized, indicating a collapse of the transmembrane anion gradient. Alternatively, bath application of the TrkB antagonist K-252a (200 nM; P/K252a) to lamina I neurons taken from a PNI rat caused a hyperpolarization of the $E_{anion}$ to a level similar to that observed in lamina I neurons taken from naïve rats. All $E_{anion}$ values were confirmed using gramicidin-D perforated-patch voltage-clamp recordings. This depolarized $E_{anion}$ is the result of a decreased expression of the KCC2 cotransporter in the lamina I neurons taken from neuropathic rats, as noted above. In lamina I neurons from naïve rats, it is further shown herein that the $E_{anion}$ may be depolarized significantly via the perfusion of the growth factors NGF and BDNF, suggesting that these growth factors may decrease the function and/or expression of the KCC2 protein in the superficial dorsal horn. Alternatively, blocking the BDNF receptor, TrkB, in lamina I neurons taken from neuropathic rats using the protein kinase inhibitor K-252a, is shown herein to reverse the depolarization of the $E_{anion}$, returning this value to a level similar to that observed in lamina I neurons taken from naïve rats. Further, as shown in FIG. 8, intrathecal administration of the receptor tyrosine kinase inhibitor K-252a (6 nN) (but not vehicle injection alone) resulted in an increase in the threshold for tactile nociceptive withdrawal in rats that had received peripheral nerve injury. K-252a can thus reverse the hyperalgesia/allodynia after its development following peripheral nerve injury. K-252a did not produce any motor disturbances or sedation as assessed by grasping, righting and placing reflexes and behavioral observations. It is envisioned that this inhibitor reactivates the KCC2 cotransporter in lamina I neurons taken from neuropathic rats by blocking phosphorylation, perhaps at a protein tyrosine kinase site on the transporter or on its transcription factors (or other regulatory substrate).

The results herein show that the painful neuropathy that follows PNI can be explained by a downregulation of the KCC2 exporter and the resultant shift in the $V_{anion}$ in spinal LI neurons. They also demonstrate that such a modification of $V_{anion}$ in adult animals can occur in a neuron transsynaptic to an injury site. Previous efforts to identify a substrate underlying the hyperexcitability characteristic of peripheral neuropathy have focussed on measuring changes in number of GABAergic interneurons, GABA content or $GABA_AR$ expression. The results have been contradictory (3-6). The findings presented herein provide a new avenue to understand such mechanisms of disinhibition. The conversion of the $GABA_AR$/GlyR-mediated postsynaptic action via a shift in $V_{anion}$ provides a mechanistic basis for central sensitization, including increases in neuronal responsiveness and number of excitatory inputs.

Figure 4F:
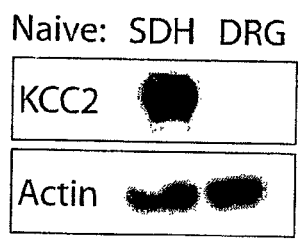
Figure 4G:
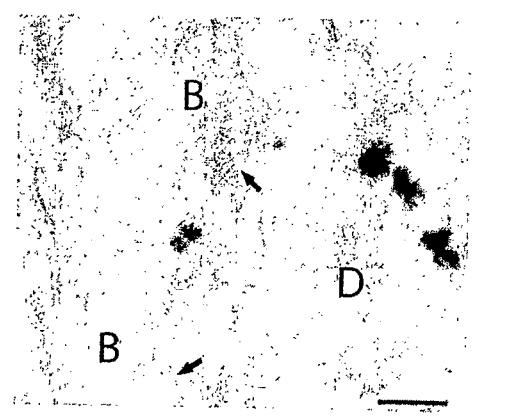
Figure 6A:
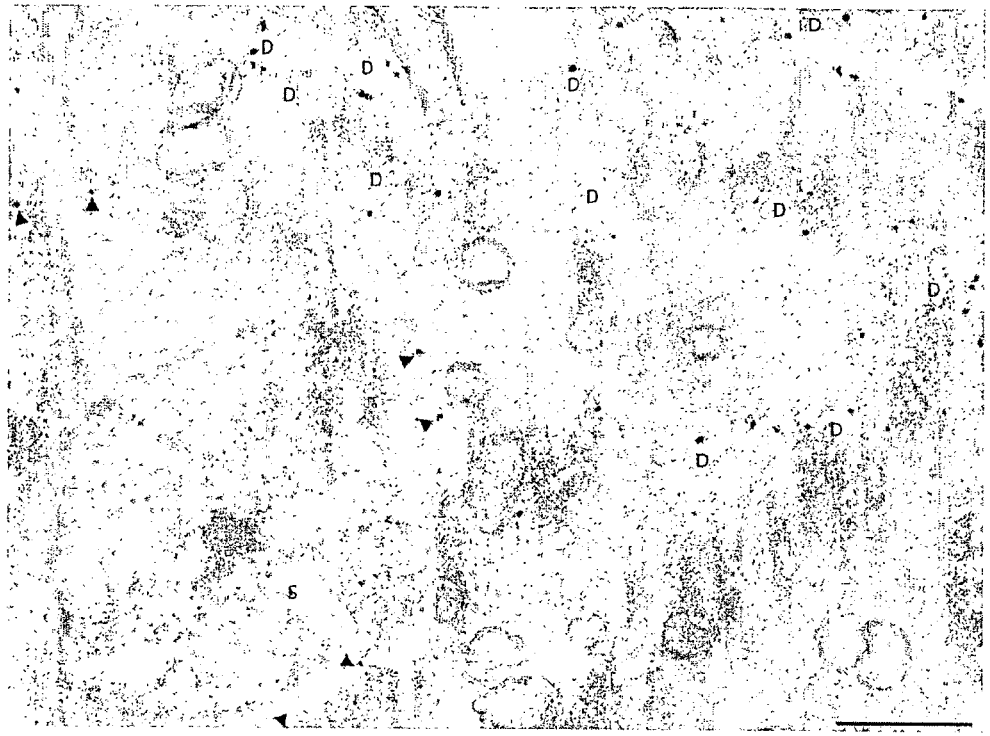
FIG. 6: KCC2 exporter expression is restricted to dorsal horn neurons, not sensory fibres. Although the KCC2 levels are below detection by immunoblotting from DRG (FIG. 4f), we verified whether KCC2 could be preferentially shuttled away from cell bodies to central terminals of primary afferents. a) Electron micrograph illustrating the presence of KCC2 on dendrites (D) in lamina I of the dorsal horn. Membrane-delimited immunogold staining on the soma (S) of a lamina I neuron is also shown (arrowheads). In contrast, no KCC2 immunostaining was observed in any of the randomly selected synaptic profiles examined (n=171). b) KCC2 immunoreactivity was also absent from central boutons (n=42 randomly selected central boutons) of synaptic glomeruli in laminae I and II (type I: $C_I$; left; type II: $C_{II}$; right; arrows indicate excitatory synapses, D: dendrite) that unequivocally correspond to central terminals of primary afferents (A- and C-fibres [34, 35]). Scale bars: a: 2 μm; b; 0.5 μm (left), 0.2 μm (right).
Figure 6B:
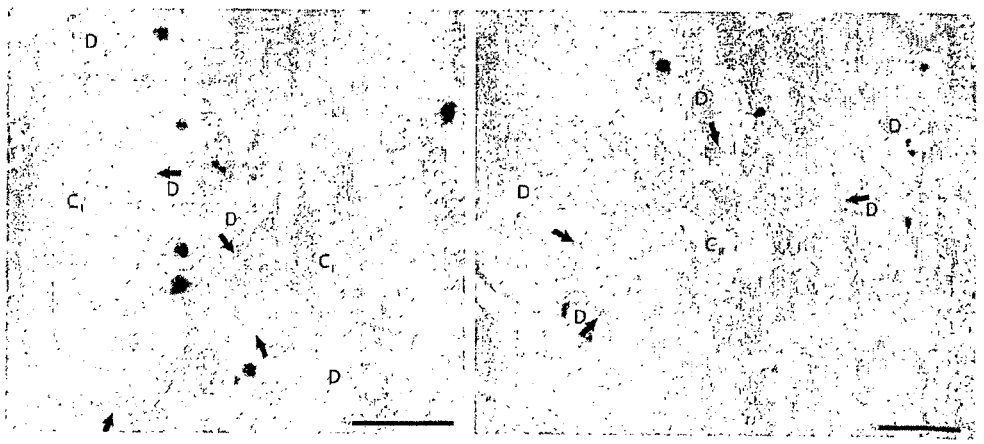

A critical feature of the spinal cord is that it employs two very distinct GABAergic inhibitory mechanisms: GABAergic control of the central terminals of sensory fibres already involves a depolarizing mechanism (39), in contrast to dorsal horn cells where GABAergic inhibition involves hyperpolarization. Thus, the change in KCC2 expression reported here affects the polarity of GABA action in only one of the two inhibitory mechanisms controlling sensory input. This is confirmed by the fact that primary afferents lack expression of KCC2 (FIGS. 4f, g; see also FIG. 6). GABA/glycine-mediated depolarization may also serve as a gating mechanism to enable excitation via voltage sensitive $Ca^{2+}$ channels (VSCCs) and NMDA receptor/channels (10). $Ca^{2+}$ influx via these channels is thought to be critical for the sensitization of spinal neurons (11). Indeed, blocking these $Ca^{2+}$ channels in humans by drugs such as gabapentin and ketamine has proven highly efficacious in the treatment of neuropathic pain (12-14). However, use of $Ca^{2+}$ channel blockers, particularly ketamine and other NMDA antagonists, is associated with many undesirable side effects (14, 15).

Example 3

In Vitro TrkB-Dependent Modulation of KCC2

Parasaggital slices (250-300 microm) were made from the dorsal horn of naïve rats or PNI rats. Slices were continually perfused with an oxygenated Ringer's solution and were permitted to equilibrate for at least 1.5 hours prior to manipulation. Unless otherwise specified, slices were further perfused with 10 microM CNQX, a blocker of non-NMDA ionotropic glutamate receptors. Recordings were made from visually-identified lamina I neurons using gramicidin-D perforated-patch or whole-cell voltage-clamp recordings. In both cases, pipettes were filled with an intracellular solution containing either potassium methyl sulphate or cesium gluconate as the major ionic species. $E_{anion}$ was measured by applying a series of brief (5-10 ms) applications of exogenous GABA to the soma of the neurons of interest; by manipulating the membrane potential of the neuron, the point at which GABA elicited neither an inward nor an outward anion current was taken as $E_{anion}$. All measurements of membrane potential were corrected for liquid junction potential, pipette offset, and resistances.

Figure 12:
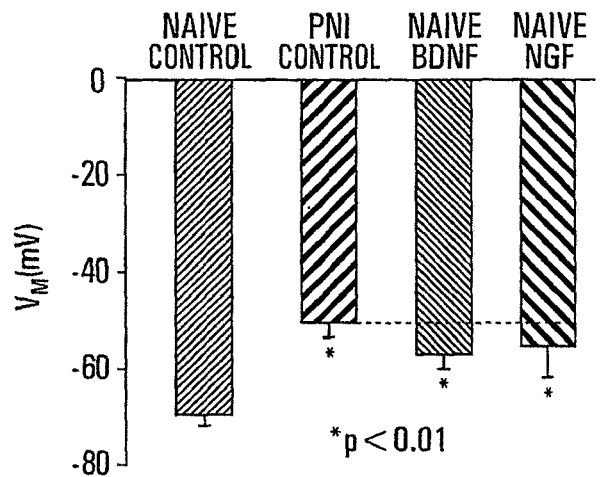
FIG. 12: Comparison of the anion (chloride and bicarbonate) reversal potential ($E_{anion}$) measured from lamina I neurons in slices, taken from naïve rats, perfused with BDNF, NGF or regular artificial cerebrospinal solution (ACSF; "control" in Figure). PNI—peripheral nerve injury.

As shown in FIG. 12, both brain-derived neurotrophic factor—(BDNF; 50 ng/ml in bath) mediated activation of TrkB and nerve growth factor—(NGF; 50 ng/ml in bath) mediated activation of TrkA caused a significant depolarization of the anion reversal potential ($E_{anion}$) in lamina I neurons taken from naïve rats.

Figure 13:
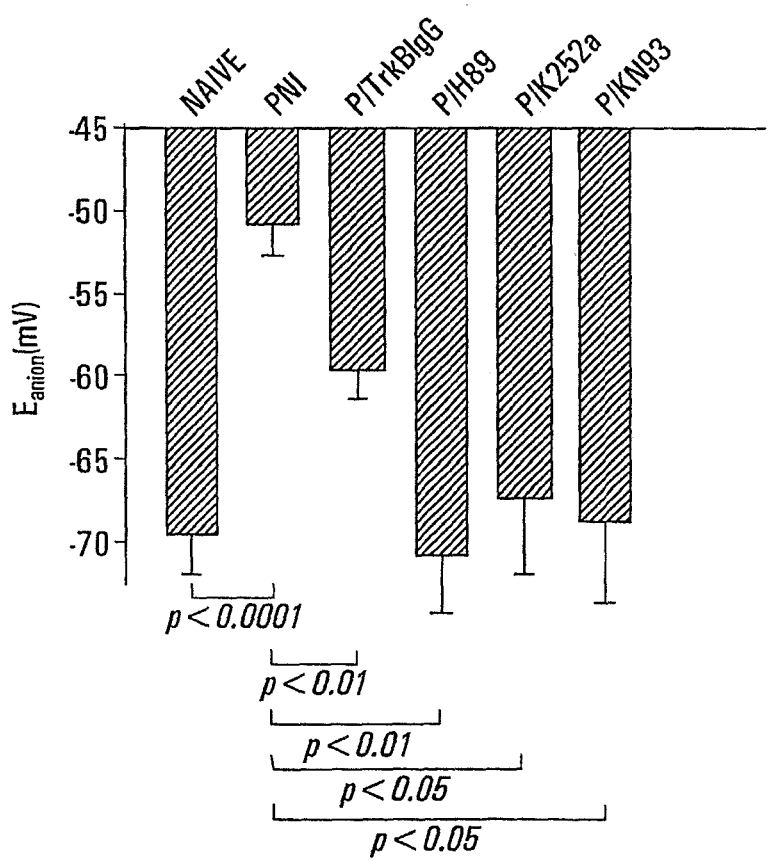
FIG. 13: Comparison of $E_{anion}$ measured in slices containing lamina I neurons taken from PNI rats treated, by bath application, with an antibody directed against TrkB (P/TrkBIgG), H-89 (P/H89), K-252a (P/K252a) and KN-93 (P/KN93). PNI—peripheral nerve injury.

Using slices taken from peripheral nerve injured (PNI) rats, where the $E_{anion}$ is chronically depolarized, application of various inhibitors of components of an intracellular pathway coupled to TrkB receptors were shown to cause a significant hyperpolarization of the $E_{anion}$ (bicarbonate and chloride), to levels similar to that observed in slices taken from naïve rats (FIG. 13). Agents that rendered this effect included, but are not limited to, an antibody directed against TrkB, (anti-TrkB-IgG 1 µg/ml in bath); K-252a, an inhibitor of TrkA/B autophosphorylation (200 nM in bath); H-89, a membrane-permeable inhibitor of cyclic AMP-dependent kinase (PKA); 15 in bath); and KN-93, a membrane permeable inhibitor of calmodulin-dependent kinase II and IV (5 µM in bath).

Example 4

TrkB-Dependent Modulation of Nociceptive Threshold In Vivo

All drugs used for local spinal delivery via intrathecal catheter were dissolved in 0.9% NaCl with or without 10% v/v DMSO. Intrathecal catheterization was performed by creating a small opening at the cisterna magna, and inserting a short P10 polyethylene tube into the subarachnoid space, caudally directed ~8 cm to the lumbar enlargement (L4-5) of the spinal cord. No drug administered produced motor disturbances or sedation, as assessed via analysis of grasping, righting and placing reflexes and other behavioral observations. Von Frey testing was used to assess the 50% withdrawal threshold to mechanical stimulation as previously described (41). All experiments were performed on intact, adult Sprague-Dawley rats.

Local spinal delivery of various agents using an intrathecal catheter led to the identification of several compounds that either effect a reduction of nociceptive threshold for tactile stimulation in naïve rats, or raise the nociceptive threshold in PNI rats.

Figure 14:
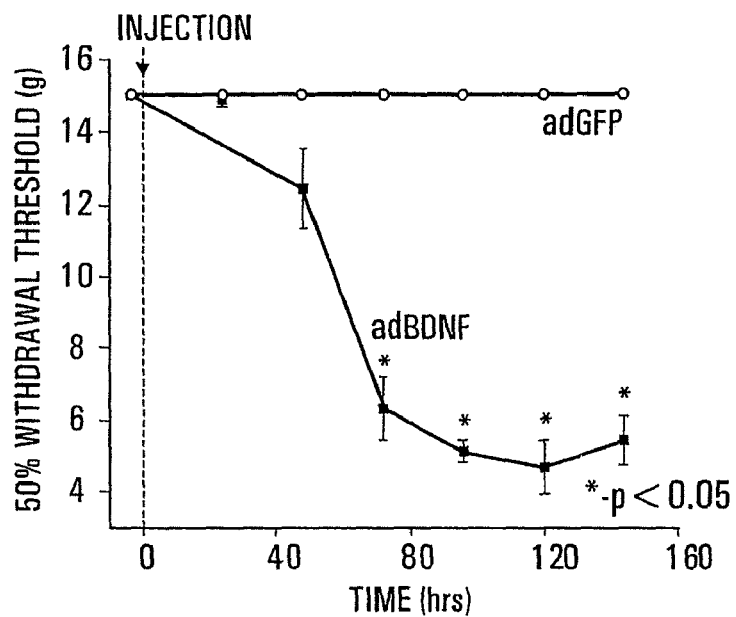
FIG. 14: Comparison between the nociceptive threshold for tactile stimulation of rats treated with an adenovirus transducing BDNF (■) and rats treated with an adenovirus transducing the green fluorescent protein (○).
Figure 15:
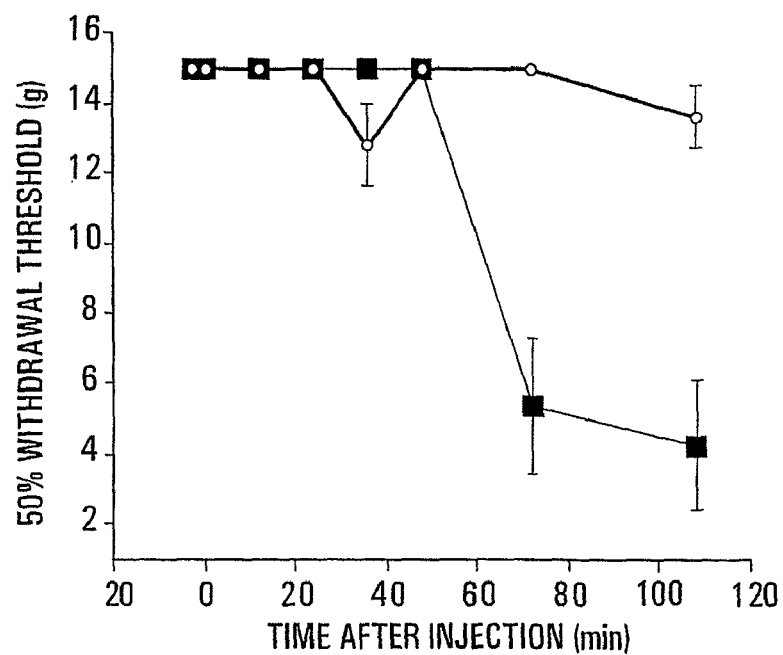
FIG. 15: Comparison between the nociceptive threshold for tactile stimulation of rats treated with human recombinant NGF (10 μg/day×6 days) (■) and rats treated with saline vehicle (○).

Local spinal delivery of either an adenovirus transducing BDNF (FIG. 14) or human recombinant BDNF (10 µg/day×6 days), but not of an adenovirus transducing the green-fluorescent protein, caused a significant decrease in the nociceptive threshold for mechanical stimulation in naïve rats. Likewise, intrathecal delivery of human recombinant NGF (FIG. 15; 10 µg/day×6 days) to naïve rats caused a very similar decrease in the said nociceptive threshold.

Figure 16:
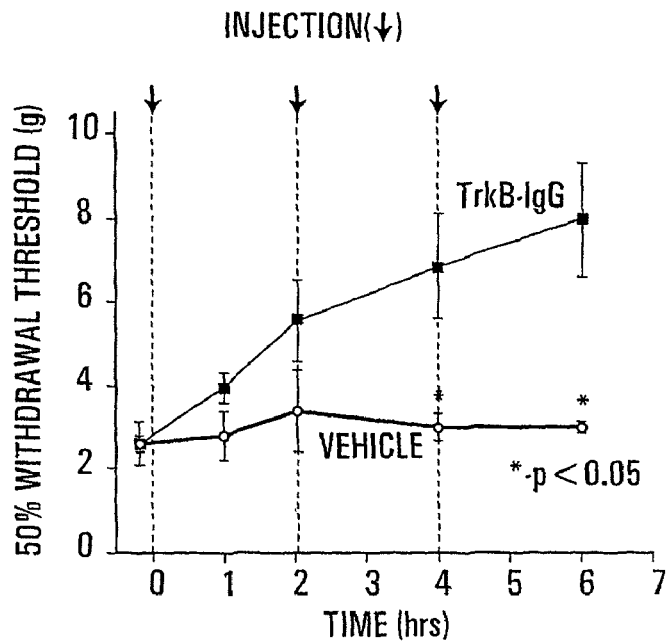
FIG. 16: Comparison between the nociceptive threshold for tactile stimulation of rats treated with the neutralizing anti-TrkB antibody (anti-TrkB-IgG 12 μg/2 hrs×3) (■) and rats treated with vehicle only (○).
Figure 17:
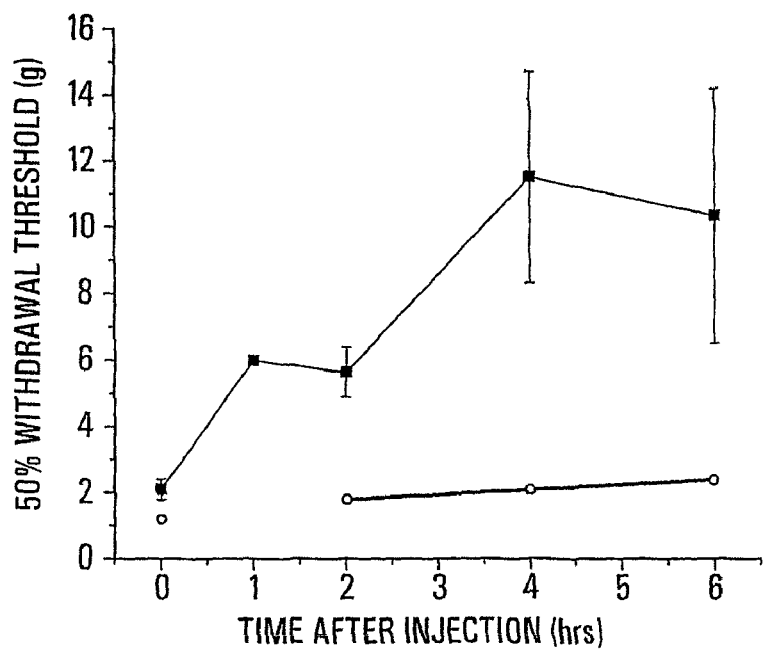
FIG. 17: Comparison between the nociceptive threshold for mechanical stimulation of rats treated with the PKA inhibitor H-89 (380 nmol) (■) and rats treated with vehicle only (○).

On the other hand, serial administration of antibody directed against TrkB (anti-TrkB-IgG 12 µg/2 hrs×3) via intrathecal catheter to PNI rats effected a significant increase in nociceptive threshold to mechanical stimulation (FIG. 16). Local spinal delivery of the PKA inhibitor H-89 (380 nmol) also caused an increase in the nociceptive threshold (FIG. 17).

Throughout this application, various references are cited, which describe more fully the state of the art to which this invention pertains. The disclosures of these references are hereby incorporated by reference into the present disclosure.

REFERENCES

1. Melzack, R. & Wall, P. D. (1965) *Science* 150:971-979.
2. Woolf, C. J. & Salter, M. W. (2000) *Science* 288:1765-1769.
3. Kontinen, V. K., et al. (2001) *Anesthesiology* 94:333-339.
4. Moore, K. A. et al. (2002) *J. Neurosci* 22:6724-6731.
5. Somers, D. L. & Clemente, F. R. (2002) *Neurosci Lett* 323:171-174.
6. Polgar, E., et al. Soc Neurosci Abstr 28, 655.3. Jun. 11, 2002.
7. Light, A. R. The initial processing of pain. Karger, Basel (1992).
8. Ebihara, S., et al. (1995) *J Physiol* 484 (Pt 1), 77-86.
9. Keller, A. F., et al. (2001) *J Neurosci* 21:7871-7880.
10. Staley, K. J., et al. (1995) *Science* 269:977-981.
11. Coderre, T. J. & Melzack, R. (1992) *J Neurosci* 12:3665-3670.
12. Serpell, M. G. (2002) *Pain* 99:557-566.
13. Rabben, T., et al. (1999) *J. Pharmacol. Exp. Ther.* 289:1060-1066.
14. Martin, T. J. & Eisenach, J. C. (2001) *J. Pharmacol. Exp. Ther.* 299:811-817.
15. Farber, N. B., et al. (2002) *Mol. Psychiatry* 7:726-733.
16. Mosconi, T. & Kruger, L. (1996) *Pain* 64:37-57.
17. Coderre, T. J. & Van, E., I. (1994) *Pain* 59:345-352.
18. Rivera, C. et al. (1999) *Nature* 397:251-255.
19. Prescott, S. A. & de Koninck, Y. (2002) *J Physiol* 539:817-836.
20. Payne, J. A., et al. (1996) *J. Biol. Chem.* 271:16245-16252.
21. Mount, D. B. et al. (1999) *J. Biol. Chem.* 274:16355-16362.
22. Kelsch, W. et al. (2001) *J Neurosci* 21:8339-8347.
23. Strange, K., et al. (2000) *Am. J. Physiol Cell Physiol* 279:C860-C867.
24. Shen, M. R. et al. (2001) *Proc. Natl. Acad. Sci. U. S. A* 98:14714-14719.
25. Gulyas, A. I., et al. (2001) *Eur. J. Neurosci.* 13:2205-2217.
26. Payne, J. A. (1997) *Am. J. Physiol* 273:C1516-C1525.
27. Flatman, P. W., et al. (1996) *Am. J. Physiol* 271:C255-C263.
28. Howard, H. C. et al. (2002) *Nat. Genet.* 32:384-392.

29. Sung, K. W., et al. (2000) *J. Neurosci.* 20:7531-7538.
30. Mainen, Z. F., et al. (1995) *Neuron* 15:1427-1439.
31. Traub, R. J. & Miles, R. Neuronal Networks of the Hippocampus. Cambridge, Cambridge, U.K. (1991).
32. Narikawa, K., et al. (2000) *J Neurophysiol* 84:2171-2174.
33. Furue, H., et al. (1999) *J Physiol* 521:529-535.
34. Ribeiro-da-Silva, A. & Coimbra, A. (1982) *J. Comp Neurol.* 209, 176-186.
35. Ribeiro-da-Silva, A. The Rat Nervous System. Paxinos, G. (ed.), pp. 47-59 (Academic Press, Sydney, Australia, 1995).
36. Sik, A., et al. (2000) *Neuroscience* 101, 51-65.
37. Gulyas, A. I., et al. (2001) *Eur. J. Neurosci.* 13, 2205-2217.
38. Delpire, E. & Mount, D. B. (2002) *Annu. Rev. Physiol.* 64:803-403.
39. Woo, N.-S., et al. (2002) *Hippocampus* 12:258-268.
40. Rudomin, P. & Schmidt, R. F. (1999) *Exp Brain Res* 129:1-37.
41. Chaplan et al., (1994) *J. Neuroscience Methods* 53:55-63.
42. Jarolimek at al. (1999) *J. Neuroscience* 19: 4695-704.

The invention claimed is:

1. A method of identifying a compound that may be used for the treatment of pain, said method comprising:
   (a) contacting a test compound with a cell expressing a CNS chloride transporter;
   (b) comparing an activity of said CNS chloride transporter in the presence of the test compound with an activity of said CNS chloride transporter in the absence of said test compound;
      wherein a modulation in said activity of said CNS chloride transporter in the presence relative to in the absence of said test compound is an indication that said test compound may be used for treatment of pain, wherein (i) if said CNS chloride transporter is a chloride exporter, said modulation is an increase, and (ii) if said CNS chloride transporter is a chloride importer, said modulation is a decrease; and
   (c) identifying a compound for the treatment of pain on the basis of said comparison.

2. The method of claim 1, wherein determining said activity comprises determining whether said test compound binds to said CNS chloride transporter.

3. The method of claim 1, wherein said CNS chloride transporter is a chloride exporter.

4. The method of claim 3, wherein said chloride exporter is $K^+$—$Cl^-$ cotransporter 2 (KCC2).

5. The method of claim 4, wherein KCC2 activity is determined by measuring a parameter selected from the group consisting of potassium or chloride transport, transport of an ion or particle that is a surrogate thereof, intracellular chloride level and anion reversal potential.

6. The method of claim 1, wherein said pain is selected from the group consisting of chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury and recurrent acute pain.

* * * * *